(12) United States Patent
Nakajima et al.

(10) Patent No.: US 9,023,588 B2
(45) Date of Patent: May 5, 2015

(54) RESIST UNDERLAYER FILM FORMING COMPOSITION CONTAINING SILICON HAVING NITROGEN-CONTAINING RING

(75) Inventors: Makoto Nakajima, Toyama (JP); Yuta Kanno, Toyama (JP); Wataru Shibayama, Toyama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/580,066

(22) PCT Filed: Feb. 18, 2011

(86) PCT No.: PCT/JP2011/053525
§ 371 (c)(1),
(2), (4) Date: Aug. 20, 2012

(87) PCT Pub. No.: WO2011/102470
PCT Pub. Date: Aug. 25, 2011

(65) Prior Publication Data
US 2012/0315765 A1    Dec. 13, 2012

(30) Foreign Application Priority Data

Feb. 19, 2010   (JP) ................................. 2010-034503

(51) Int. Cl.
| | |
|---|---|
| G03F 7/075 | (2006.01) |
| G03F 7/09 | (2006.01) |
| G03F 7/26 | (2006.01) |
| C07F 7/18 | (2006.01) |
| C09D 183/08 | (2006.01) |
| C08G 77/388 | (2006.01) |

(52) U.S. Cl.
CPC .............. *C07F 7/1836* (2013.01); *G03F 7/094* (2013.01); *G03F 7/0751* (2013.01); *C09D 183/08* (2013.01); *C08G 77/388* (2013.01)

(58) Field of Classification Search
CPC ..... G03F 7/075; G03F 7/0757; G03F 7/0758; G03F 7/09; G03F 7/26; G03F 7/30; G03F 7/36; G03F 7/38; G03F 7/40; C07F 7/081; C07F 7/0812; C07F 7/0892
USPC .............. 430/272.1, 311, 313, 316, 317, 325, 430/326, 327, 330; 556/407, 411
See application file for complete search history.

(56) References Cited

U.S. PATENT DOCUMENTS

| | | | | |
|---|---|---|---|---|
| 3,813,364 | A | * | 5/1974 | De Zuba et al. ............... 524/588 |
| 4,769,308 | A | * | 9/1988 | Hiruma et al. ............. 430/272.1 |
| 5,100,503 | A | | 3/1992 | Allman et al. |

(Continued)

FOREIGN PATENT DOCUMENTS

| | | |
|---|---|---|
| EP | 0 260 976 A2 | 3/1988 |
| EP | 1 798 599 A1 | 6/2007 |

(Continued)

OTHER PUBLICATIONS

May 24, 2011 Translation of the Written Opinion issued in PCT/JP2011/053525.
May 24, 2011 Translation of the International Search Report issued in PCT/JP2011/053525.
Mar. 10, 2009 International Search Report issued in Application No. PCT/JP2009/052535.
Nov. 2, 2009 International Search Report issued in International Application No. PCT/JP2009/064301.
Feb. 1, 2013 Office Action issued in U.S. Appl. No. 13/681,186.
Mar. 9, 2010 International Search Report issued in International Patent Application. No. PCT/JP2009/070984.
May 8, 2012 Search Report issued in European Patent Application No. 09833458.4.
Feb. 7, 2013 Office Action issued in. U.S. Appl. No. 13/133,751.
U.S. Appl. No. 13/133,751, filed Aug. 4, 2011.

(Continued)

*Primary Examiner* — Anca Eoff
(74) *Attorney, Agent, or Firm* — Oliff PLC

(57) ABSTRACT

There is provided a resist underlayer film forming composition for lithography for forming a resist underlayer film capable of being used as a hardmask. A resist underlayer film forming composition for lithography, includes as a silane compound, a hydrolyzable organosilane, a hydrolysis product thereof, or a hydrolysis-condensation product thereof, wherein the hydrolyzable organosilane is a hydrolyzable organosilane of Formula (1):

$$R^1_a R^2_b Si(R^3)_{4-(a+b)} \quad \text{Formula (1)}$$

wherein $R^1$ is Formula (2):

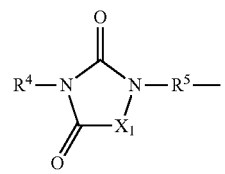

Formula (2)

in which $R^4$ is an organic group, and $R^5$ is a $C_{1-10}$ alkylene group, a hydroxyalkylene group, a sulfide bond, an ether bond, an ester bond, or a combination thereof, $X_1$ is Formula (3), Formula (4), or Formula (5):

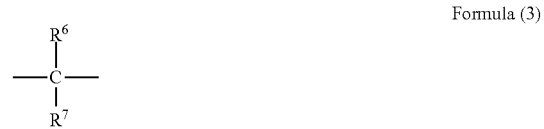

Formula (3)

Formula (4)

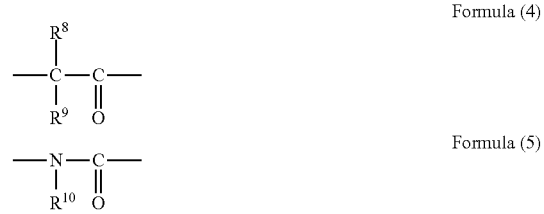

Formula (5)

$R^2$ is an organic group, and $R^3$ is a hydrolysable group.

16 Claims, 2 Drawing Sheets

(56) References Cited

U.S. PATENT DOCUMENTS

| | | | |
|---|---|---|---|
| 5,152,834 A | 10/1992 | Allman | |
| 5,209,775 A | 5/1993 | Bank et al. | |
| 5,302,198 A | 4/1994 | Allman | |
| 5,472,488 A | 12/1995 | Allman | |
| 5,527,872 A | 6/1996 | Allman | |
| 5,665,845 A | 9/1997 | Allman | |
| 5,962,188 A | 10/1999 | DeBoer et al. | |
| 6,576,393 B1 | 6/2003 | Sugita et al. | |
| 7,192,683 B2 | 3/2007 | Yamasaki et al. | |
| 2004/0253461 A1 | 12/2004 | Ogihara et al. | |
| 2004/0266925 A1* | 12/2004 | Shiono | 524/262 |
| 2006/0003252 A1 | 1/2006 | Hirayama et al. | |
| 2006/0093959 A1 | 5/2006 | Huang et al. | |
| 2007/0190459 A1 | 8/2007 | Hashimoto et al. | |
| 2007/0224816 A1 | 9/2007 | Uh et al. | |
| 2008/0076059 A1 | 3/2008 | Abdallah et al. | |
| 2008/0107997 A1 | 5/2008 | Hiroi et al. | |
| 2008/0312400 A1* | 12/2008 | Yamashita et al. | 528/30 |
| 2009/0050020 A1 | 2/2009 | Konno et al. | |
| 2009/0130594 A1 | 5/2009 | Takei et al. | |
| 2009/0148789 A1 | 6/2009 | Amara et al. | |
| 2009/0162782 A1 | 6/2009 | Takei et al. | |
| 2010/0151384 A1 | 6/2010 | Konno et al. | |
| 2010/0304305 A1* | 12/2010 | Nakajima et al. | 430/316 |
| 2010/0330505 A1 | 12/2010 | Nakajima et al. | |
| 2011/0143149 A1 | 6/2011 | Shibayama et al. | |
| 2011/0287369 A1 | 11/2011 | Shibayama et al. | |
| 2012/0070994 A1 | 3/2012 | Kanno et al. | |
| 2012/0178261 A1 | 7/2012 | Kanno et al. | |
| 2013/0023602 A1* | 1/2013 | Dorman | 523/122 |
| 2013/0078814 A1 | 3/2013 | Shibayama et al. | |

FOREIGN PATENT DOCUMENTS

| | | |
|---|---|---|
| EP | 1 855 159 A1 | 11/2007 |
| EP | 2 249 204 A1 | 11/2010 |
| JP | A-54-123965 | 9/1979 |
| JP | A-05-027444 | 2/1993 |
| JP | A-05-311158 | 11/1993 |
| JP | A-05-333292 | 12/1993 |
| JP | A-6-1796 | 1/1994 |
| JP | A-06-228459 | 8/1994 |
| JP | A-08-053560 | 2/1996 |
| JP | A-10-209134 | 8/1998 |
| JP | A-10-510860 | 10/1998 |
| JP | A-11-12544 | 1/1999 |
| JP | A-11-258813 | 9/1999 |
| JP | A-2000-282014 | 10/2000 |
| JP | A-2001-093824 | 4/2001 |
| JP | A-2001-294810 | 10/2001 |
| JP | A-2004-276603 | 10/2004 |
| JP | A-2005-070776 | 3/2005 |
| JP | A-2005-255858 | 9/2005 |
| JP | A-2006-182688 | 7/2006 |
| JP | A-2006-272588 | 10/2006 |
| JP | A-2007-031627 | 2/2007 |
| JP | A-2007-081133 | 3/2007 |
| JP | A-2007-241259 | 9/2007 |
| JP | A-2007-258622 | 10/2007 |
| JP | A-2008-038131 | 2/2008 |
| JP | A-2008-519297 | 6/2008 |
| JP | A-2008-213177 | 9/2008 |
| JP | A-2008-309929 | 12/2008 |
| JP | A-2009-244722 | 10/2009 |
| WO | WO 96/18918 | 6/1996 |
| WO | WO 98/28366 A1 | 7/1998 |
| WO | WO 00/01752 A1 | 1/2000 |
| WO | WO 2004/055598 A1 | 7/2004 |
| WO | WO 2005/088398 A1 | 9/2005 |
| WO | WO 2006/093057 A1 | 9/2006 |
| WO | WO 2007/066597 A1 | 6/2007 |
| WO | WO 2008/038863 A1 | 4/2008 |
| WO | WO 2009/034998 A1 | 3/2009 |
| WO | WO 2009/041511 A1 | 4/2009 |
| WO | WO 2009/104552 A1 | 8/2009 |
| WO | WO 2009/111121 A2 | 9/2009 |
| WO | WO 2009/111122 A2 | 9/2009 |

OTHER PUBLICATIONS

Jun. 22, 2010 Written Opinion of ISA issued in International Patent Application No. PCT/JP2010/059117 (translation).
Jun. 22, 2010 International Search Report issued in International Patent Application No. PCT/JP2010/059117.
Oct. 19, 2010 International Search Report issued in International Patent Application No. PCT/JP2010/065307.
Jun. 7, 2012 Office Action issued in U.S. Appl. No. 12/867,587.
Mar. 21, 2013 Final Rejection issued in U.S. Appl. No. 12/867,587.
Oct. 18, 2012 Restriction Requirement issued in U.S. Appl. No. 13/133,751.
Dec. 9, 2011 European Search Report issued in Application No. 09712238.6.
U.S. Appl. No. 12/867,587, filed Aug. 13, 2010.
U.S. Appl. No. 13/681,186, filed Nov. 19, 2012.
U.S. Appl. No. 13/375,517, filed Dec. 1, 2011.
U.S. Appl. No. 13/496,768, filed Mar. 16, 2012.
U.S. Appl. No. 13/058,109, filed Feb. 8, 2011.
U.S. Office Action dated Oct. 21, 2013 from U.S. Appl. No. 13/681,186.
U.S. Office Action dated Oct. 4, 2013 from U.S. Appl. No. 13/058,109.
U.S. Office Action dated Nov. 29, 2013 from U.S. Appl. No. 13/375,517.
Notice of Examination Opinion and Search Report dated Feb. 6, 2014 from Taiwanese Patent Application No. 098143678 (with English-language translation).
Office Action cited in U.S. Appl. No. 13/496,768 on Jan. 3, 2014.
Office Action cited in U.S. Appl. No. 13/133,751 on Dec. 26, 2013.
U.S. Office Action dated Sep. 11, 2014 from U.S. Appl. No. 12/867,587.
U.S. Office Action dated Sep. 10, 2014 from U.S. Appl. No. 13/375,517.

\* cited by examiner

RESIST UNDERLAYER FILM FORMING COMPOSITION CONTAINING SILICON HAVING NITROGEN-CONTAINING RING

TECHNICAL FIELD

The present invention relates to a composition for forming an underlayer film between a substrate and a resist (for example, a photoresist and an electron beam resist) that are used in the production of semiconductor devices. More specifically, the present invention relates to a resist underlayer film forming composition for lithography for forming an underlayer film used for an underlayer of a photoresist in a lithography process of the production of semiconductor devices. In addition, the present invention relates to a forming method of a resist pattern using the underlayer film forming composition.

The resist underlayer film forming composition contains a polymer containing a silyl group as a substituent on a nitrogen atom, and particularly, a polymer represented by a silyl isocyanurate.

BACKGROUND ART

Conventionally, in the production of semiconductor devices, fine processing by lithography using a photoresist has been performed. The fine processing is a processing method for forming fine convexo-concave shapes corresponding to the pattern on the surface of a substrate by: forming a thin film of a photoresist on a semiconductor substrate such as a silicon wafer; irradiating the resultant thin film with active rays such as ultraviolet rays through a mask pattern in which a pattern transferred to a semiconductor device is depicted; performing development; and subjecting the substrate to etching processing using the resultant photoresist film in which the obtained pattern is formed as a protecting film. Recently, however, semiconductor devices with higher densities have increased and the adopted active rays tend to have a shorter wavelength, such as KrF excimer laser (248 nm) and further ArF excimer laser (193 nm), replacing ultraviolet rays. Following such a tendency, the influence of reflection of active rays on a semiconductor substrate has become a large problem.

In addition, as an underlayer film between the semiconductor substrate and the photoresist, the use of a film known as a hardmask containing a metal element such as silicon and titanium (see, for example Patent Document 1) is performed. In this case, the resist and the hardmask have components largely different from each other, so that the removal rates of the resist and the hardmask by dry etching largely depend on the type of a gas used for dry etching. By appropriately selecting the type of a gas, the hardmask can be removed by dry etching without a large decrease in the film thickness of the photoresist.

Thus, in the production of semiconductor devices in recent years, for achieving various effects such as the reflection preventing effect, a resist underlayer film is disposed between the semiconductor substrate and the photoresist. The studies of a composition for a resist underlayer film have been also performed until today, however, due to the diversity of characteristics required for the composition and so on, the development of a novel material for the resist underlayer film is desired.

In addition, there is disclosed the application of a film formed from a polysiloxane material containing cyanuric acid to a lithography process (see Patent Document 2).

RELATED-ART DOCUMENTS

Patent Documents

Patent Document 1: Japanese Patent Application Publication No. JP-A-11-258813
Patent Document 2: International Publication No. WO 2009/034998 pamphlet

SUMMARY OF THE INVENTION

Problem to be Solved by the Invention

It is an object of the present invention to provide a resist underlayer film forming composition for lithography capable of being used in the production of a semiconductor device. More in detail, it is an object of the present invention to provide a resist underlayer film forming composition for lithography for forming a resist underlayer film capable of being used as a hardmask. In addition, it is an object of the present invention to provide a resist underlayer film forming composition for lithography for forming a resist underlayer film capable of being used as an anti-reflective coating. Furthermore, it is an object of the present invention to provide a resist underlayer film for lithography causing no intermixing with a resist and having a dry etching rate higher than that of the resist, and a resist underlayer film forming composition for forming the underlayer film.

As the miniaturization of a pattern has progressed, for preventing the reflection of an activated light on the substrate, a resist underlayer film having a high refractive index has become required. By a chromophore represented by a phenyl group, although a high refractive index can be obtained, an absorption coefficient relative to an activated light is high and an appropriate optical constant cannot be controlled. While it has been already reported that an isocyanurate group exhibits a high refractive index and a low absorption coefficient, so that the optical constant thereof can be easily controlled, there is a problem in that a silane having a bis-silane structure or a tri-silane structure in one molecule thereof is used, and therefore, gelation is easily caused and a stable polymer is hardly obtained.

Means for Solving the Problem

The present invention provides, according to a first aspect, a resist underlayer film forming composition for lithography containing as a silane compound, a hydrolyzable organosilane, a hydrolysis product thereof, or a hydrolysis-condensation product thereof, in which a hydrolyzable organosilane of Formula (1) is contained as the hydrolyzable organosilane:

Formula (1)

[where $R^1$ is Formula (2):

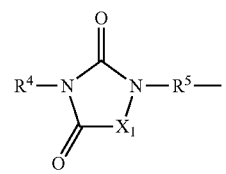

Formula (2)

[in Formula (2), $R^4$ is a hydrogen atom, a $C_{1-10}$ alkyl group, an alkenyl group, an epoxy group, a sulfonyl group, or an organic group containing these groups; $R^5$ is a $C_{1-10}$ alkylene group, a hydroxyalkylene group, a sulfide bond, an ether bond, an ester bond, or a combination thereof; $X_1$ is Formula (3), Formula (4), or Formula (5):

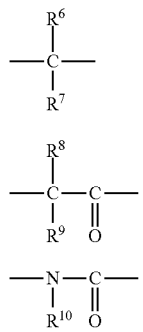

Formula (3)

Formula (4)

Formula (5)

(in Formula (3), Formula (4), and Formula (5), $R^6$ to $R^{10}$ are independently a hydrogen atom, a $C_{1-10}$ alkyl group, an alkenyl group, an epoxy group, a sulfonyl group, or an organic group containing these groups)] and is bonded to a silicon atom through a Si—C bond; $R^2$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, or a cyano group, or a combination thereof, and is bonded to a silicon atom through a Si—C bond; $R^3$ is an alkoxy group, an acyloxy group, or a halogen group; and a is an integer of 1 and b is an integer of 0 or 1, where a+b is an integer of 1 or 2], according to a second aspect, the composition according to the first aspect containing as the silane compound, a combination of a hydrolyzable silane of Formula (6):

$R^{11}{}_c Si(R^{12})_{4-c}$         Formula (6)

(where $R^{11}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, a sulfonyl group, a sulfide bond, an ether bond, an ester bond, a sulfonamide group, or a cyano group, or a combination thereof, and is bonded to a silicon atom through a Si—C bond; $R^{12}$ is an alkoxy group, an acyloxy group, or a halogen group; and c is an integer of 0 to 3) with the hydrolyzable organosilane of Formula (1), a hydrolysis product thereof, or a hydrolysis-condensation product thereof, according to a third aspect, the composition according to the first aspect or the second aspect containing as the silane compound, a hydrolysis-condensation product of the hydrolyzable organosilane of Formula (1) or a hydrolysis-condensation product of the organosilane of Formula (1) and the hydrolyzable silane of Formula (6) as a polymer, according to a fourth aspect, the composition according to any one of the first aspect to the third aspect further containing as the silane compound, a hydrolyzable organosilane of Formula (7):

$R^{13}{}_d R^{14}{}_e Si(R^{15})_{4-(d+e)}$         Formula (7)

(where $R^{13}$ is a cyclic amine or an organic group containing the same and is bonded to a silicon atom through a Si—N bond or a Si—C bond; $R^{14}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond; $R^{15}$ is an alkoxy group, an acyloxy group, or a halogen group; and d is an integer of 1 or 2 and e is an integer of 0 or 1, where d+e is an integer of 1 or 2), a hydrolysis product thereof, or a hydrolysis-condensation product thereof, according to a fifth aspect, the composition according to any one of the first aspect to the fourth aspect further containing as the silane compound, a hydrolyzable organosilane of Formula (8):

$R^{16}{}_f R^{17}{}_g Si(R^{18})_{4-(f+g)}$         Formula (8)

(where $R^{16}$ is an alkoxyphenyl group, an acyloxyphenyl group, or an organic group containing these groups and is bonded to a silicon atom through a Si—C bond; $R^{17}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond; $R^{18}$ is an alkoxy group, an acyloxy group, or a halogen group; where $R^{16}$ and $R^{17}$ optionally together form a ring; and f is an integer of 1 or 2 and g is an integer of 0 or 1, where f+g is an integer of 1 or 2), a hydrolysis product thereof, or a hydrolysis-condensation product thereof, according to a sixth aspect, the composition according to any one of the first aspect to the fifth aspect further containing an acid, according to a seventh aspect, the composition according to any one of the first aspect to the sixth aspect further containing a salt, according to an eighth aspect, the composition according to any one of the first aspect to the seventh aspect further containing water, according to a ninth aspect, the composition according to any one of the first aspect to the eighth aspect further containing bisphenol S or a derivative thereof, according to a tenth aspect, the composition according to any one of the second aspect to the ninth aspect containing as the silane compound, at least the hydrolyzable organosilane of Formula (1) that is a hydrolyzable organosilane containing diallyl isocyanurate and the hydrolyzable silane of Formula (6) that is a tetraalkoxysilane, according to an eleventh aspect, the composition according to any one of the second aspect to the ninth aspect containing as the silane compound, at least the hydrolyzable organosilane of Formula (1) that is a hydrolyzable organosilane containing diallyl isocyanurate and the hydrolyzable silane of Formula (6) that is a tetraalkoxysilane and an unsubstituted or substituted phenyltrialkoxysilane, according to a twelfth aspect, the composition according to any one of the fourth aspect to the ninth aspect containing as the silane compound, at least the hydrolyzable organosilane of Formula (1) that is a hydrolyzable organosilane containing diallyl isocyanurate, the hydrolyzable silane of Formula (6) that is a tetraalkoxysilane, and the hydrolyzable organosilane of Formula (8) that is a hydrolyzable organosilane containing an alkoxyphenyl group, according to a thirteenth aspect, the composition according to any one of the fourth aspect to the ninth aspect containing as the silane compound, at least the hydrolyzable organosilane of Formula (1) that is a hydrolyzable organosilane containing diallyl isocyanurate, the hydrolyzable silane of Formula (6) that is a tetraalkoxysilane and an unsubstituted or substituted phenyltrialkoxysilane, and the hydrolyzable organosilane of Formula (8) that is a hydrolyzable organosilane containing an alkoxyphenyl group, according to a fourteenth aspect, a resist underlayer film obtained by applying the resist underlayer film forming composition described in any one of the first aspect to the thirteenth aspect on a semiconductor substrate and baking the resultant coating film, according to a fifteenth aspect, a production method of a semiconductor device containing: a process of applying the resist underlayer film forming composition described in any one of the first aspect to the thirteenth aspect on a semiconductor substrate and baking the resultant coating film to form a resist underlayer film; a process of applying a resist film forming composition on the resist underlayer film to form a resist film; a process of exposing the resist film to light; a process of developing the resist film after the exposure to obtain a patterned resist film; a process of etching the resist underlayer film according to the patterned resist film to pattern the resist underlayer film; and a process of processing the semiconductor substrate according to the patterned resist film and the patterned resist underlayer film, according to a sixteenth aspect, a production method of a semiconductor device containing: a process of forming an organic underlayer film on a semiconductor substrate; a process of applying the resist underlayer film forming composition described in any one of the first aspect to the thirteenth aspect on the organic underlayer film and baking the resultant coating film to form a resist underlayer film; a process of applying a resist film forming composition on the resist underlayer film to form a resist film; a process of exposing the resist film to light; a process of developing the resist after the exposure to obtain a patterned resist film; a process of etching the resist underlayer film according to the patterned resist film to pattern the resist underlayer film; a process of etching the organic underlayer film according to the pattered resist underlayer film to pattern the organic underlayer film; and a process of processing the semiconductor substrate according to the patterned organic underlayer film, and according to a seventeenth aspect, a hydrolyzable organosilane of Formula (E-1):

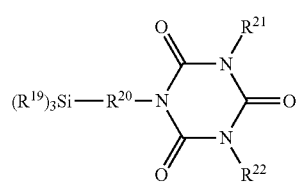

Formula (E-1)

(where $R^{19}$ is an alkoxy group, an acyloxy group, or a halogen group; $R^{20}$ is a $C_{1-10}$ alkylene group or a $C_{2-10}$ alkylene group through a sulfide bond, an ether bond, or an ester bond; and $R^{21}$ and $R^{22}$ are individually a $C_{1-3}$ alkyl group or a glycidyl group).

Effects of the Invention

The resist underlayer film of the present invention functions as a hardmask and a hydrolyzable group in the structure of a hydrolyzable organosilane of Formula (1) such as an alkoxy group, an acyloxy group, and a halogen group is hydrolyzed or partially hydrolyzed to generate a silanol group and forms thereafter a polymer in a polyorganosiloxane structure by a condensation reaction between these silanol groups. The polyorganosiloxane structure has a satisfactory function as a hard mask.

The bonding moiety contained in the polyorganosiloxane structure has a carbon-nitrogen bond or a carbon-oxygen bond having a dry etching rate by a halogen-based gas higher than that of a carbon-carbon bond, so that the bonding moiety is effective for transferring an upper layer resist pattern to the resist underlayer film.

The film having the polyorganosiloxane structure (intermediate film) is effective as a hardmask for etching an organic underlayer film existing under the intermediate film or for processing (etching) the substrate. That is, the film has satisfactory dry etching resistance during the substrate processing or relative to an oxygen-based dry etching gas used for etching the organic underlayer film.

That is, the resist underlayer film of the present invention can possess an etching rate higher than the dry etching rate of the upper layer resist film, and dry etching resistance during the substrate processing or the like.

In the resist underlayer film forming composition of the present invention, by using an isocyanurate-containing hydrolyzable organosilane of Formula (1), the composition can obtain easily a polymer without being gelled and can easily control optical constants such as a high refractive index and a low absorption coefficient. An isocyanurate group can produce a resist underlayer film having high surface modification ability and having high adhesion with the resist film, the substrate, and the organic underlayer film on the substrate.

Furthermore, the resist underlayer film formed from the resist underlayer film forming composition of the present invention can be used as a resist underlayer film in the production of semiconductor devices and can also possess besides the function as a hardmask, the function as an antireflective coating.

The resist underlayer film forming composition of the present invention can form a resist underlayer film causing no intermixing with the resist.

Furthermore, by using the resist underlayer film forming composition of the present invention, even when a resist film of a thin film is used for forming a fine pattern, a substrate can be advantageously patterned.

MODES FOR CARRYING OUT THE INVENTION

Figure 1:
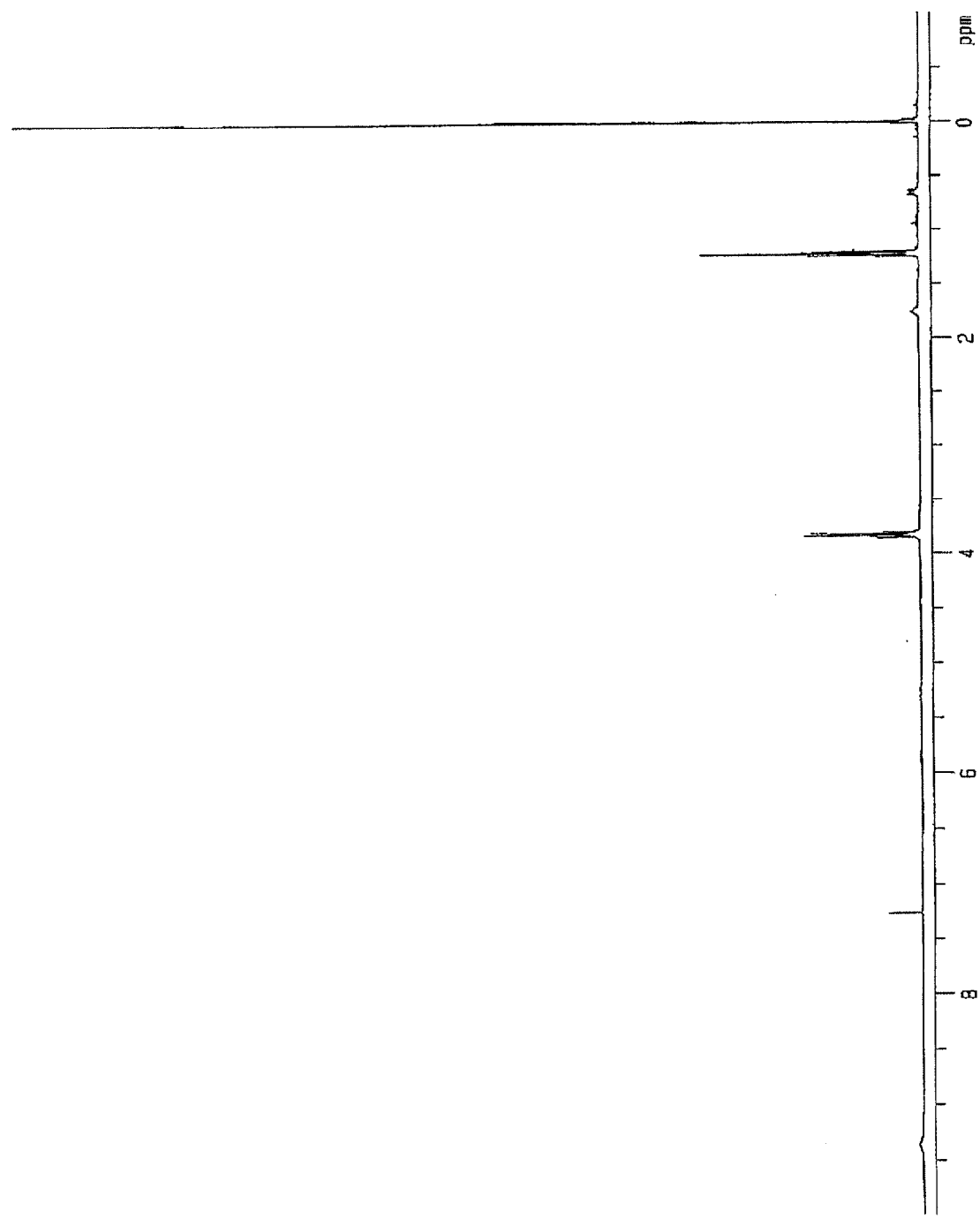
FIG. 1 is a graph showing an NMR spectrum of a silane (E-2) obtained in Raw Material Synthesis Example 1.
Figure 2:
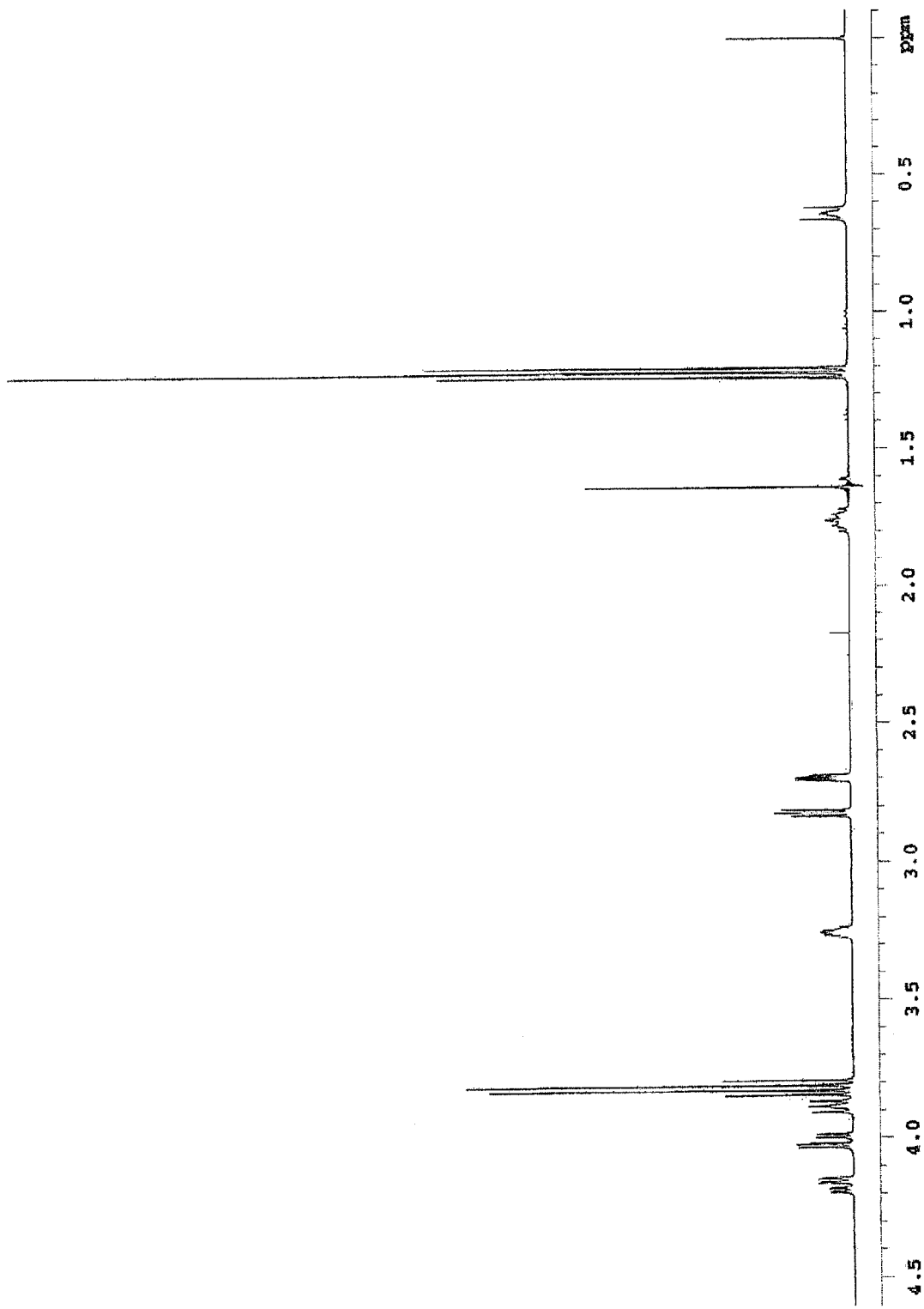
FIG. 2 is a graph showing an NMR spectrum of a silane (E-3) obtained in Raw Material Synthesis Example 2.

In the present invention, the resist underlayer film is formed by an applying method either on a substrate or on an organic underlayer film formed on a substrate and, on the resist underlayer film, a resist film (for example, a photoresist or an electron beam resist) is formed. Then, a resist pattern is formed by exposure through a mask and development. By dry etching the resist underlayer film using the resist film in which the resist pattern is formed to transfer the pattern, the substrate is processed using the patterned resist underlayer film. Alternatively, by etching the organic underlayer film to transfer the pattern, the substrate is processed by the etched organic underlayer film.

In forming a fine pattern in the resist film, for preventing a pattern collapse, resist films tend to have smaller thickness. Due to the thinning of the resist, the dry etching for transferring the pattern of the resist film to a film under the resist cannot be used to transfer the pattern unless the etching rate of the underlayer film is higher than that of the upper layer film. In the present invention, the substrate is coated with the resist underlayer film (containing an inorganic silicon-based compound) of the present specification either with or without an organic underlayer film interposed therebetween, and then the resist underlayer film is coated with a resist film (an organic resist film). An organic component film and an inorganic component film have dry etching rates largely different from each other depending on the selection of the etching gas. The dry etching rate of the organic component film is enhanced by an oxygen-based gas, while the dry etching rate of the inorganic component film is enhanced by a halogen-containing gas.

For example, a resist pattern is formed, and the pattern is transferred to the resist underlayer film of the present specification, which is located under the resist pattern, by dry etching the resist underlayer film with a halogen-containing gas. Using the resist underlayer film to which the pattern is transferred, and the substrate is processed with a halogen-containing gas. Alternatively, by dry etching the organic underlayer film under the resist underlayer film to which the pattern is transferred with an oxygen-based gas using the resist underlayer film, the pattern is transferred to the organic underlayer film, and the substrate is processed with a halogen-containing gas using the organic underlayer film to which the pattern is transferred.

The present invention relates to a resist underlayer film forming composition for lithography containing as a silane compound, a hydrolyzable organosilane, a hydrolysis product thereof, or a hydrolysis-condensation product thereof, in which the silane compound is a hydrolyzable organosilane of Formula (1).

The resist underlayer film forming composition of the present invention may contain a silicon atom having a partial structure of Formula (2) in a content of less than 50% by mole, for example 0.5 to 30% by mole, 0.5 to 25% by mole, 0.5 to 15% by mole, or 0.5 to 1% by mole, based on the number of moles of the silicon atom in the whole silane compound contained in the composition.

The resist underlayer film forming composition of the present invention contains a hydrolyzable organosilane of Formula (1), a hydrolysis product thereof, or a hydrolysis-condensation product thereof, and a solvent. The resist underlayer film forming composition of the present invention may contain, as optional components, an acid, water, an alcohol, a curing catalyst, an acid generator, other organic polymers, light absorptive compounds, surfactants, and the like.

The solid content of the resist underlayer film forming composition of the present invention is, for example 0.1 to 50% by mass, 0.1 to 30% by mass, or 0.1 to 25% by mass Here, the solid content is a component remaining after subtracting a solvent component from the whole component of the resist underlayer film forming composition.

The ratio constituted by the hydrolyzable organosilane, a hydrolysis product thereof, and a hydrolysis-condensation product thereof in the solid content is 20% by mass or more, for example 50 to 100% by mass, 60 to 100% by mass, or 70 to 100% by mass.

The hydrolyzable organosilane used in the present invention has a structure of Formula (1).

$R^1$ in Formula (1) is a structure of Formula (2) and is bonded to a silicon atom through a Si—C bond. $R^2$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, or a cyano group, or a combination thereof, and is bonded to a silicon atom through a Si—C bond. $R^3$ is an alkoxy group, an acyloxy group, or a halogen group. a is an integer of 1 and b is an integer of 0 or 1, where (a+b) is an integer of 1 or 2.

In Formula (2), $R^4$ is a hydrogen atom, a $C_{1-10}$ alkyl group, an alkenyl group, an epoxy group, a sulfonyl group, or an organic group containing these groups; $R^5$ is a $C_{1-10}$ alkylene group, a hydroxyalkylene group, a sulfide bond, an ether bond, an ester bond, or a combination thereof; and $X_1$ is Formula (3), Formula (4), or Formula (5).

In Formula (3), Formula (4), and Formula (5), $R^6$ to $R^{10}$ are independently a hydrogen atom, a $C_{1-6}$ alkyl group, an alkenyl group, an epoxy group, a sulfonyl group, or an organic group containing these groups.

The alkyl group is a linear or branched $C_{1-10}$ alkyl group and examples of the alkyl group include a methyl group, an ethyl group, an n-propyl group, an isopropyl group, an n-butyl group, an isobutyl group, a sec-butyl group, a tert-butyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, and a 1-ethyl-2-methyl-n-propyl group.

As the alkyl group, a cyclic alkyl group can also be used and examples of the cyclic alkyl group include $C_{1-10}$ cyclic alkyl groups such as a cyclopropyl group, a cyclobutyl group, a 1-methyl-cyclopropyl group, a 2-methyl-cyclopropyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-isopropyl-cyclopropyl group, a 2-isopropyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of the $C_{1-10}$ alkylene group include alkylene groups derived from the above alkyl groups.

Examples of the aryl group include $C_{6-20}$ aryl groups such as a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-mercaptophenyl group, an o-methoxyphenyl group, a p-methoxyphenyl group, a p-aminophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Examples of the alkenyl group include $C_{2-10}$ alkenyl groups such as an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethyl ethenyl group, a 1-methyl-1-propenyl group, a 1-methyl-2-propenyl group, a 1-pentenyl group, a 2-pentenyl group, a 3-pentenyl group, a 4-pentenyl group, a 1-n-propyl ethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-isopropyl ethenyl group, a 1,2-dimethyl-1-propenyl group, a 1,2-dimethyl-2-propenyl group, a 1-cyclopentenyl group, a 2-cyclopentenyl, a 3-cyclopentenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butyl ethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-sec-butyl ethenyl group, a 1,3-dimethyl-1-butenyl group, a 1,3-dimethyl-2-butenyl group, a 1,3-dimethyl-3-butenyl group, a 1-isobutyl ethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-isopropyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-tert-butyl ethenyl group, a 1-methyl-1-ethyl-2-propenyl group, a 1-ethyl-2-methyl-1-propenyl group, a 1-ethyl-2-methyl-2-propenyl group, a 1-isopropyl-1-propenyl group, a 1-isopropyl-2-propenyl, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group, and a 3-cyclohexenyl group.

The aralkyl group is an alkyl group substituted with an aryl group and examples of the aralkyl group include $C_{1-10}$ alkyl substituted with a phenyl such as, as specific examples thereof, a benzyl group, an ethylphenyl group, a propylphenyl group, and a butylphenyl group.

Examples thereof also include organic groups in which the groups mentioned above are substituted with a halogen atom such as a fluorine atom, a chlorine atom, a bromine atom, and an iodine atom.

Examples of the organic group having an epoxy group include a glycidoxymethyl group, a glycidoxyethyl group, a glycidoxypropyl group, a glycidoxybutyl group, and an epoxycyclohexyl group.

Examples of the organic group having an acryloyl group include an acryloylmethyl group, an acryloylethyl group, and an acryloylpropyl group.

Examples of the organic group having a methacryloyl group include a methacryloylmethyl group, a methacryloylethyl group, and a methacryloylpropyl group.

Examples of the organic group having a mercapto group include an ethylmercapto group, a butylmercapto group, a hexylmercapto group, and an octylmercapto group.

Examples of the organic group having a cyano group include a cyanoethyl group and a cyanopropyl group.

Examples of the organic group having a sulfonyl group include a methylsulfonyl group, an allylsulfonyl group, and a phenylsulfonyl group.

Examples of the $C_{1-20}$ alkoxy group as $R^3$ in Formula (1) include $C_{1-20}$ alkoxy groups having a linear, branched, or cyclic alkyl moiety. Examples of the linear or branched alkoxy group include a methoxy group, an ethoxy group, an n-propoxy group, an isopropoxy group, an n-butoxy group, an isobutoxy group, a sec-butoxy group, a tert-butoxy group, an n-pentyloxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, an n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2-trimethyl-n-propoxy group, a 1-ethyl-1-methyl-n-propoxy group, and a 1-ethyl-2-methyl-n-propoxy group. Examples of the cyclic alkoxy group include a cyclopropoxy group, a cyclobutoxy group, a 1-methyl-cyclopropoxy group, a 2-methyl-cyclopropoxy group, a cyclopentyloxy group, a 1-methyl-cyclobutoxy group, a 2-methyl-cyclobutoxy group, a 3-methyl-cyclobutoxy group, a 1,2-dimethyl-cyclopropoxy group, a 2,3-dimethyl-cyclopropoxy group, a 1-ethyl-cyclopropoxy group, a 2-ethyl-cyclopropoxy group, a cyclohexyloxy group, a 1-methyl-cyclopentyloxy group, a 2-methyl-cyclopentyloxy group, a 3-methyl-cyclopentyloxy group, a 1-ethyl-cyclobutoxy group, a 2-ethyl-cyclobutoxy group, a 3-ethyl-cyclobutoxy group, a 1,2-dimethyl-cyclobutoxy group, a 1,3-dimethyl-cyclobutoxy group, a 2,2-dimethyl-cyclobutoxy group, a 2,3-dimethyl-cyclobutoxy group, a 2,4-dimethyl-cyclobutoxy group, a 3,3-dimethyl-cyclobutoxy group, a 1-n-propyl-cyclopropoxy group, a 2-n-propyl-cyclopropoxy group, a 1-isopropyl-cyclopropoxy group, a 2-isopropyl-cyclopropoxy group, a 1,2,2-trimethyl-cyclopropoxy group, a 1,2,3-trimethyl-cyclopropoxy group, a 2,2,3-trimethyl-cyclopropoxy group, a 1-ethyl-2-methyl-cyclopropoxy group, a 2-ethyl-1-methyl-cyclopropoxy group, a 2-ethyl-2-methyl-cyclopropoxy group, and a 2-ethyl-3-methyl-cyclopropoxy group.

Examples of the $C_{2-20}$ acyloxy group as $R^3$ in Formula (1) include a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a tert-butylcarbonyloxy group, an n-pentylcarbonyloxy group, a 1-methyl-n-butylcarbonyloxy group, a 2-methyl-n-butylcarbonyloxy group, a 3-methyl-n-butylcarbonyloxy group, a 1,1-dimethyl-n-propylcarbonyloxy group, a 1,2-dimethyl-n-propylcarbonyloxy group, a 2,2-dimethyl-n-propylcarbonyloxy group, a 1-ethyl-n-propylcarbonyloxy group, an n-hexylcarbonyloxy group, a 1-methyl-n-pentylcarbonyloxy group, a 2-methyl-n-pentylcarbonyloxy group, a 3-methyl-n-pentylcarbonyloxy group, a 4-methyl-n-pentylcarbonyloxy group, a 1,1-dimethyl-n-butylcarbonyloxy group, a 1,2-dimethyl-n-butylcarbonyloxy group, a 1,3-dimethyl-n-butylcarbonyloxy group, a 2,2-dimethyl-n-butylcarbonyloxy group, a 2,3-dimethyl-n-butylcarbonyloxy group, a 3,3-dimethyl-n-butylcarbonyloxy group, a 1-ethyl-n-butylcarbonyloxy group, a 2-ethyl-n-butylcarbonyloxy group, a 1,1,2-trimethyl-n-propylcarbonyloxy group, a 1,2,2-trimethyl-n-propylcarbonyloxy group, a 1-ethyl-1-methyl-n-propylcarbonyloxy group, a 1-ethyl-2-methyl-n-propylcarbonyloxy group, a phenylcarbonyloxy group, and a tosylcarbonyloxy group.

Examples of the halogen group as $R^3$ in Formula (1) include a fluorine atom, a chlorine atom, a bromine atom, and an iodine atom.

Examples of the hydrolyzable organosilane of Formula (1) include organosilanes of Formulae below.

Formula (1-1)
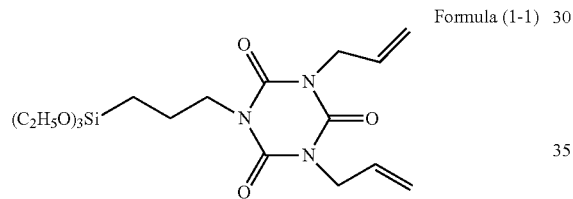

Formula (1-2)

Formula (1-3)
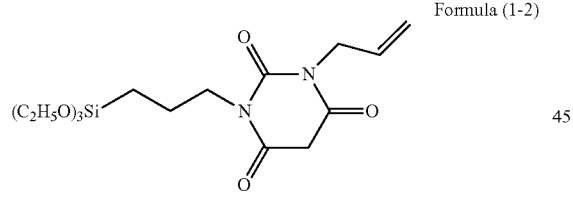

Formula (1-4)
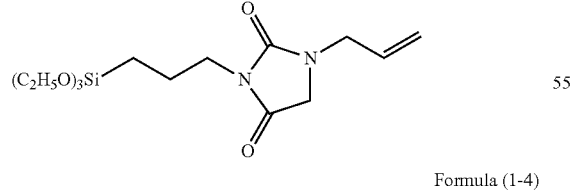

Formula (1-5)
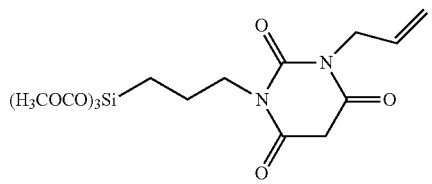

Formula (1-6)
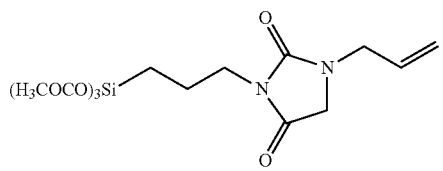

Formula (1-7)
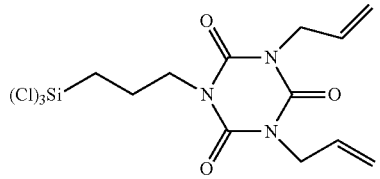

Formula (1-8)
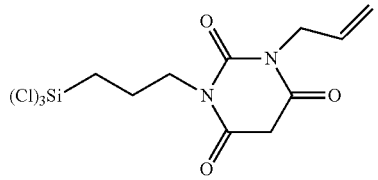

Formula (1-9)
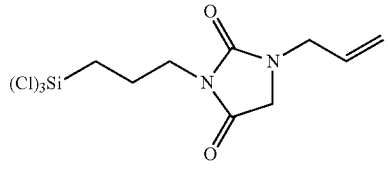

Formula (1-10)
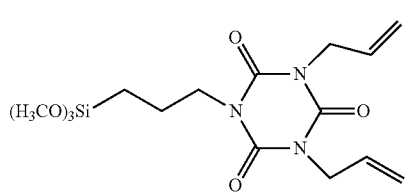

Formula (1-11)
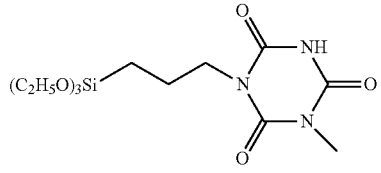

Formula (1-12)
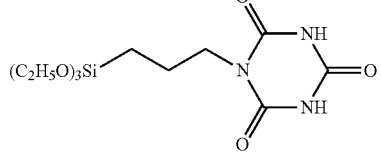

Formula (1-13)
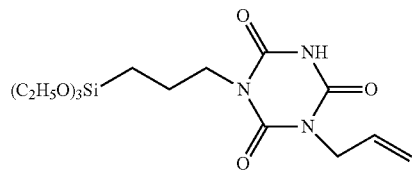
Formula (1-14)
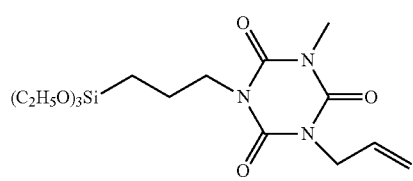
Formula (1-15)
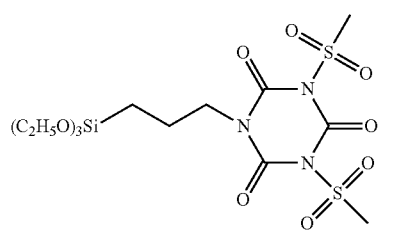
Formula (1-16)
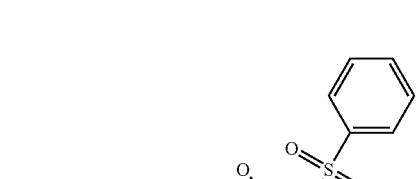
Formula (1-17)
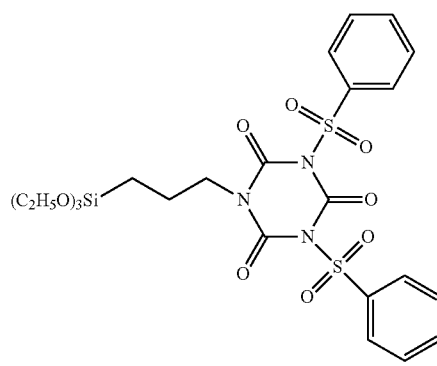
Formula (1-18)
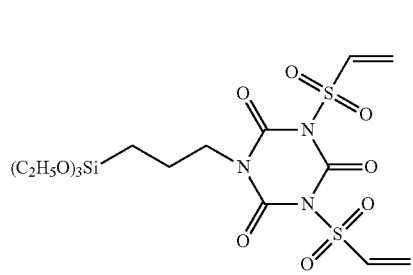
Formula (1-19)
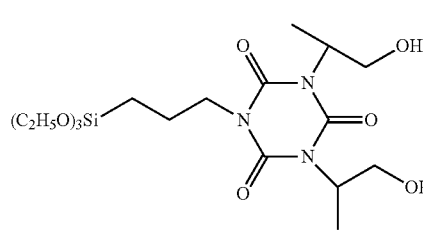
Formula (1-20)
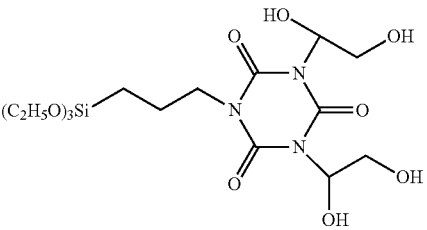
Formula (1-21)
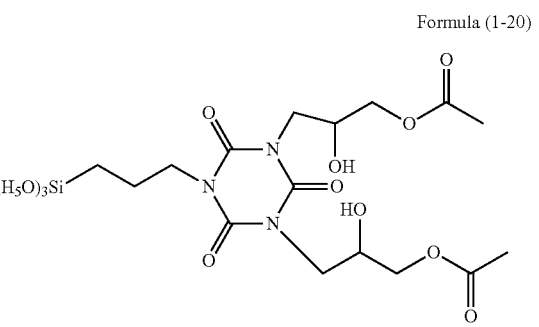
Formula (1-22)
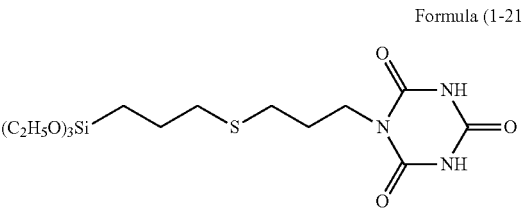
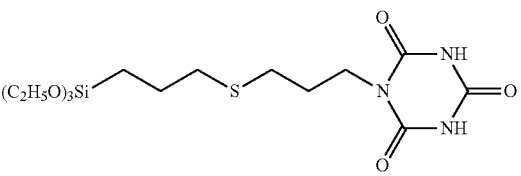
Formula (1-23)
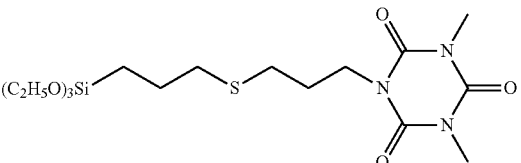
Formula (1-24)
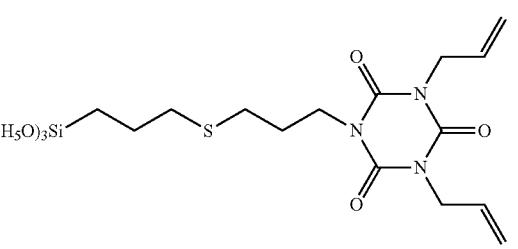
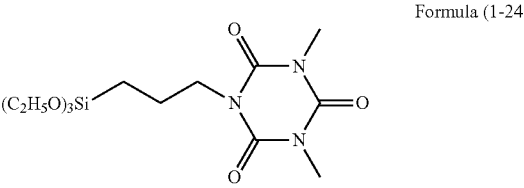
Formula (1-25)
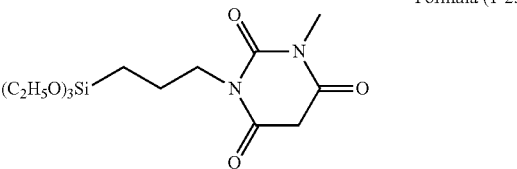

Formula (1-26)

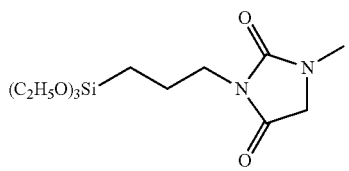

Formula (1-27)

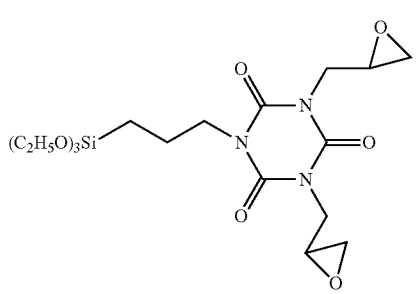

Formula (1-28)

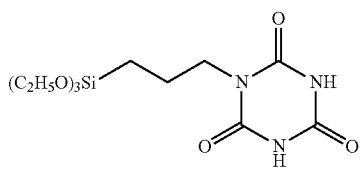

Formula (1-29)

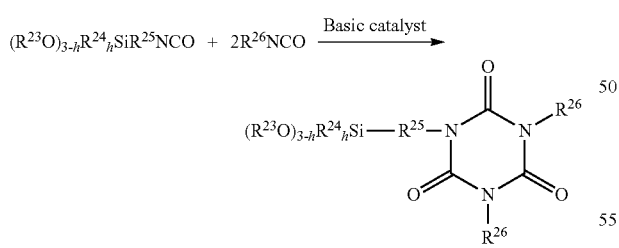

As the hydrolyzable organosilane of Formula (1), commercial products may be used. However, the hydrolyzable organosilane can be synthesized.

For example, an alkoxysilane having dialkenylcyanuric acid can also be obtained by reacting an isocyanuric acid ester in the presence of a basic catalyst.

$$(R^{23}O)_{3-h}R^{24}{}_hSiR^{25}NCO + 2R^{26}NCO \xrightarrow{\text{Basic catalyst}}$$

In the above reaction, $R^{23}$ in a silicon-containing isocyanuric acid ester is a $C_{1-6}$ alkyl group; $R^{24}$ is a $C_{1-6}$ alkyl group or a phenyl group; $R^{25}$ is a $C_{2-4}$ alkylene group; h is an integer of 0, 1, or 2; and $R^{26}$ in another isocyanuric acid ester is a $C_{2-4}$ alkenyl group. The basic catalyst is represented as $MOR^{27}$, where $R^{27}$ is a hydrogen atom or an alkyl group such as a methyl group and an ethyl group and M is an alkali metal such as lithium, sodium, and potassium. The basic catalyst may be blended in the reaction mixture in a content of 0.1 to 5 parts by mass, relative to 100 parts by mass of an isocyanuric acid ester mixture. Examples of this alkyl group or alkylene group include functional groups having the number of carbon atoms corresponding to the number of carbon atoms of the above exemplified alkyl groups or alkylene groups. Although the reaction may be effected without solvent, the reaction may also be effected in a non-polar solvent such as benzene, hexane, toluene, and heptane. The reaction may be effected at a reaction temperature in a range of 60 to 150° C. By this method, there can be synthesized (3-triethoxysilylpropyl)diallylisocyanurate or the like. This alkoxysilane can be synthesized according to a method described in Japanese Patent Application Publication No. JP-A-6-1796.

For example, (3-triethoxysilylpropyl) isocyanurate can be synthesized by the method set forth below.

Into a 300 mL three-neck flask, 30.0 g of monoallyl isocyanurate, 36.42 g of triethoxysilane, 0.09 g of chloroplatinic (VI) acid hydrate, and 100 mL of toluene are charged and the reaction is effected at 100° C. for 6 hours. Then, toluene and triethoxysilane contained excessively are removed by an evaporator. Then, extraction of the resultant reaction mixture with 100 mL of dichloromethane, 50 mL×3 of distilled water is performed and the organic phase is dehydrated over magnesium sulfate. Then, from the organic phase, dichloromethane is removed by an evaporator, so that the product can be obtained.

By changing monoallyl isocyanurate to dimethylmonoallyl isocyanurate or diglycidylmonoallyl isocyanurate, (3-triethoxysilylpropyl)dimethyl isocyanurate or (3-triethoxysilylpropyl)diglycidyl isocyanurate can be synthesized.

For example, the below-described alkoxysilane having dialkyl cyanuric acid can be synthesized by the method set forth below.

Into a 300 mL three-neck flask, 10.00 g of dimethylmonoallyl isocyanurate, 24.18 g of (3-mercaptopropyl)triethoxysilane, 0.21 g of azobisisobutylonitrile, and 100 mL of methyl ethyl ketone are charged and the reaction is effected at 95° C. for 6 hours. Then, methyl ethyl ketone is removed by an evaporator. Then, extraction of the resultant reaction mixture with 100 mL of dichloromethane, 50 mL×3 of distilled water is performed and the organic phase is dehydrated over magnesium sulfate. Then, from the organic phase, dichloromethane is removed by an evaporator, so that the crude product can be obtained. The obtained crude product is purified by distillation, so that the compound can be obtained.

In the present invention, a hydrolyzable organosilane of Formula (1) can be used in combination with a hydrolyzable organosilane of Formula (6).

That is, a hydrolyzable organosilane of Formula (1), a hydrolysis product thereof, or a hydrolysis-condensation product thereof can be used in combination with a hydrolyzable silane of Formula (6), a hydrolysis product thereof, or a hydrolysis-condensation product thereof.

The ratio between a hydrolyzable organosilane of Formula (1) and a hydrolyzable silane of Formula (6) in a molar ratio can be used in a range of 1:0 to 1:200. In order to obtain an advantageous resist shape, the ratio between a hydrolyzable organosilane of Formula (1) and a hydrolyzable silane of Formula (6) in a molar ratio can be used in a range of 1:199 to 1:2.

These are preferably used as a hydrolysis-condensation product (polymer of polyorganosiloxane) and a hydrolysis-condensation product (polymer of polyorganosiloxane) of a hydrolyzable organosilane of Formula (1) and a hydrolyzable silane of Formula (6) is preferably used.

$R^{11}$ in a hydrolyzable silane of Formula (6) is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, a sulfonyl group, a sulfide bond, an ether bond, an ester bond, a sulfonamide group, or a cyano group, or a combination thereof, and is bonded to a silicon atom through a Si—C bond; $R^{12}$ is an alkoxy group, an acyloxy group, or a halogen group; and c is an integer of 0 to 3.

Examples of the alkyl group, the aryl group, the aralkyl group, the halogenated alkyl group, the halogenated aryl group, the halogenated aralkyl group, the alkenyl group, or the organic group having an epoxy group, an acryloyl group, a methacryloyl group, a mercapto group, a sulfonamide group, or a cyano group of $R^{11}$ in Formula (6) and further, the alkoxy group, the acyloxy group, or the halogen group contained in the hydrolyzable group of $R^{12}$ include groups exemplified above with respect to Formula (1).

Examples of the sulfonamido group include a phenylsulfonamido group and a methylsulfonamido group Examples of the hydrolyzable silane of Formula (6) include tetramethoxysilane, tetrachlorosilane, tetraacetoxysilane, tetraethoxysilane, tetra n-propoxysilane, tetraisopropoxysilane, tetra n-butoxysilane, tetraacetoxysilane, methyltrimethoxysilane, methyltrichlorosilane, methyltriacetoxysilane, methyltripropoxysilane, methyltriacetoxysilane, methyltributoxysilane, methyltripropoxysilane, methyltriamyloxysilane, methyltriphenoxysilane, methyltribenzyloxysilane, methyltriphenethyloxysilane, glycidoxymethyltrimethoxysilane, glycidoxymethyltriethoxysilane, α-glycidoxyethyltrimethoxysilane, α-glycidoxyethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-glycidoxypropyltrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltributoxysilane, γ-glycidoxypropyltriphenoxysilane, α-glycidoxybutyltrimethoxysilane, α-glycidoxybutyltriethoxysilane, β-glycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, β-(3,4-epoxycyclohexyl)ethyltrimethoxysilane, β-(3,4-epoxycyclohexyl) ethyltriethoxysilane, β-(3,4-epoxycyclohexyl)ethyltripropoxysilane, β-(3,4-epoxycyclohexyethyltributoxysilane, β-(3,4-epoxycyclohexyl)ethyltriphenoxysilane, γ-(3,4-epoxycyclohexyl)propyltrimethoxysilane, γ-(3,4-epoxycyclohexyl)propyltriethoxysilane, δ-(3,4-epoxycyclohexyl) butyltrimethoxysilane, δ-(3,4-epoxycyclohexyl) butyltriethoxysilane, glycidoxymethylmethyldimethoxysilane, glycidoxymethylmethyldiethoxysilane, α-glycidoxyethylmethyldimethoxysilane, α-glycidoxyethylmethyldiethoxysilane, β-glycidoxyethylmethyldimethoxysilane, β-glycidoxyethylethyldimethoxysilane, α-glycidoxypropylmethyldimethoxysilane, α-glycidoxypropylmethyldiethoxysilane, β-glycidoxypropylmethyldimethoxysilane, β-glycidoxypropylethyldimethoxysilane, γ-glycidoxypropylmethyldimethoxysilane, γ-glycidoxypropylmethyldiethoxysilane, γ-glycidoxypropylmethyldipropoxysilane, γ-glycidoxypropylmethyldibutoxysilane, γ-glycidoxypropylmethyldiphenoxysilane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, ethyltrimethoxysilane, ethyltriethoxysilane, vinyltrimethoxysilane, vinyltrichlorosilane, vinyltriacetoxysilane, vinyltriethoxysilane, vinyltriacetoxysilane, phenyltrimethoxysilane, phenyltrichlorosilane, phenyltriacetoxysilane, phenyltriethoxysilane, phenyltriacetoxysilane, γ-chloropropyltrimethoxysilane, γ-chloropropyltriethoxysilane, γ-chloropropyltriacetoxysilane, 3,3,3-trifluoropropyltrimethoxysilane, γ-methacryloxypropyltrimethoxysilane, γ-mercaptopropyltrimethoxysilane, γ-mercaptopropyltriethoxysilane, β-cyanoethyltriethoxysilane, chloromethyltrimethoxysilane, chloromethyltriethoxysilane, dimethyldimethoxysilane, phenylmethyldimethoxysilane, dimethyldiethoxysilane, phenylmethyldiethoxysilane, γ-chloropropylmethyldimethoxysilane, γ-chloropropylmethyldiethoxysilane, dimethyldiacetoxysilane, γ-methacryloxypropylmethyldimethoxysilane, γ-methacryloxypropylmethyldiethoxysilane, γ-mercaptopropylmethyldimethoxysilane, γ-mercaptomethyldiethoxysilane, methylvinyldimethoxysilane, methylvinyldiethoxysilane, phenylsulfonylaminopropyltriethoxysilane, methylsulfonylaminopropyltriethoxysilane, phenylsulfonylaminopropyltrimethoxysilane, methylsulfonylaminopropyltrimethoxysilane, N-[3-(triethoxysilyl)propyl]benzenesulfonamide, N-[3-(triethoxysilyl)propyl]methanesulfonamide, N-[3-(triethoxysilyl)propyl]allylsulfonamide, and N-[3-(triethoxysilyl)propyl]vinylsulfonamide.

The hydrolyzable silane of Formula (6) includes the compounds below. Here, $R^{12}$ in the compounds is the same as $R^{12}$ in Formula (6).

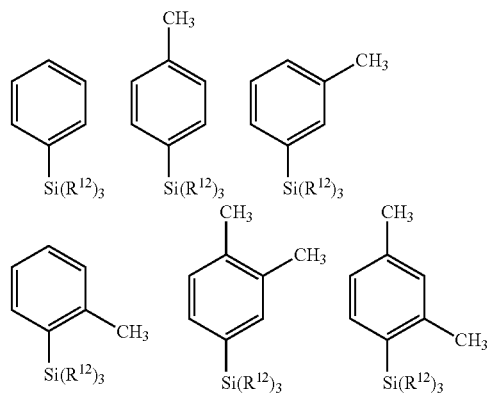

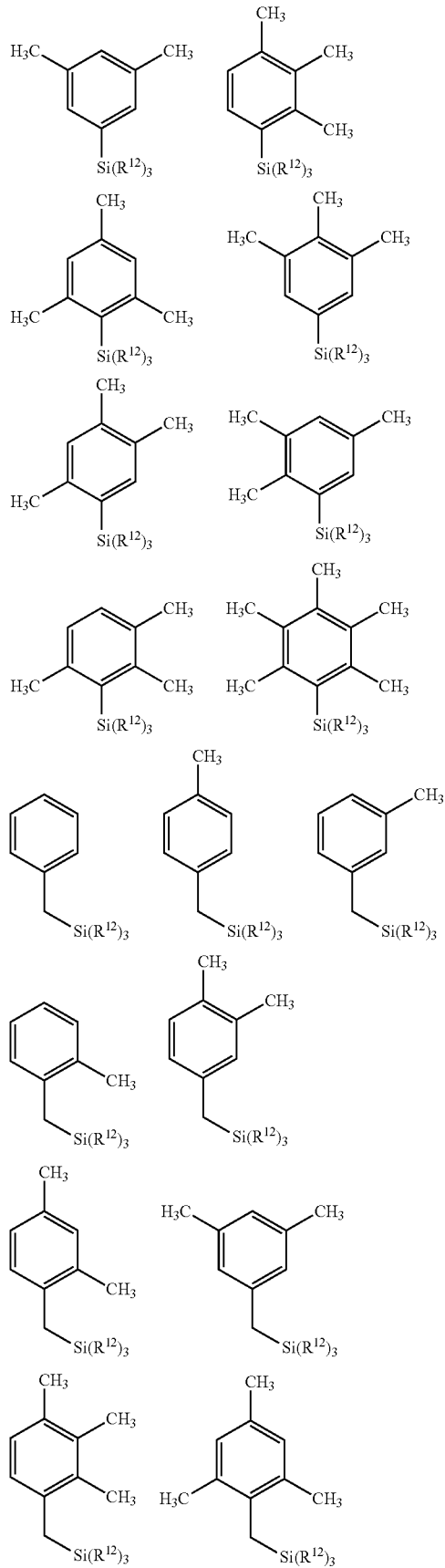
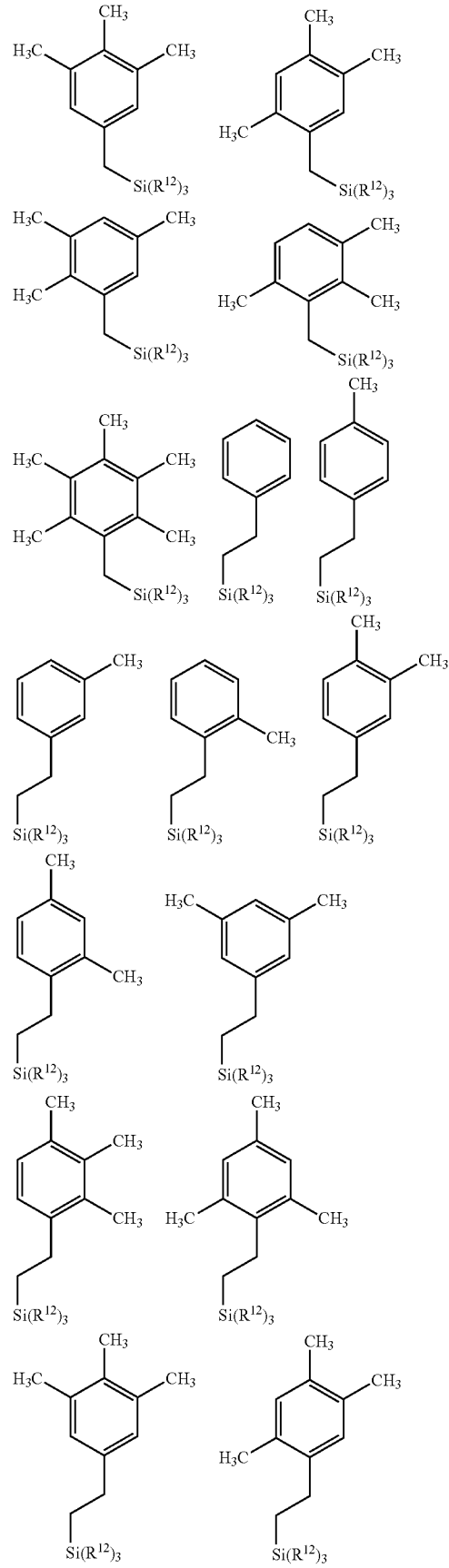

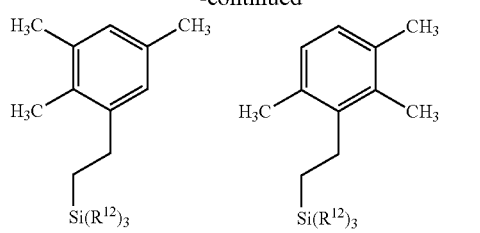
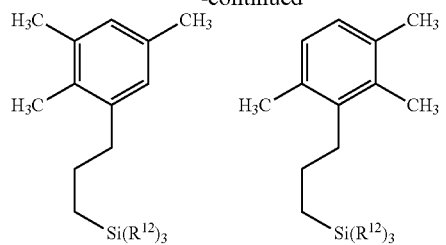
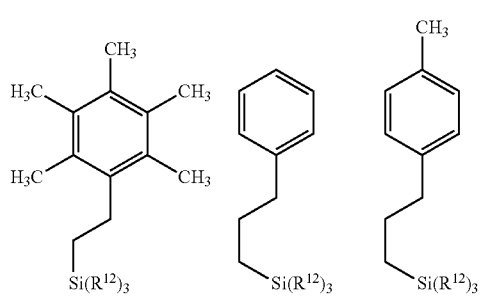
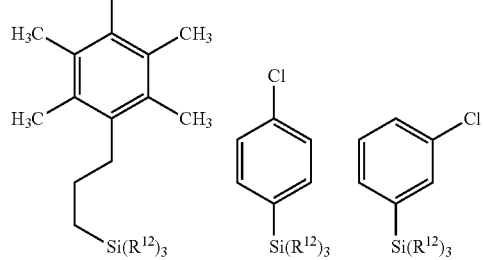
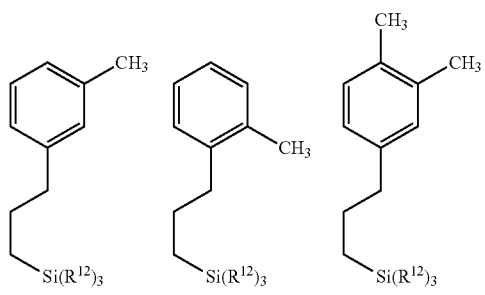
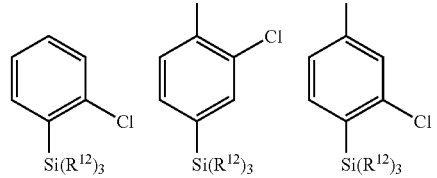
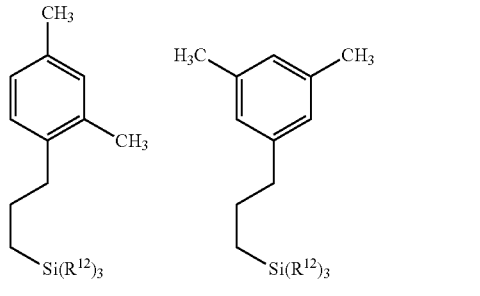
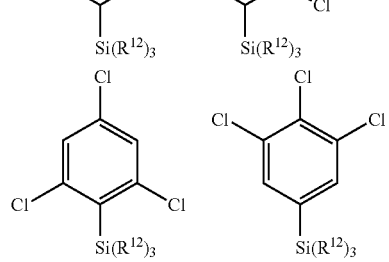
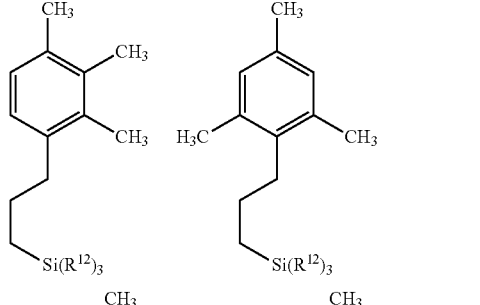
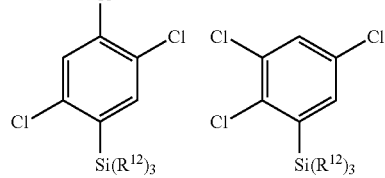
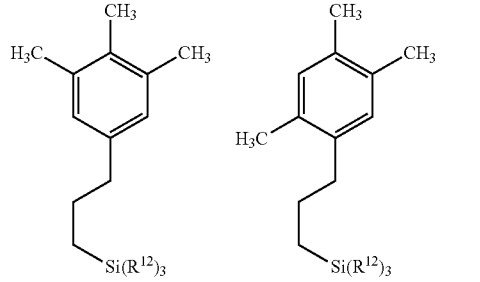
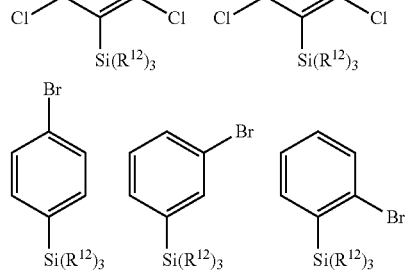

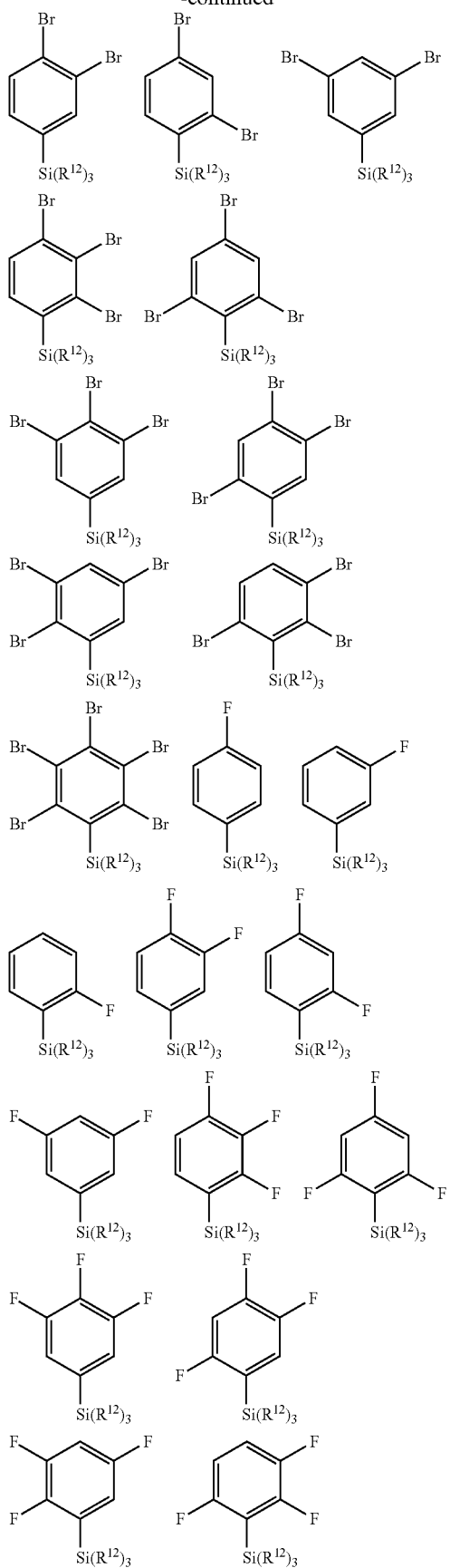

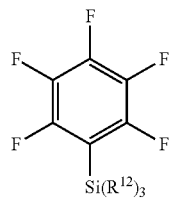

In the present invention, the silane compound may further include a hydrolyzable organosilane of Formula (7) having a cyclic amino group, a hydrolysis product thereof, or a hydrolysis-condensation product thereof.

The hydrolyzable organosilane having a cyclic amino group can be used in such a range that the amount of the silicon atom in the hydrolyzable organosilane becomes less than 1% by mole, preferably 0.99 to 0.01% by mole, based on the number of moles of the silicon atom of the whole silane compound in the composition.

In Formula (7), $R^{13}$ is a cyclic amine or an organic group containing the same and is bonded to a silicon atom through a Si—N bond or a Si—C bond. In Formula (7), $R^{14}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond. In Formula (7), $R^{15}$ is an alkoxy group, an acyloxy group, or a halogen group. d is an integer of 1 or 2 and e is an integer of 0 or 1, where d+e is an integer of 1 or 2. Examples of the alkyl group, the aryl group, the aralkyl group, the halogenated aralkyl group, the alkoxy group, the alkenyl group, the acyloxy group, and the halogen group include the groups individually exemplified above.

Specific examples of the hydrolyzable organosilane of Formula (7) include the compounds below.

Formula (A-1)

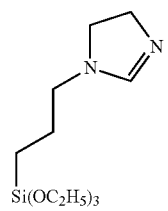

Formula (A-2)

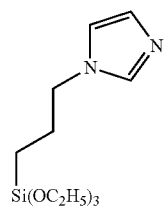

Formula (A-3)

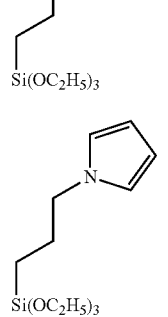

-continued
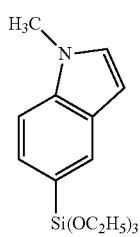
Formula (A-4)
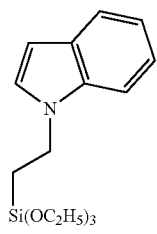
Formula (A-5)
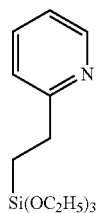
Formula (A-6)
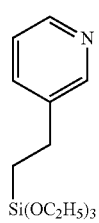
Formula (A-7)
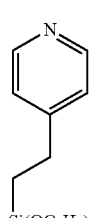
Formula (A-8)
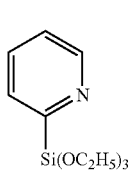
Formula (A-9)
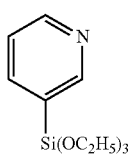
Formula (A-10)
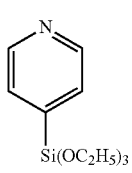
Formula (A-11)
-continued
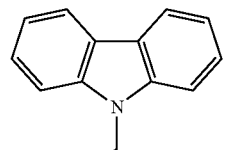
Formula (A-12)
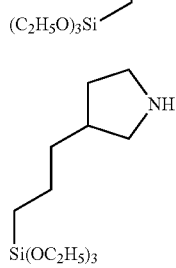
Formula (A-13)
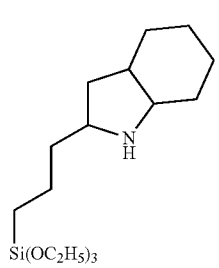
Formula (A-14)
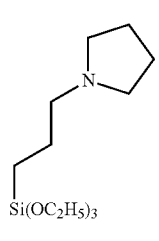
Formula (A-15)
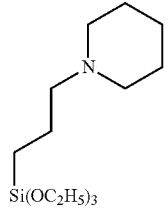
Formula (A-16)
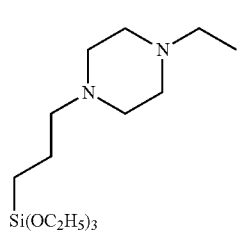
Formula (A-17)
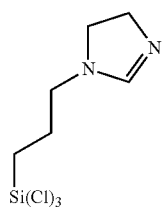
Formula (A-18)

-continued

Formula (A-19)

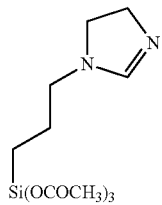

In the present invention, the silane compound may further include a hydrolyzable organosilane of Formula (8) having an alkoxyphenyl group or an acyloxyphenyl group, a hydrolysis product thereof, or a hydrolysis-condensation product thereof.

The hydrolyzable organosilane having an alkoxyphenyl group or an acyloxyphenyl group can be used in such a range that the amount of the silicon atom in the hydrolyzable organosilane becomes less than 1% by mole, preferably 0.99 to 0.01% by mole, based on the number of moles of the silicon atom of the whole silane compound.

In Formula (8), $R^{16}$ is an alkoxyphenyl group, an acyloxyphenyl group, or an organic group containing these groups and is bonded to a silicon atom through a Si—C bond. In Formula (8), $R^{17}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond. In Formula (8), $R^{18}$ is an alkoxy group, an acyloxy group, or a halogen group. In Formula (8), $R^{16}$ and $R^{17}$ can also form together a ring. f is an integer of 1 or 2 and g is an integer of 0 or 1, where f+g is an integer of 1 or 2. Examples of the alkyl group, the aryl group, the aralkyl group, the halogenated aralkyl group, the alkoxy group, the alkenyl group, the acyloxy group, and the halogen group include the groups individually exemplified above.

The hydrolyzable organosilane of Formula (8) includes the compounds below. Here, $R^{18}$ in the compounds is the same as $R^{18}$ in Formula (8).

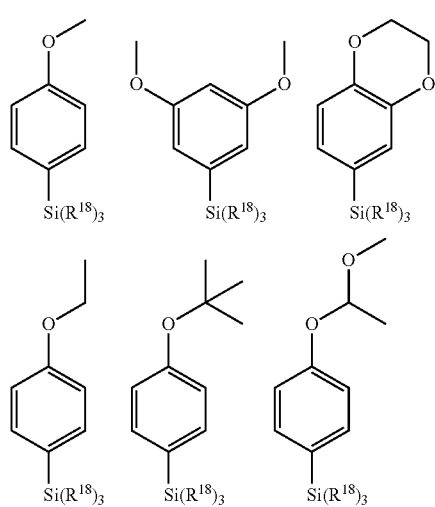

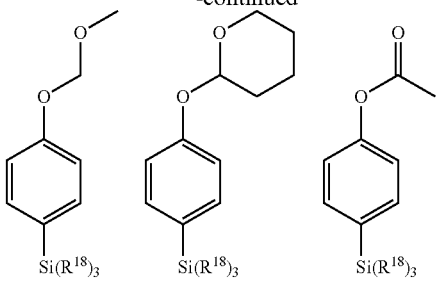

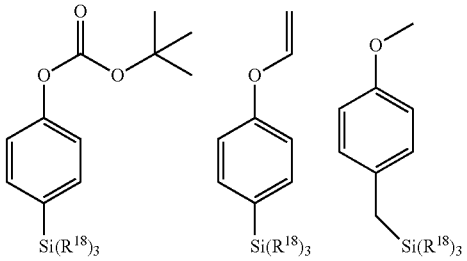

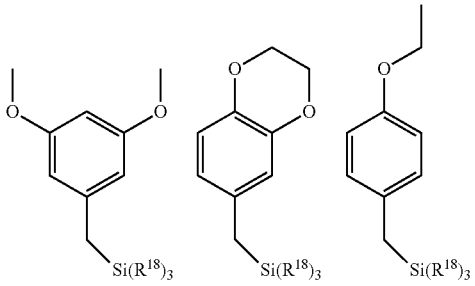

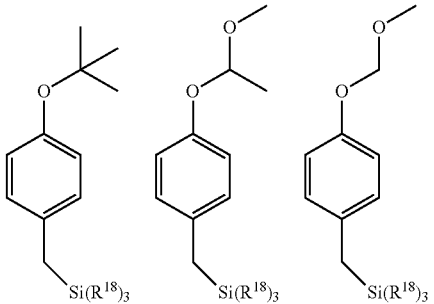

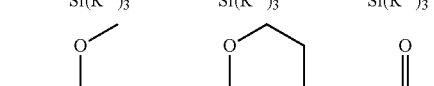

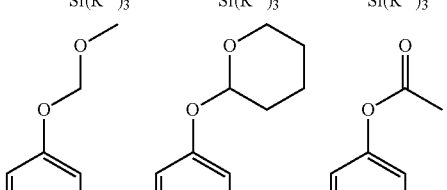

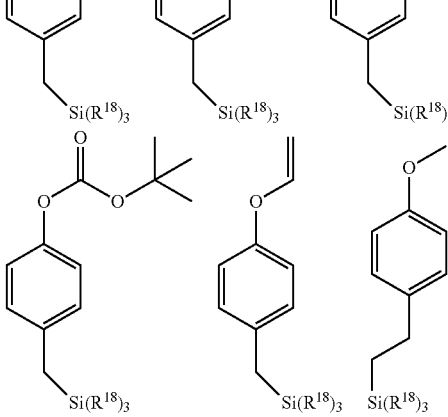

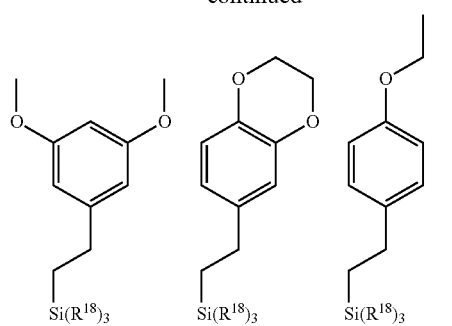
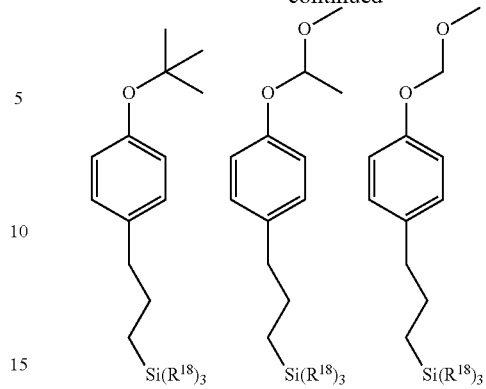
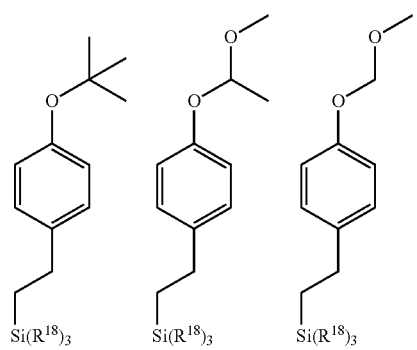
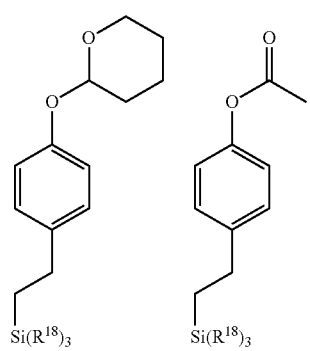
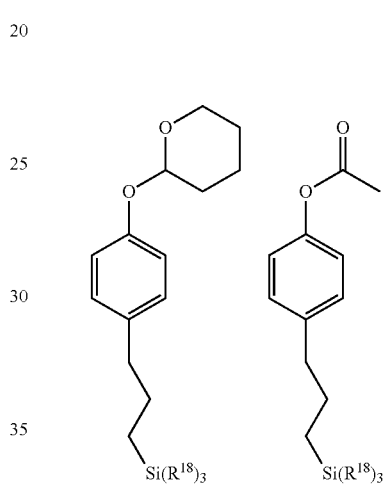
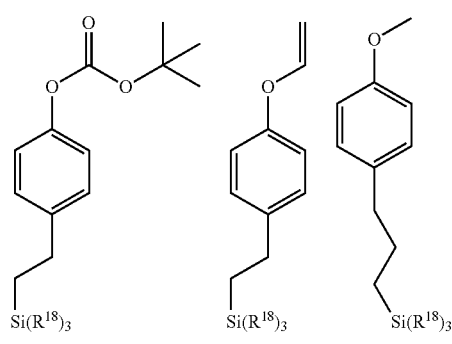
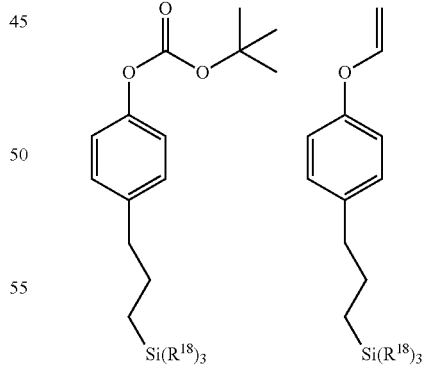
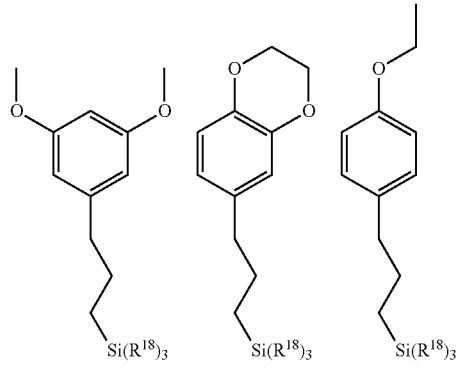
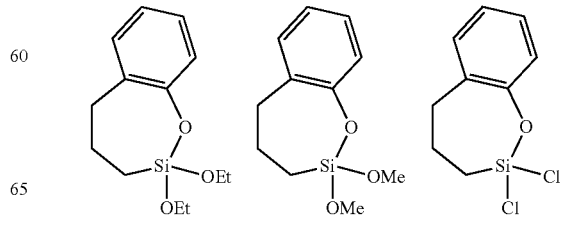

Specific examples of the hydrolyzable organosilane of Formula (8) include the compounds below.
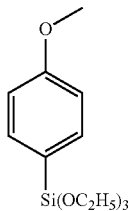
Formula (B-1)
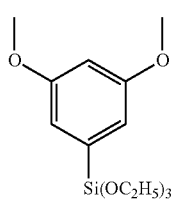
Formula (B-2)
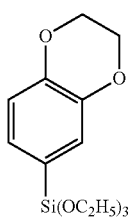
Formula (B-3)
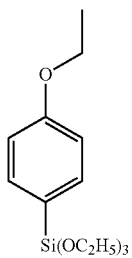
Formula (B-4)
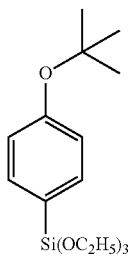
Formula (B-5)
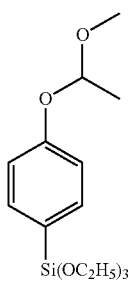
Formula (B-6)
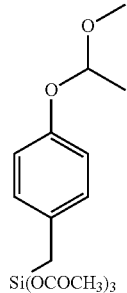
Formula (B-7)
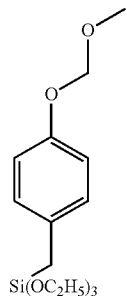
Formula (B-8)
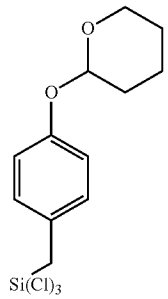
Formula (B-9)
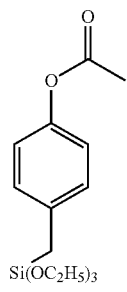
Formula (B-10)
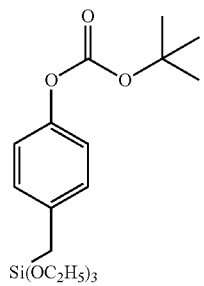
Formula (B-11)

Formula (B-12)
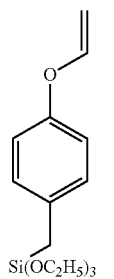
Formula (B-13)
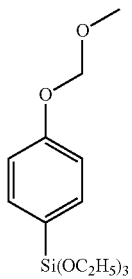
Formula (B-14)
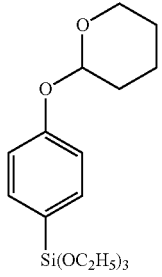
Formula (B-15)
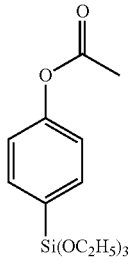
Formula (B-16)
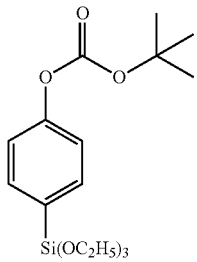
Formula (B-17)
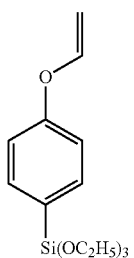
Formula (B-18)
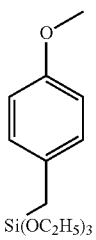
Formula (B-19)
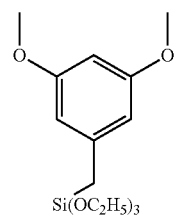
Formula (B-20)
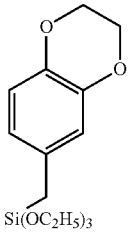
Formula (B-21)
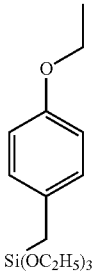
Formula (B-22)
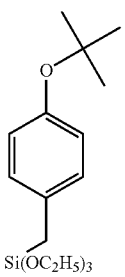
Formula (B-23)
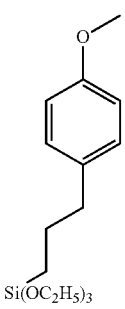

Formula (B-24)
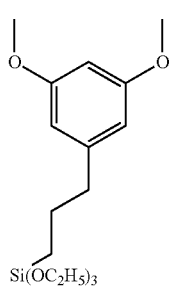
Formula (B-25)
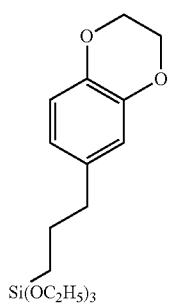
Formula (B-26)
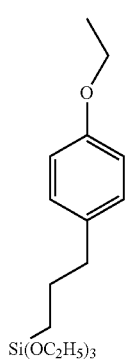
Formula (B-27)
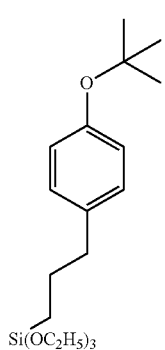
Formula (B-28)
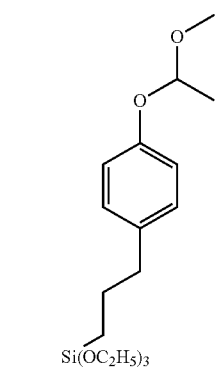
Formula (B-29)
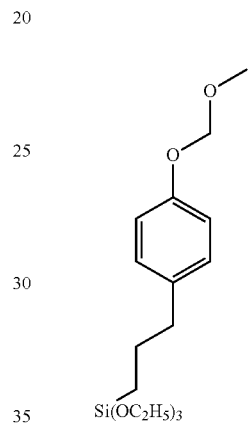
Formula (B-30)
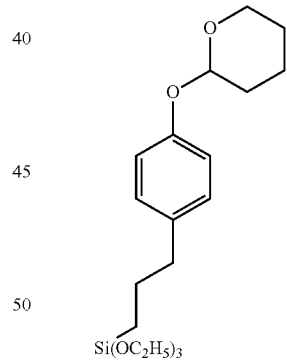
Formula (B-31)
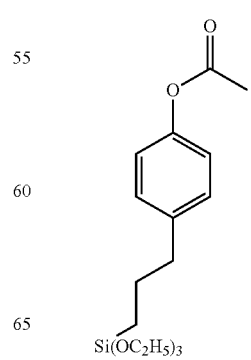

Formula (B-32)
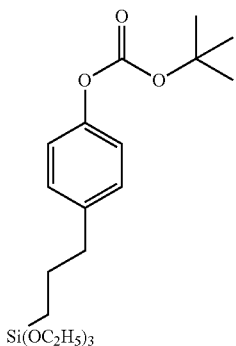

Formula (B-33)
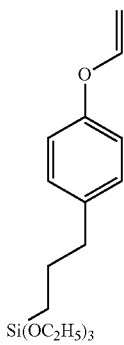

Formula (B-34)
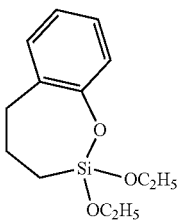

Formula (B-35)
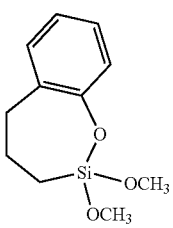

Formula (B-36)
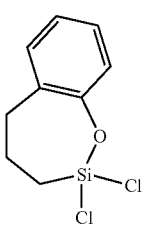

Formula (B-37)
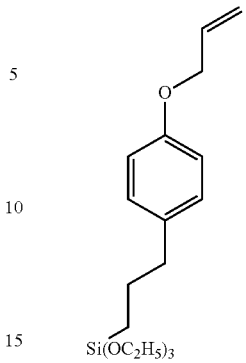

Formula (B-38)
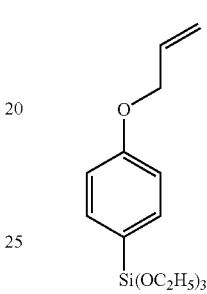

Formula (B-39)
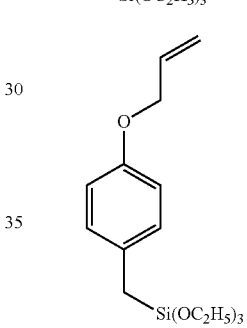

One aspect of the present invention provides a composition containing as the silane compound, at least a hydrolyzable organosilane of Formula (1) that is a hydrolyzable organosilane containing diallyl isocyanurate and a hydrolyzable silane of Formula (6) that is a tetraalkoxysilane.

One aspect of the present invention provides a composition containing as the silane compound, at least a hydrolyzable organosilane of Formula (1) that is a silane compound containing diallyl isocyanurate and a hydrolyzable organosilane of Formula (6) that is a tetraalkoxysilane and an unsubstituted or substituted phenyltrialkoxysilane.

One aspect of the present invention provides a composition containing as the silane compound, at least a hydrolyzable organosilane of Formula (1) that is a hydrolyzable organosilane containing diallyl isocyanurate, a hydrolyzable silane of Formula (6) that is a tetraalkoxysilane, and a hydrolyzable organosilane of Formula (8) that is a hydrolyzable organosilane containing an alkoxyphenyl group.

One aspect of the present invention provides a composition containing as the silane compound, at least a hydrolyzable organosilane of Formula (1) that is a silane compound containing diallyl isocyanurate, a hydrolyzable silane of Formula (6) that is a tetraalkoxysilane and an unsubstituted or substituted phenyltrialkoxysilane, and a hydrolyzable organosilane of Formula (8) that is a hydrolyzable organosilane containing an alkoxyphenyl group.

Specific examples of the hydrolysis-condensation product of a hydrolyzable organosilane of Formula (1) with a hydrolyzable silane of Formula (6) include the compounds below.

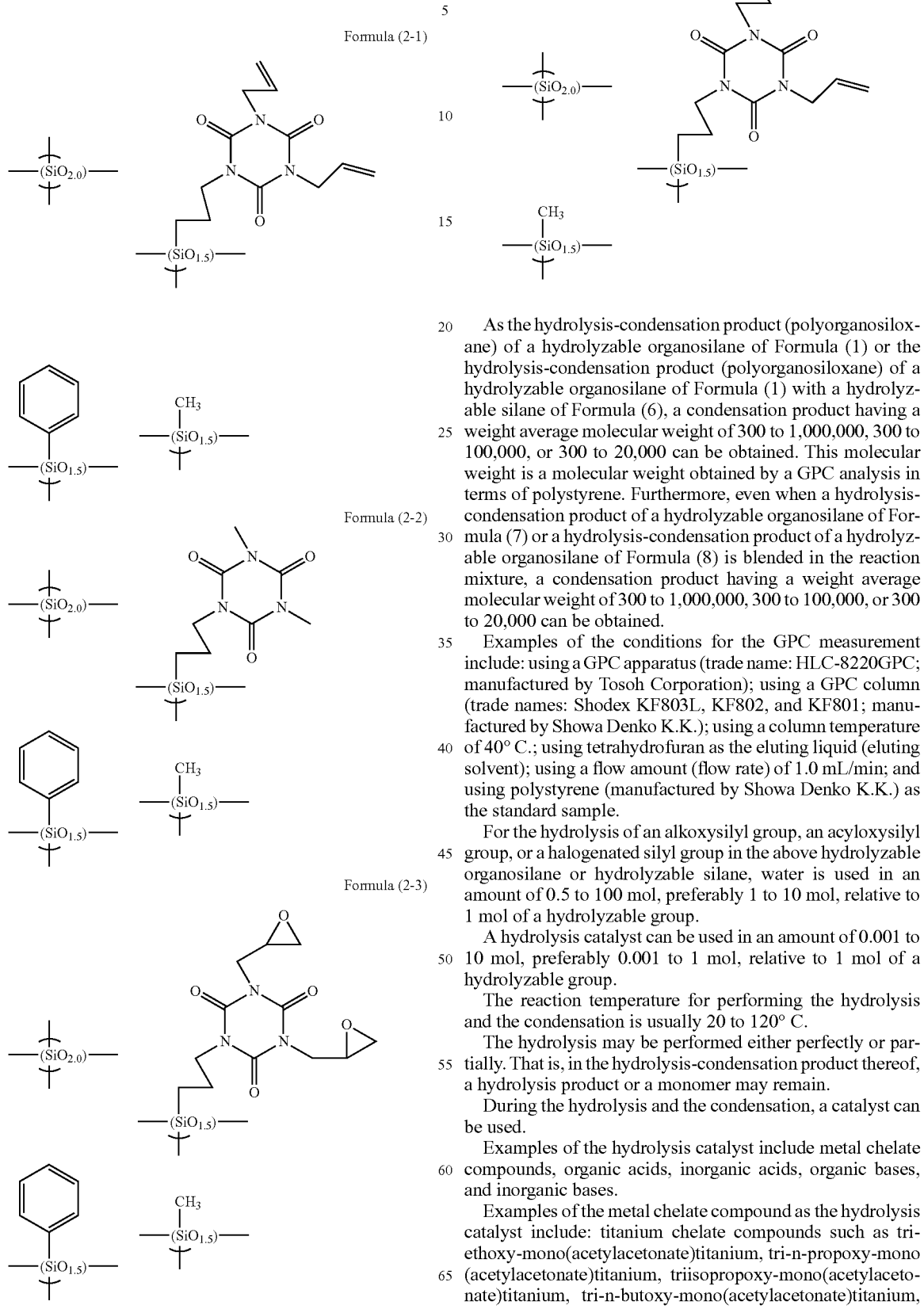

As the hydrolysis-condensation product (polyorganosiloxane) of a hydrolyzable organosilane of Formula (1) or the hydrolysis-condensation product (polyorganosiloxane) of a hydrolyzable organosilane of Formula (1) with a hydrolyzable silane of Formula (6), a condensation product having a weight average molecular weight of 300 to 1,000,000, 300 to 100,000, or 300 to 20,000 can be obtained. This molecular weight is a molecular weight obtained by a GPC analysis in terms of polystyrene. Furthermore, even when a hydrolysis-condensation product of a hydrolyzable organosilane of Formula (7) or a hydrolysis-condensation product of a hydrolyzable organosilane of Formula (8) is blended in the reaction mixture, a condensation product having a weight average molecular weight of 300 to 1,000,000, 300 to 100,000, or 300 to 20,000 can be obtained.

Examples of the conditions for the GPC measurement include: using a GPC apparatus (trade name: HLC-8220GPC; manufactured by Tosoh Corporation); using a GPC column (trade names: Shodex KF803L, KF802, and KF801; manufactured by Showa Denko K.K.); using a column temperature of 40° C.; using tetrahydrofuran as the eluting liquid (eluting solvent); using a flow amount (flow rate) of 1.0 mL/min; and using polystyrene (manufactured by Showa Denko K.K.) as the standard sample.

For the hydrolysis of an alkoxysilyl group, an acyloxysilyl group, or a halogenated silyl group in the above hydrolyzable organosilane or hydrolyzable silane, water is used in an amount of 0.5 to 100 mol, preferably 1 to 10 mol, relative to 1 mol of a hydrolyzable group.

A hydrolysis catalyst can be used in an amount of 0.001 to 10 mol, preferably 0.001 to 1 mol, relative to 1 mol of a hydrolyzable group.

The reaction temperature for performing the hydrolysis and the condensation is usually 20 to 120° C.

The hydrolysis may be performed either perfectly or partially. That is, in the hydrolysis-condensation product thereof, a hydrolysis product or a monomer may remain.

During the hydrolysis and the condensation, a catalyst can be used.

Examples of the hydrolysis catalyst include metal chelate compounds, organic acids, inorganic acids, organic bases, and inorganic bases.

Examples of the metal chelate compound as the hydrolysis catalyst include: titanium chelate compounds such as triethoxy-mono(acetylacetonate)titanium, tri-n-propoxy-mono(acetylacetonate)titanium, triisopropoxy-mono(acetylacetonate)titanium, tri-n-butoxy-mono(acetylacetonate)titanium, tri-sec-butoxy-mono(acetylacetonate)titanium, tri-tert-butoxy-mono(acetylacetonate)titanium, diethoxy-bis(acetylacetonate)titanium, di-n-propoxy-bis(acetylacetonate)titanium, di-isopropoxy-bis(acetylacetonate)titanium, di-n-butoxy-bis(acetylacetonate)titanium, di-sec-butoxy-bis(acetylacetonate)titanium, di-tert-butoxy-bis(acetylacetonate)titanium, monoethoxy-tris(acetylacetonate)titanium, mono-n-propoxy-tris(acetylacetonate)titanium, mono-isopropoxy-tris(acetylacetonate)titanium, mono-n-butoxy-tris(acetylacetonate)titanium, mono-sec-butoxy-tris(acetylacetonate)titanium, mono-tert-butoxy-tris(acetylacetonate)titanium, tetrakis(acetylacetonate)titanium, triethoxy-mono(ethylacetoacetate)titanium, tri-n-propoxy-mono(ethylacetoacetate)titanium, tri-isopropoxy-mono(ethylacetoacetate)titanium, tri-n-butoxy-mono(ethylacetoacetate)titanium, tri-sec-butoxy-mono(ethylacetoacetate)titanium, tri-tert-butoxy-mono(ethylacetoacetate)titanium, diethoxy-bis(ethylacetoacetate)titanium, di-n-propoxy-bis(ethylacetoacetate)titanium, di-isopropoxy-bis(ethylacetoacetate)titanium, di-n-butoxy-bis(ethylacetoacetate)titanium, di-sec-butoxy-bis(ethylacetoacetate)titanium, di-tert-butoxy-bis(ethylacetoacetate)titanium, monoethoxy-tris(ethylacetoacetate)titanium, mono-n-propoxy-tris(ethylacetoacetate)titanium, mono-isopropoxy-tris(ethylacetoacetate)titanium, mono-n-butoxy-tris(ethylacetoacetate)titanium, mono-sec-butoxy-tris(ethylacetoacetate)titanium, mono-tert-butoxy-tris(ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium; zirconium chelate compounds such as triethoxy-mono(acetylacetonate)zirconium, tri-n-propoxy-mono(acetylacetonate)zirconium, tri-isopropoxy-mono(acetylacetonate)zirconium, tri-n-butoxy-mono(acetylacetonate)zirconium, tri-sec-butoxy-mono(acetylacetonate)zirconium, tri-tert-butoxy-mono(acetylacetonate)zirconium, diethoxy-bis(acetylacetonate)zirconium, di-n-propoxy-bis(acetylacetonate)zirconium, di-isopropoxy-bis(acetylacetonate)zirconium, di-n-butoxy-bis(acetylacetonate)zirconium, di-sec-butoxy-bis(acetylacetonate)zirconium, di-tert-butoxy-bis(acetylacetonate)zirconium, monoethoxy-tris(acetylacetonate)zirconium, mono-n-propoxy-tris(acetylacetonate)zirconium, mono-isopropoxy-tris(acetylacetonate)zirconium, mono-n-butoxy-tris(acetylacetonate)zirconium, mono-sec-butoxy-tris(acetylacetonate)zirconium, mono-tert-butoxy-tris(acetylacetonate)zirconium, tetrakis(acetylacetonate)zirconium, triethoxy-mono(ethylacetoacetate)zirconium, tri-n-propoxy-mono(ethylacetoacetate)zirconium, tri-isopropoxy-mono(ethylacetoacetate)zirconium, tri-n-butoxy-mono(ethylacetoacetate)zirconium, tri-sec-butoxy-mono(ethylacetoacetate)zirconium, tri-tert-butoxy-mono(ethylacetoacetate)zirconium, diethoxy-bis(ethylacetoacetate)zirconium, di-n-propoxy-bis(ethylacetoacetate)zirconium, di-isopropoxy-bis(ethylacetoacetate)zirconium, di-n-butoxy-bis(ethylacetoacetate)zirconium, di-sec-butoxy-bis(ethylacetoacetate)zirconium, di-tert-butoxy-bis(ethylacetoacetate)zirconium, monoethoxy-tris(ethylacetoacetate)zirconium, mono-n-propoxy-tris(ethylacetoacetate)zirconium, mono-isopropoxy-tris(ethylacetoacetate)zirconium, mono-n-butoxy-tris(ethylacetoacetate)zirconium, mono-sec-butoxy-tris(ethylacetoacetate)zirconium, mono-tert-butoxy-tris(ethylacetoacetate)zirconium, tetrakis(ethylacetoacetate)zirconium, mono(acetylacetonate)tris(ethylacetoacetate)zirconium, bis(acetylacetonate)bis(ethylacetoacetate)zirconium, and tris(acetylacetonate)mono(ethylacetoacetate)zirconium; and aluminum chelate compounds such as tris(acetylacetonate)aluminum and tris(ethylacetoacetate)aluminum.

Examples of the organic acid as the hydrolysis catalyst include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, and tartaric acid.

Examples of the inorganic acid as the hydrolysis catalyst include hydrochloric acid, nitric acid, sulfuric acid, hydrofluoric acid, and phosphoric acid.

Examples of the organic base as the hydrolysis catalyst include pyridine, pyrrole, piperazine, pyrrolidine, piperidine, picoline, trimethylamine, triethylamine, monoethanolamine, diethanolamine, dimethylmonoethanolamine, monomethyldiethanolamine, triethanolamine, diazabicyclo octane, diazabicyclo nonane, diazabicyclo undecene, and tetramethylammoniumhydroxide.

Examples of the inorganic base as the hydrolysis catalyst include ammonia, sodium hydroxide, potassium hydroxide, barium hydroxide, and calcium hydroxide.

Among these catalysts, metal chelate compounds, organic acids, and inorganic acids are preferred and these catalysts may be used individually or in combination of two or more types thereof.

Examples of the organic solvent used for the hydrolysis include: aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; aromatic hydrocarbon solvents such as benzene, toluene, xylene, ethylbenzene, trimethylbenzene, methylethylbenzene, n-propylbenzene, isopropylbenzene, diethylbenzene, isobutylbenzene, triethylbenzene, di-isopropylbenzene, n-amylnaphthalene, and trimethylbenzene; monoalcohol solvents such as methanol, ethanol, n-propanol, isopropanol, n-butanol, isobutanol, sec-butanol, tert-butanol, n-pentanol, isopentanol, 2-methylbutanol, sec-pentanol, tert-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethylcarbinol, diacetone alcohol, and cresol; polyalcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methyl ethyl ketone, methyl-n-propyl ketone, methyl-n-butyl ketone, diethyl ketone, methyl-isobutyl ketone, methyl-n-pentyl ketone, ethyl-n-butyl ketone, methyl-n-hexyl ketone, di-isobutyl ketone, trimethylnonanone, cyclohexanone, methylcyclohexanone, 2,4-pentanedione, acetonylacetone, diacetone alcohol, acetophenone, and fenchone; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethyleneglycol monomethyl ether acetate, ethyleneglycol monoethyl ether acetate, diethyleneglycol monomethyl ether acetate, diethyleneglycol monoethyl ether acetate, diethyleneglycol mono-n-butyl ether acetate, propyleneglycol monomethyl ether acetate, propyleneglycol monoethyl ether acetate, propyleneglycol monopropyl ether acetate, propyleneglycol monobutyl ether acetate, dipropyleneglycol monomethyl ether acetate, dipropyleneglycol monoethyl ether acetate, glycol diacetate, methoxytriglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethylsulfoxide, sulfolane, and 1,3-propane sultone. These solvents may be used individually or in combination of two or more types thereof.

For example, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol monomethyl ether acetate, propylene glycol monoethyl ether acetate, and propylene glycol monopropyl ether acetate are preferred.

Ketones such as acetone and nonalcoholic polar solvents such as tetrahydrofuran are preferred and when a hydrolyzable organosilane (a silane having 2 to 3 hydrolyzable groups in the molecule of the hydrolyzable silane) of Formula (1) used in the present invention is used as a raw material, they are preferred. However, in the case of a hydrolyzable organosilane having 5 to 9 hydrolyzable groups in the molecule, the hydrolysis and the condensation are excessively progressed so that the gelation is easily caused in such an acetone solvent.

From the solution of the hydrolysis-condensation product (polymer) obtained by hydrolyzing and condensing a hydrolyzable organosilane in a solvent using a catalyst, an alcohol as a by-product, the used hydrolyzing catalyst, and the used water can be simultaneously removed by distilling them under reduced pressure or the like. An acid catalyst or a base catalyst used for the hydrolysis can be removed by neutralization or ion exchange. Then, to the resist underlayer film forming composition for lithography of the present invention containing the hydrolysis-condensation product thereof, an acid (organic acid), a salt, water, an alcohol, or a combination thereof can be added to stabilize the composition.

Examples of the organic acid include oxalic acid, malonic acid, methylmalonic acid, succinic acid, maleic acid, malic acid, tartaric acid, phthalic acid, citric acid, glutaric acid, citric acid, lactic acid, and salicylic acid. Among them, oxalic acid and maleic acid are preferred. The amount of the organic acid to be blended in is 0.5 to 5.0 parts by mass, relative to 100 parts by mass of the hydrolysis-condensation product (polyorganosiloxane). As the water to be blended in, pure water, ultrapure water, ion-exchanged water, or the like can be used and the blended amount thereof can be 1 to 20 part(s) by mass, relative to 100 parts by mass of the resist underlayer film forming composition.

As an additive, bisphenol S or a bisphenol S derivative can be blended in the composition. The amount of bisphenol S or a bisphenol S derivative is 0.01 to 20 parts by mass, or 0.01 to 10 parts by mass, or 0.01 to 5 parts by mass, relative to 100 parts by mass of the polyorganosiloxane.

Preferred examples of bisphenol S or a bisphenol S derivative include the compounds below.

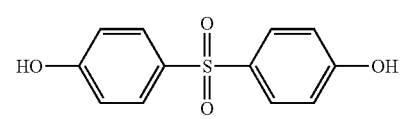

Formula (C-1)

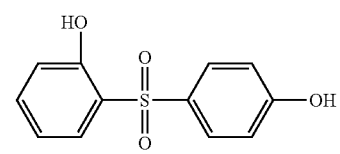

Formula (C-2)

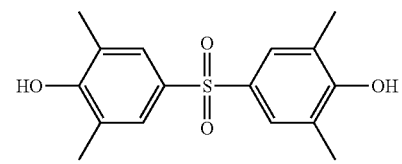

Formula (C-3)

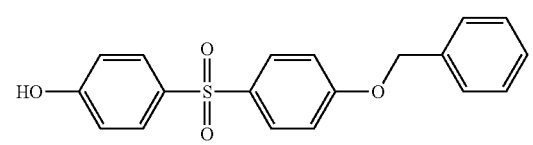

Formula (C-4)

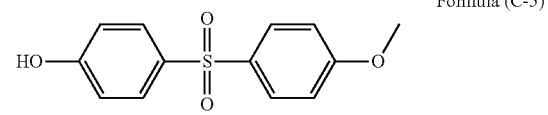

Formula (C-5)

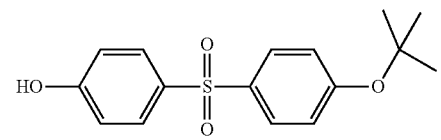

Formula (C-6)

Formula (C-7)
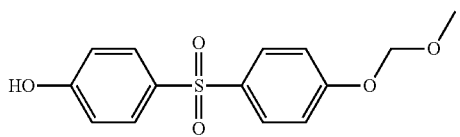

Formula (C-8)
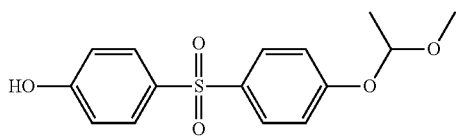

Formula (C-9)
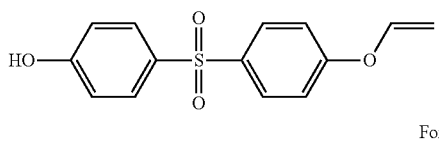

Formula (C-10)
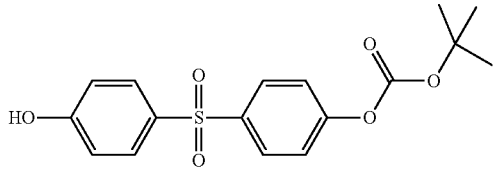

Formula (C-11)
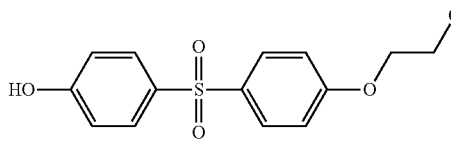

Formula (C-12)
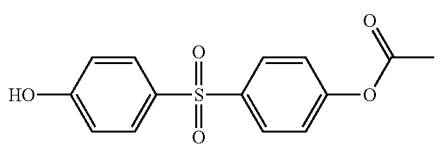

Formula (C-13)
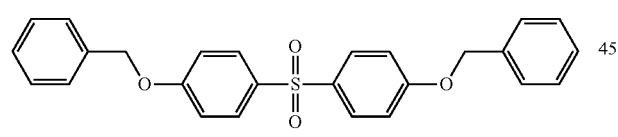

Formula (C-14)
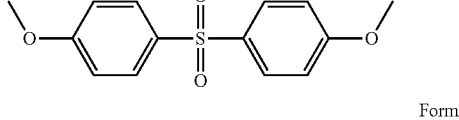

Formula (C-15)
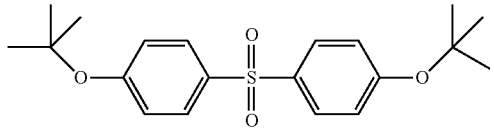

Formula (C-16)
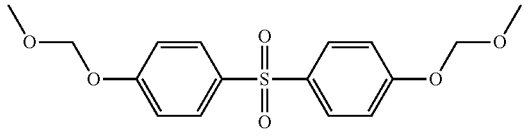

Formula (C-17)
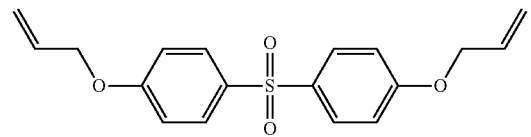

Formula (C-18)
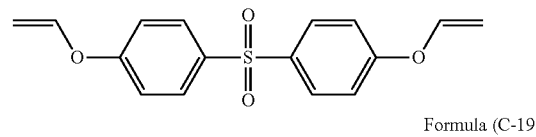

Formula (C-19)
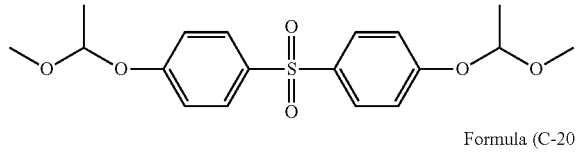

Formula (C-20)
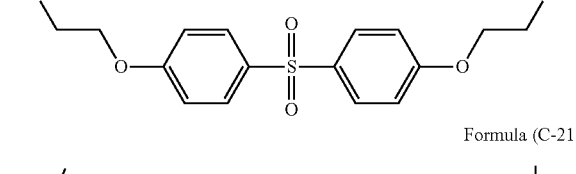

Formula (C-21)
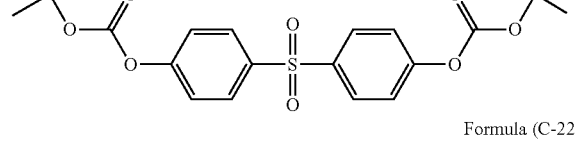

Formula (C-22)
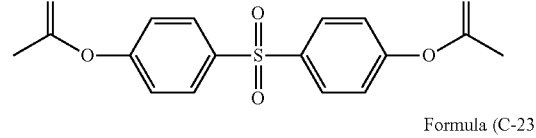

Formula (C-23)
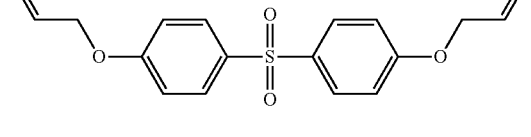

The resist underlayer film forming composition of the present invention may contain a salt. The salt performs a function as a curing catalyst when the coating film containing a polyorganosiloxane composed of a hydrolysis-condensation product is heated to be cured.

As the salt, there can be used ammonium salts, phosphines, phosphonium salts, and sulfonium salts.

Examples of the ammonium salt include: quaternary ammonium salts having a structure of Formula (D-1):

Formula (D-1)
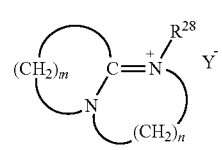

(where m is 2 to 11; n is an integer of 2 to 3; $R^{28}$ is an alkyl group or an aryl group; and $Y^-$ is an anion); quaternary ammonium salts having a structure of Formula (D-2):

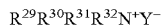

$$R^{29}R^{30}R^{31}R^{32}N^+Y^- \quad \text{Formula (D-2)}$$

(where $R^{29}$, $R^{30}$, $R^{31}$, and $R^{32}$ are independently an alkyl group or an aryl group; N is a nitrogen atom; $Y^-$ is an anion; and $R^{29}$, $R^{30}$, $R^{31}$, and $R^{32}$ are independently bonded to a nitrogen atom through a C—N bond); quaternary ammonium salts having a structure of Formula (D-3):

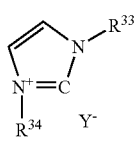

Formula (D-3)

(where $R^{33}$ and $R^{34}$ are independently an alkyl group or an aryl group; and $Y^-$ is an anion); quaternary ammonium salts having a structure of Formula (D-4):

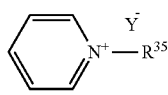

Formula (D-4)

(where $R^{35}$ is an alkyl group or an aryl group; and $Y^-$ is an anion); quaternary ammonium salts having a structure of Formula (D-5):

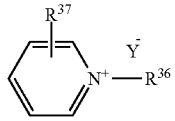

Formula (D-5)

(where $R^{36}$ and $R^{37}$ are independently an alkyl group or an aryl group; and $Y^-$ is an anion); and tertiary ammonium salts having a structure of Formula (D-6):

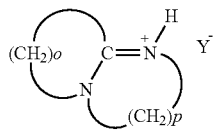

Formula (D-6)

(where o is 2 to 11; p is an integer of 2 to 3; H is a hydrogen atom; and $Y^-$ is an anion).

Examples of the phosphonium salt include quaternary phosphonium salts having a structure of Formula (D-7):

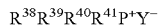

$$R^{38}R^{39}R^{40}R^{41}P^+Y^- \quad \text{Formula (D-7)}$$

(where $R^{38}$, $R^{39}$, $R^{40}$ and $R^{41}$ are independently an alkyl group or an aryl group; P is a phosphorus atom; $Y^-$ is an anion; and $R^{38}$, $R^{39}$, $R^{40}$ and $R^{41}$ are independently bonded to a phosphorus atom through a C—P bond).

Examples of the sulfonium salt include tertiary sulfonium salts of Formula (D-8):

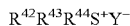

$$R^{42}R^{43}R^{44}S^+Y^- \quad \text{Formula (D-8)}$$

(where $R^{42}$, $R^{43}$, and $R^{44}$ are independently an alkyl group or an aryl group; S is a sulfur atom; $Y^-$ is an anion; and $R^{42}$, $R^{43}$, and $R^{44}$ are independently bonded to a sulfur atom through a C—S bond).

The compound of Formula (D-1) is a quaternary ammonium salt derived from an amine and in Formula (D-1), m is 2 to 11 and n is an integer of 2 to 3. $R^{28}$ of the quaternary ammonium salt is a $C_{1-18}$, preferably $C_{2-10}$ alkyl group or a $C_{6-18}$, preferably $C_{6-10}$ aryl group and examples thereof include: linear alkyl groups such as an ethyl group, a propyl group, and a butyl group; a benzyl group; a cyclohexyl group; a cyclohexylmethyl group; and a dicyclopentadienyl group. Examples of the anion ($Y^-$) include: halogen ions such as a chlorine ion ($Cl^-$), a bromine ion ($Br^-$), and an iodine ion ($I^-$); and acid groups such as carboxylato (—COO$^-$), sulfonato (—SO$_3^-$), and alcoholate (—O$^-$).

The compound of Formula (D-2) is a quaternary ammonium salt of $R^{29}R^{30}R^{31}R^{32}N^+Y^-$. $R^{29}$, $R^{30}$, $R^{31}$, and $R^{32}$ of the quaternary ammonium salt are independently a $C_{1-18}$ alkyl group, a $C_{6-18}$ aryl group, or a silane compound bonded to a silicon atom through a Si—C bond. Examples of the anion ($Y^-$) include: halogen ions such as a chlorine ion ($Cl^-$), a bromine ion ($Br^-$), and an iodine ion ($I^-$); and acid groups such as carboxylato (—COO$^-$), sulfonato (—SO$_3^-$) and alcoholate (—O$^-$). The quaternary ammonium salt is commercially available and examples thereof include tetramethylammonium acetate, tetrabutylammonium acetate, triethylbenzylammonium chloride, triethylbenzylammonium bromide, trioctylmethylammonium chloride, tributylbenzylammonium chloride, and trimethylbenzylammonium chloride.

The compound of Formula (D-3) is a quaternary ammonium salt derived from a 1-substituted imidazole and in Formula (D-3), $R^{33}$ and $R^{34}$ are independently a $C_{1-18}$ alkyl group or a $C_{6-18}$ aryl group. The sum of the numbers of carbon atoms of $R^{33}$ and $R^{34}$ is preferably 7 or more. Examples of $R^{33}$ include a methyl group, an ethyl group, a propyl group, a phenyl group, and a benzyl group and examples of $R^{34}$ include a benzyl group, an octyl group, and an octadecyl group. Examples of the anion ($Y^-$) include: halogen ions such as a chlorine ion ($Cl^-$), a bromine ion ($Br^-$), and an iodine ion ($I^-$); and acid groups such as carboxylato (—COO$^-$), sulfonato (—SO$_3^-$), and alcoholate (—O$^-$). The compound either is commercially available or can be produced, for example, by reacting an imidazole-based compound such as 1-methylimidazole and 1-benzylimidazole with a halogenated alkyl or halogenated aryl such as benzyl bromide and methyl bromide.

The compound of Formula (D-4) is a quaternary ammonium salt derived from pyridine and in Formula (D-4), $R^{35}$ is a $C_{1-18}$, preferably $C_{4-18}$ alkyl group or a $C_{6-18}$ aryl group and examples thereof include a butyl group, an octyl group, a benzyl group, and a lauryl group. Examples of the anion ($Y^-$) include: halogen ions such as a chlorine ion ($Cl^-$), a bromine ion ($Br^-$), and an iodine ion ($I^-$); and acid groups such as carboxylato (—COO$^-$), sulfonato (—SO$_3^-$), and alcoholate (—O$^-$). The compound either is commercially available or can be produced, for example, by reacting pyridine with a halogenated alkyl or halogenated aryl such as lauryl chloride, benzyl chloride, benzyl bromide, methyl bromide, and octyl bromide. Examples of the compound include N-laurylpyridinium chloride and N-benzylpyridinium bromide.

The compound of Formula (D-5) is a quaternary ammonium salt derived from a substituted pyridine represented by picoline and the like and in Formula (D-5), $R^{36}$ is a $C_{1-18}$, preferably $C_{4-18}$ alkyl group or a $C_{6-18}$ aryl group and examples thereof include a methyl group, an octyl group, a lauryl group, and a benzyl group. $R^{37}$ is a $C_{1-18}$ alkyl group or a $C_{6-18}$ aryl group and for example, when the compound is a quaternary ammonium derived from picoline, $R^{37}$ is a methyl group. Examples of the anion ($Y^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound either is commercially available or can be produced, for example, by reacting a substituted pyridine such as picoline with a halogenated alkyl or a halogenated aryl such as methyl bromide, octyl bromide, lauryl chloride, benzyl chloride, and benzyl bromide. Examples of the compound include N-benzylpicolinium chloride, N-benzylpicolinium bromide, and N-laurylpicolinium chloride.

The compound of Formula (D-6) is a tertiary ammonium salt derived from an amine and in Formula (D-6), o is 2 to 11 and p is an integer of 2 to 3. Examples of the anion ($Y^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound can be produced by a reaction of an amine with a weak acid such as a carboxylic acid and phenol. Examples of the carboxylic acid include formic acid and acetic acid. When formic acid is used, the anion ($Y^-$) is ($HCOO^-$) and when acetic acid is used, the anion ($Y^-$) is ($CH_3COO^-$). In addition, when phenol is used, the anion ($Y^-$) is ($C_6H_5O^-$).

The compound of Formula (D-7) is a quaternary phosphonium salt having a structure of $R^{38}R^{39}R^{40}R^{41}P^+Y^-$. $R^{38}$, $R^{39}$, $R^{40}$, and $R^{41}$ are independently a $C_{1-18}$ alkyl group, a $C_{6-18}$ aryl group, or a silane compound bonded to a silicon atom through a Si—C bond. Preferably, three groups among four substituents of $R^{38}$ to $R^{41}$ are a phenyl group or a substituted phenyl group such as a phenyl group and a tolyl group and the residual one group is a $C_{1-18}$ alkyl group, an aryl group, or a silane compound bonded to a silicon atom through a Si—C bond. Examples of the anion ($Y^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$).

The compound is commercially available and examples of the compound include: halogenated tetraalkylphosphoniums such as a halogenated tetra-n-butylphosphonium and a halogenated tetra-n-propylphosphonium; halogenated trialkylbenzylphosphoniums such as a halogenated triethylbenzylphosphonium; halogenated triphenylmonoalkylphosphoniums such as a halogenated triphenylmethylphosphonium and a halogenated triphenylethylphosphonium; halogenated triphenylbenzylphosphoniums; halogenated tetraphenylphosphoniums; halogenated tritolylmonoarylphosphoniums; and halogenated tritolylmonoalkylphosphoniums (where the halogen atom is a chlorine atom or a bromine atom). Particularly preferred examples of the compound include: halogenated triphenylmonoalkylphosphoniums such as a halogenated triphenylmethylphosphonium and a halogenated triphenylethylphosphonium; halogenated triphenylmonoarylphosphoniums such as a halogenated triphenylbenzylphosphonium; halogenated tritolylmonoarylphosphoniums such as a halogenated tritolylmonophenylphosphonium; and halogenated tritolylmonoalkylphosphoniums (where the halogen atom is a chlorine atom or a bromine atom) such as a halogenated tritolylmonomethylphosphonium.

Examples of the phosphines include: primary phosphines such as methylphosphine, ethylphosphine, propylphosphine, isopropylphosphine, isobutylphosphine, and phenylphosphine; secondary phosphines such as dimethylphosphine, diethylphosphine, diisopropylphosphine, diisoamylphosphine, and diphenylphosphine; tertiary phosphines such as trimethylphosphine, triethylphosphine, triphenylphosphine, methyldiphenylphosphine, and dimethylphenylphosphine.

The compound of Formula (D-8) is a tertiary sulfonium salt having a structure of $R^{42}R^{43}R^{44}S^+R^-$. $R^{42}$, $R^{43}$, and $R^{44}$ are independently a $C_{1-18}$ alkyl group, a $C_{6-18}$ aryl group, or a silane compound bonded to a silicon atom through a Si—C bond. Preferably, three groups among four substituents of $R^{42}$ to $R^{44}$ are a phenyl group or a substituted phenyl group such as a phenyl group and a tolyl group and the residual one group is a $C_{1-18}$ alkyl group or a $C_{6-18}$ aryl group. Examples of the anion ($Y^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). Examples of this alkyl group or aryl group include functional groups having the number of carbon atoms corresponding to the number of carbon atoms of the above exemplified alkyl groups or aryl groups.

The compound is commercially available and examples of the compound include: halogenated tetraalkylsulfoniums such as a halogenated tri-n-butylsulfonium and a halogenated tri-n-propylsulfonium; halogenated trialkylbenzylsulfoniums such as a halogenated diethylbenzylsulfonium; halogenated diphenylmonoalkylsulfoniums such as a halogenated diphenylmethylsulfonium and a halogenated diphenylethylsulfonium; halogenated triphenylsulfoniums (where the halogen atom is a chlorine atom or a bromine atom); tetraalkylphosphoniums carboxylates such as tri-n-butylsulfonium carboxylate and tri-n-propylsulfonium carboxylate; trialkylbenzylsulfonium carboxylates such as diethylbenzylsulfonium carboxylate; diphenylmonoalkylsulfonium carboxylates such as diphenylmethylsulfonium carboxylate and diphenylethylsulfonium carboxylate; and triphenylsulfonium carboxylate. Particularly preferred are halogenated triphenylsulfonium and triphenylsulfonium carboxylate.

The amount of the salt is 0.01 to 10 parts by mass, or 0.01 to 5 parts by mass, or 0.01 to 3 parts by mass, relative to 100 parts by mass of the polyorganosiloxane.

The underlayer film forming composition for lithography of the present invention may contain, besides the components described above, if necessary, organic polymer compounds, photoacid generators, surfactants, and the like.

By using an organic polymer compound, there can be controlled the dry etching rate (a decreased amount of the film thickness per unit time), the attenuation coefficient, the refractive index, and the like of a resist underlayer film formed from the underlayer film forming composition for lithography of the present invention.

The organic polymer compound is not particularly limited and various organic polymers such as condensation polymerization polymers and addition polymerization polymers can be used. As the organic polymer compound, there can be used addition polymerization polymers and condensation polymerization polymers such as polyesters, polystyrenes, polyimides, acrylic polymers, methacrylic polymers, polyvinylethers, phenolnovolacs, naphtholnovolacs, polyethers, polyamides, and polycarbonates. There are preferably used organic polymers having an aromatic ring structure functioning as a light absorbing moiety such as a benzene ring, a naphthalene ring, an anthracene ring, a triazine ring, a quinoline ring, and a quinoxaline ring.

Examples of such an organic polymer compound include addition polymerization polymers containing as a structure unit thereof, an addition polymerizable monomer such as beuzylacrylate, benzylmethacrylate, phenylacrylate, naphthylacrylate, anthrylmethacrylate, anthrylmethylmethacrylate, styrene, hydroxystyrene, benzylvinyl ether, and N-phenylmaleimide, and condensation polymerization polymers such as phenolnovolacs and naphtholnovolacs.

When an addition polymerization polymer is used as the organic polymer compound, the polymer compound may be either a homopolymer or a copolymer. For producing the addition polymerization polymer, an addition polymerizable monomer is used. Examples of such an addition polymerizable monomer include acrylic acid, methacrylic acid, acrylic acid ester compounds, methacrylic acid ester compounds, acrylamide compounds, methacrylamide compounds, vinyl compounds, styrene compounds, maleimide compounds, maleic anhydride, and acrylonitrile.

Examples of the acrylic acid ester compound include methyl acrylate, ethyl acrylate, normal hexyl acrylate, isopropyl acrylate, cyclohexyl acrylate, benzyl acrylate, phenyl acrylate, anthrylmethyl acrylate, 2-hydroxyethyl acrylate, 3-chloro-2-hydroxypropyl acrylate, 2-hydroxypropyl acrylate, 2,2,2-trifluoroethyl acrylate, 2,2,2-trichloroethyl acrylate, 2-bromoethyl acrylate, 4-hydroxybutyl acrylate, 2-methoxyethyl acrylate, tetrahydrofurfuryl acrylate, 2-methyl-2-adamantyl acrylate, 5-acryloyloxy-6-hydroxynorbornene-2-carboxylic-6-lactone, 3-acryloxypropyltriethoxysilane, and glycidyl acrylate.

Examples of the methacrylic acid ester compound include methyl methacrylate, ethyl methacrylate, normal hexyl methacrylate, isopropyl methacrylate, cyclohexyl methacrylate, benzyl methacrylate, phenyl methacrylate, anthrylmethyl methacrylate, 2-hydroxyethyl methacrylate, 2-hydroxypropyl methacrylate, 2,2,2-trifluoroethyl methacrylate, 2,2,2-trichloroethyl methacrylate, 2-bromoethyl methacrylate, 4-hydroxybutyl methacrylate, 2-methoxyethyl methacrylate, tetrahydrofurfuryl methacrylate, 2-methyl-2-adamantyl methacrylate, 5-methacryloyloxy-6-hydroxynorbornene-2-carboxylic-6-lactone, 3-methacryloxypropyltriethoxysilane, glycidyl methacrylate, 2-phenylethyl methacrylate, hydroxyphenyl methacrylate, and bromophenyl methacrylate.

Examples of the acrylamide compound include acrylamide, N-methylacrylamide, N-ethylacrylamide, N-benzylacrylamide, N-phenylacrylamide, N,N-dimethylacrylamide, and N-anthrylacrylamide.

Examples of the methacrylamide compound include methacrylamide, N-methylmethacrylamide, N-ethylmethacrylamide, N-benzylmethacrylamide, N-phenylmethacrylamide, N,N-dimethylmethacrylamide, and N-anthrylacrylamide.

Examples of the vinyl compound include vinyl alcohol, 2-hydroxyethyl vinyl ether, methyl vinyl ether, ethyl vinyl ether, benzyl vinyl ether, vinylacetic acid, vinyltrimethoxysilane, 2-chloroethyl vinyl ether, 2-methoxyethyl vinyl ether, vinylnaphthalene, and vinylanthracene.

Examples of the styrene compound include styrene, hydroxystyrene, chlorostyrene, bromostyrene, methoxystyrene, cyanostyrene, and acetylstyrene.

Examples of the maleimide compound include maleimide, N-methylmaleimide, N-phenylmaleimide, N-cyclohexylmaleimide, N-benzylmaleimide, and N-hydroxyethylmaleimide.

When a condensation polymerization polymer is used as the organic polymer compound, examples of such a polymer include condensation polymerization polymers of a glycol compound and a dicarboxylic acid compound. Examples of the glycol compound include diethylene glycol, hexamethylene glycol, and butylene glycol.

Examples of the dicarboxylic acid compound include succinic acid, adipic acid, terephthalic acid, and maleic anhydride. Examples of the polymer also include polyesters, polyamides, and polyimides such as polypyromellitimide, poly(p-phenyleneterephthalamide), polybutyleneterephthalate, and polyethyleneterephthalate.

When the organic polymer compound contains a hydroxy group, the hydroxy group can effect a crosslinking reaction with a polyorganosiloxane.

As the organic polymer compound, there can be used a polymer compound having a weight average molecular weight of, for example, 1,000 to 1,000,000, or 3,000 to 300,000, or 5,000 to 200,000, or 10,000 to 100,000.

The organic polymer compounds may be used individually or in combination of two or more types thereof.

When the organic polymer compound is used, the content thereof is 1 to 200 part(s) by mass, or 5 to 100 parts by mass, or 10 to 50 parts by mass, or 20 to 30 parts by mass, relative to 100 parts by mass of the hydrolysis-condensation product (polyorganosiloxane).

The resist underlayer film forming composition of the present invention may contain an acid generator.

Examples of the acid generator include thermoacid generators and photoacid generators.

The photoacid generator generates an acid during exposure of the resist. Therefore, the acidity of the underlayer film can be controlled. This is one method for adjusting the acidity of the underlayer film to that of the resist as an upper layer of the underlayer film. By adjusting the acidity of the underlayer film, the pattern shape of the resist formed in the upper layer can be controlled.

Examples of the photoacid generator contained in the resist underlayer film forming composition of the present invention include onium salt compounds, sulfonimide compounds, and disulfonyl diazomethane compounds.

Examples of the onium salt compound include: iodonium salt compounds such as diphenyliodoniumhexafluorophosphate, diphenyliodoniumtrifluoromethanesulfonate, diphenyliodoniumnonafluoro normal butane sulfonate, diphenyliodoniumperfluoro normal octane sulfonate, diphenyliodoniumcamphorsulfonate, bis(4-tert-butylphenyl)iodoniumcamphorsulfonate, and bis(4-tert-butylphenyl)iodoniumtrifluoromethanesulfonate; and sulfonium salt compounds such as triphenylsulfoniumhexafluoroantimonate, triphenylsulfoniumnonafluoro normal butane sulfonate, triphenylsulfoniumcamphorsulfonate, and triphenylsulfoniumtrifluoromethanesulfonate.

Examples of the sulfonimide compound include N-(trifluoromethanesulfonyloxy)succinimide, N-(nonafluoro normal butane sulfonyloxy)succinimide, N-(camphorsulfonyloxy)succinimide, and N-(trifluoromethanesulfonyloxy)naphthalimide.

Examples of the disulfonyldiazomethane compound include bis(trifluoromethylsulfonyl)diazomethane, bis(cyclohexylsulfonyl)diazomethane, bis (phenylsulfonyl)diazomethane, bis(p-toluenesulfonyl)diazomethane, bis(2,4-dimethylbenzenesulfonyl)diazomethane, and methylsulfonyl-p-toluenesulfonyldiazomethane.

These photoacid generators may be used individually or in combination of two or more types thereof.

When the photoacid generator is used, the content thereof is 0.01 to 5 parts by mass, or 0.1 to 3 parts by mass, or 0.5 to 1 part(s) by mass, relative to 100 parts by mass of the condensation product (polyorganosiloxane).

The surfactant is effective for suppressing the formation of a pin hole, a striation, and the like when the resist underlayer film forming composition for lithography of the present invention is applied on a substrate.

Examples of the surfactant contained in the resist underlayer film forming composition of the present invention include: nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylallyl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorinated surfactants, for example, EFTOP EF301, EF303, and EF352 (trade name; manufactured by Tohkem Products Corp.), MEGAFAC (registered trade mark) F171, F173, R-08, and R-30 (trade name; manufactured by DIC, Inc.), Fluorad FC430 and FC431 (trade name; manufactured by Sumitomo 3M Limited), AsahiGuard (registered trade mark) AG710 and Surflon (registered trade mark) S-382, SC101, SC102, SC103, SC104, SC105, and SC106 (trade names; manufactured by Asahi Glass Co., Ltd.); and Organosiloxane polymer KP341 (manufactured by Shin-Etsu Chemical Co., Ltd.).

These surfactants may be used individually or in combination of two or more types thereof. When the surfactant is used, the content thereof is 0.0001 to 5 parts by mass, or 0.001 to 3 parts by mass, or 0.01 to 0.5 parts by mass, relative to 100 parts by mass of the condensation product (polyorganosiloxane).

In the resist underlayer film forming composition of the present invention, a rheology controlling agent and an adhesion assistant may be blended. The rheology controlling agent is effective for enhancing the fluidity of the underlayer film forming composition. The adhesion assistant is effective for enhancing the adhesion of the underlayer film to the semiconductor substrate or the resist.

Specific examples of the rheology controlling agent include: phthalic acid derivatives such as dimethyl phthalate, diethyl phthalate, diisobutyl phthalate, dihexyl phthalate, and butylisodecyl phthalate; adipic acid derivatives such as di-normal butyl adipate, diisobutyl adipate, diisooctyl adipate, and octyldecyl adipate; maleic acid derivatives such as di-normal butyl maleate, diethyl maleate, and dinonyl maleate; oleic acid derivatives such as methyl oleate, butyl oleate, and tetrahydrofurfuryl oleate; and stearic acid derivatives such as normal butyl stearate and glyceryl stearate. The rheology controlling agent is blended in an amount of usually less than 30% by mass, relative to 100% by mass of the whole composition of the resist underlayer film forming composition.

Examples of the adhesion assistant include: chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldiethoxysilane, methyldimethoxysilane, dimethylvinylethoxysilane, diphenyldimethoxysilane, and phenyltriethoxylsilane; silazanes such as hexamethyldisilazane, N,N'-bis(trimethylsilyl)urea, dimethyltrimethylsilylamine, and trimethylsilylimidazol; silanes such as vinyltrichlorosilane, γ-chloropropyltrimethoxysilane, γ-aminopropyltriethoxysilane, and γ-glycidoxypropyltrimethoxysilane; heterocyclic compounds such as benzotriazole, benzimidazole, indazole, imidazole, 2-mercaptobenzimidazole, 2-mercaptobenzothiazole, 2-mercaptobenzooxazole, urazole, thiouracil, mercaptoimidazole, and mercaptopyrimidine; and urea compounds such as 1,1-dimethyl urea and 1,3-dimethyl urea or thiourea compounds. The adhesion assistant is blended in the resist underlayer film forming composition in an amount of usually less than 5% by mass, preferably less than 2% by mass, relative to 100% by mass of the whole composition of the resist underlayer film forming composition.

The solvent used for the resist underlayer film forming composition of the present invention is not particularly limited so long as the solvent can dissolve the solid content. Examples of such a solvent include methanol, ethanol, propanol, ispropanol, butanol, methyl cellosolve acetate, ethyl cellosolve acetate, propylene glycol, propylene glycol monomethyl ether, propylene glycol monoethyl ether, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol monomethyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxybutyl acetate, 3-methoxypropyl acetate, 3-methyl-3-methoxybutyl acetate, 3-methyl-3-methoxybutyl propionate, 3-methyl-3-methoxybutyl butyrate, methyl acetoacetate, toluene, xylene, methyl ethyl ketone, methyl propyl ketone, methyl butyl ketone, 2-heptanone, 3-heptanone, 4-heptanone, cyclohexanone, N,N-dimethylformamide, N-methylacetamide, N,N-dimethylacetamide, N-methylpyrrolidone, methyl isobutyl carbinol, and γ-butyrolactone. These solvents may be used individually or in combination of two or more types thereof.

Hereinafter, the use of the resist underlayer film forming composition of the present invention is described.

The resist underlayer film fainting composition of the present invention is applied on a substrate used in the production of semiconductor devices (for example, silicon wafer substrates, silicon/silicon dioxide coated substrates, silicon nitride substrates, glass substrates, ITO substrates, polyimide substrates, low dielectric constant material (low-k material) coated substrates, etc.) by an appropriate coating method such as a spinner and a coater and then, is baked to form a resist underlayer film. The baking conditions are accordingly selected from baking temperatures of 80° C. to 500° C. or 80° C. to 250° C. and baking time of 0.3 to 60 minutes. Preferably, the baking temperature is 150° C. to 500° C. and the baking time is 0.5 to 2 minutes. Here, the formed underlayer film has a film thickness of, for example, 10 to 1,000 nm, or 20 to 500 nm, or 50 to 300 nm, or 100 to 200 nm, or 10 to 100 nm.

Next, on the resist underlayer film, for example a photoresist film is formed. The formation of the photoresist film can be performed by a known method, that is, by applying a photoresist composition solution on the underlayer film and by baking the composition solution. The photoresist has a film thickness of, for example, 50 to 10,000 nm, or 100 to 2,000 nm, or 200 to 1,000 nm, or 30 to 200 nm.

In the present invention, after forming of the organic underlayer film on the substrate, the resist underlayer film of the present invention can be film-formed on the organic underlayer film and further, on the resist underlayer film, the photoresist film can be formed. Thus, even when the pattern width of the photoresist becomes smaller due to a fine pattern processing and the photoresist film is coated thinly for preventing a pattern collapse, the processing of the substrate becomes possible by selecting an appropriate etching gas. For example, the resist underlayer film of the present invention can be processed by using a fluorine-based gas having an etching rate for the resist underlayer film satisfactorily higher than that for the photoresist as an etching gas, and the organic underlayer film can be processed by using an oxygen-based gas having an etching rate for the organic underlayer film satisfactorily higher than that for the resist underlayer film of the present invention as an etching gas. Furthermore, the substrate can be processed by using a fluorine-based gas having an etching rate for the substrate satisfactorily higher than that for the organic underlayer film as an etching gas.

The photoresist formed on the resist underlayer film of the present invention is not particularly limited so long as the photoresist is sensitive to light used for the exposure, and both a negative-type photoresist and a positive-type photoresist can be used. Examples of the photoresist include: a positive-type photoresist made of a novolac resin and 1,2-naphthoquinonediazide sulfonic acid ester; a chemical amplification-type photoresist made of a binder having a group elevating the alkali dissolving rate by being decomposed by an acid, and a photoacid generator; a chemical amplification-type photoresist made of a low molecule compound elevating the alkali dissolving rate of a photoresist by being decomposed by an acid, an alkali-soluble binder, and a photoacid generator; and a chemical amplification-type photoresist made of a binder having a group elevating the alkali dissolving rate by being decomposed by an acid, a low molecule compound elevating the alkali dissolving rate of a photoresist by being decomposed by an acid, and a photoacid generator. Examples of the photoresist include trade name: APEX-E manufactured by Shipley Company, L.L.C., trade name: PAR710 manufactured by Sumitomo Chemical Co., Ltd., and trade name: SEPR430 manufactured by Shin-Etsu Chemical Co., Ltd. The examples also include fluorine atom-containing polymer-based photoresists described in Proc. SPIE, Vol. 3999, 330-334 (2000), Proc. SPIE, Vol. 3999, 357-364 (2000), and Proc. SPIE, Vol. 3999, 365-374 (2000).

Next, the exposure is performed through a predetermined mask. For the exposure, KrF excimer laser (wavelength: 248 nm), ArF excimer laser (wavelength: 193 nm), F2 excimer laser (wavelength: 157 nm), and the like can be used. After the exposure, if necessary, post exposure bake can also be performed. The post exposure bake is performed under conditions accordingly selected from baking temperatures of 70° C. to 150° C. and baking time of 0.3 to 10 minutes.

In the present invention, as the resist, a resist for electron beam lithography can be used instead of the photoresist. As the electron beam resist, both a positive type and a negative type can be used. Examples of the electron beam resist include: a chemical amplification-type resist made of a binder having a group changing the alkali dissolving rate by being decomposed by an acid generator and an acid; a chemical amplification-type resist made of an alkali-soluble binder and a low molecule compound changing the alkali dissolving rate of the resist by being decomposed by an acid generator and an acid; a chemical amplification-type resist made of a binder having a group changing the alkali dissolving rate by being decomposed by an acid generator and an acid, and a low molecule compound changing the alkali dissolving rate of the resist by being decomposed by an acid; a non-chemical amplification-type resist made of a binder having a group changing the alkali dissolving rate by being decomposed by an electron beam; and a non-chemical amplification-type resist made of a binder having a moiety changing the alkali dissolving rate by being broken by an electron beam. Also in the case of using the electron beam resist, a resist pattern can be formed in a resist film in the same manner as in the case of using a photoresist, by using an electron beam as the radiating source.

Next, development is performed by a developer. Consequently, for example when a positive-type photoresist is used, the photoresist film of an exposed part is removed to form a photoresist pattern.

Examples of the developer include alkaline aqueous solutions such as: aqueous solutions of alkali metal hydroxides such as potassium hydroxide and sodium hydroxide; aqueous solutions of quaternary ammonium hydroxides such as tetramethylammonium hydroxide, tetraethylammonium hydroxide, and choline; and aqueous solutions of amines such as ethanolamine, propylamine, and ethylenediamine. Furthermore, in these developers, a surfactant and the like may also be added. The conditions for the development are accordingly selected from temperatures of 5 to 50° C. and time of 10 to 600 seconds.

Then, using the thus formed pattern of the photoresist film (upper layer) as a protecting film, the removal of the resist underlayer film (intermediate layer) of the present invention is performed to perform patterning and next, using the film composed of the patterned photoresist film (upper layer) and the patterned resist underlayer film (intermediate layer) of the present invention as a protecting film, the removal of the organic underlayer film (underlayer) is performed to perform patterning. Finally, using the patterned resist underlayer film (intermediate layer) of the present invention and the patterned organic underlayer film (underlayer) as a protecting film, the processing of the semiconductor substrate is performed.

When the organic underlayer film is not formed on the substrate, using the film composed of the patterned photoresist and the patterned resist underlayer film (intermediate layer) of the present invention as a protecting film, the processing of the semiconductor substrate is performed.

After the photoresist film is patterned, first, the resist underlayer film (intermediate layer) of the present invention at the part where the photoresist film is removed is removed by dry etching to expose the organic underlayer film (underlayer). For dry etching the resist underlayer film of the present invention, there can be used gases such as tetrafluoromethane ($CF_4$), perfluorocyclobutane($C_4F_8$), perfluoropropane ($C_3F_8$), trifluoromethane, carbon monoxide, argon, oxygen, nitrogen, sulfur hexafluoride, difluoromethane, nitrogen trifluoride and chlorine trifluoride, chlorine, and trichloroborane and dichloroborane. For dry etching the resist underlayer film, a halogen-based gas is preferably used. By dry etching with a halogen-based gas, fundamentally, a photoresist film and an organic underlayer film that are composed of organic substances are difficult to be removed. On the contrary, the resist underlayer film of the present invention containing a large amount of silicon atoms is immediately removed by a halogen-based gas. Therefore, the decrease of the film thickness of the photoresist according to dry etching of the resist underlayer film can be suppressed. As a result, the photoresist can be used as a thin film.

The resist underlayer film is dry-etched preferably with a fluorine-based gas and examples of the fluorine-based gas include tetrafluoromethane ($CF_4$), perfluorocyclobutane ($C_4F_8$), perfluoropropane ($C_3F_8$), trifluoromethane, and difluoromethane ($CH_2F_2$).

Subsequently, using the film composed of the patterned photoresist film and the patterned resist underlayer film of the present invention as a protecting film, the removal of the organic underlayer film is performed. The removal of the organic underlayer film (underlayer) is performed by dry etching preferably with an oxygen-based gas. This is because the resist underlayer film of the present invention containing a large amount of silicon atoms is difficult to be removed by dry etching with an oxygen-based gas.

Finally, the processing of the semiconductor substrate is performed. The processing of the semiconductor substrate is performed by dry etching preferably with a fluorine-based gas.

Examples of the fluorine-based gas include tetrafluoromethane ($CF_4$), perfluorocyclobutane ($C_4F_8$), perfluoropropane ($C_3F_8$), trifluoromethane, and difluoromethane ($CH_2F_2$).

As an upper layer of the resist underlayer film of the present invention, an organic anti-reflective coating can be formed before the formation of the photoresist film. The anti-reflective coating composition used here is not particularly limited and can be optionally selected from the compositions commonly used in a conventional lithography process to be used. The formation of the anti-reflective coating can be performed by a commonly used method, for example, by applying an anti-reflective coating composition by a spinner or a coater and by baking the composition.

The substrate on which the resist underlayer film forming composition of the present invention is applied may also be a substrate having an organic or inorganic anti-reflective coating formed by a CVD method on its surface and, on the anti-reflective coating, the underlayer film of the present invention can also be formed.

A resist underlayer film formed from the resist underlayer film forming composition of the present invention may absorb a light used in a lithography process depending on the wavelength of the light. Then, in such a case, the resist underlayer film can function as an anti-reflective coating having the effect of preventing a light reflected on the substrate. Furthermore, the underlayer film of the present invention can also be used as a layer for preventing an interaction between the substrate and the photoresist, a layer having a function of preventing an adverse action of a material used in the photoresist or of a substance generated during exposure of the photoresist against the substrate, a layer having a function of preventing the diffusion of a substance generated in or on the substrate during heating and baking to the upper layer photoresist, a barrier layer for reducing a poisoning effect to the photoresist layer by a semiconductor substrate dielectric layer, and the like.

A resist underlayer film formed from the resist underlayer film forming composition can be applied to a substrate in which a via hole used in the dual damascene process is formed to be used as an embedding material capable of filling the hole without any void. The resist underlayer film can also be used as a planarizing material for planarizing the surface of a semiconductor substrate having unevenness.

The present invention provides a novel compound of Formula (E-1):

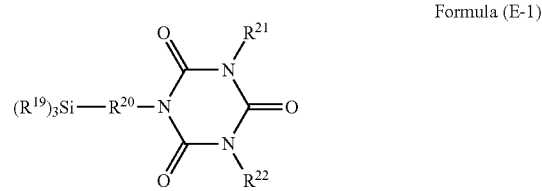

Formula (E-1)

(where $R^{19}$ is an alkoxy group, an acyloxy group, or a halogen group; $R^{20}$ is a $C_{1-10}$ alkylene group or a $C_{2-10}$ alkylene group through a sulfide bond, an ether bond, or an ester bond; and $R^{21}$ and $R^{22}$ are individually a $C_{1-3}$ alkyl group or a glycidyl group), which is used as the raw material.

$R^{19}$ can be an alkoxy group, an acyloxy group, and a halogen group, and is particularly preferably a methoxy group or an ethoxy group. Examples of the $C_{1-10}$ alkylene group as $R^{20}$ include alkylene groups corresponding to the above $C_{1-10}$ alkyl groups, and among them, particularly a propylene group is preferred. Examples of the $C_{1-3}$ alkyl group as $R^{21}$ and $R^{22}$ include a methyl group, an ethyl group, a propyl group, and an isopropyl group.

Hereinafter, the present invention will be further specifically described, referring to Examples, which should not be construed as limiting the scope of the present invention.

EXAMPLE

Raw Material Synthesis Example 1

Into a 300 mL three-neck flask, 30.0 g (0.1774 mol) of monoallyl isocyanurate, 36.42 g (0.2217 mol, 1.25 equivalents relative to 1 mole of a vinyl group) of triethoxysilane, 0.09 g of chloroplatinic (VI) acid hydrate, and 100 mL of toluene were charged and the reaction was effected at 100° C. for 6 hours. Then, toluene and triethoxysilane which is contained excessively were removed by an evaporator. Then, an extraction operation of the reaction mixture with 100 mL of dichloromethane, 50 mL×3 of distilled water was performed and the organic phase was dehydrated over magnesium sulfate, followed by removing dichloromethane from the organic phase by an evaporator to obtain a crude product. The obtained crude product was purified by distillation to obtain a compound of Formula (E-2), which is an objective product.

The obtained compound was determined by $^1$H-NMR measurement. The measurement was performed under conditions of: test tube: 5 mm; solvent: deuterated chloroform; measuring temperature: room temperature; pulse interval: 5 seconds; cumulative number: 32; and standard sample: tetramethylsilane (TMS).

$^1$H-NMR (400 MHz): 0.63 to 0.68 ppm (t, 2H), 1.20 to 1.24 ppm (t, 9H), 1.71 to 1.80 ppm (m, 2H), 3.80 to 3.88 ppm (q, 6H), 3.82 to 3.88 ppm (t, 2H), 9.36 ppm (s, 2H)

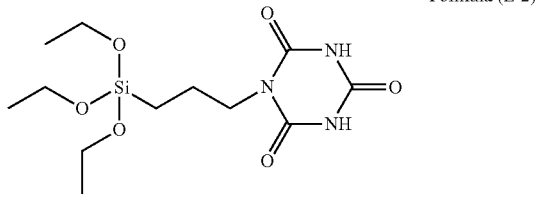

Formula (E-2)

Raw Material Synthesis Example 2

Into a 200 mL four-neck flask equipped with a magnetic stirrer, 10.00 g of monoallyldiglycidyl isocyanurate and 60.00 g of toluene were charged and the resultant reaction mixture was stirred at room temperature. Next, to the reaction mixture, 700 μL of a karstedt catalyst (a 0.1 M xylene solution of a platinum (0)-1,1,3,3-tetramethyldisiloxane complex) was added and into the resultant reaction mixture, 7.1 mL of triethoxysilane was dropped, followed by stirring the resultant reaction mixture at room temperature for 19 hours. After the completion of the reaction, the reaction mixture was concentrated and dried to obtain a crude product. The obtained crude product was distilled by a distillation under reduced pressure under conditions of external temperature 240° C./pressure 0.7 torr to obtain 13.46 g of a compound of Formula (E-3) (85%).

The NMR measurement was performed under the same measurement conditions as above.

$^1$H-NMR (400 MHz) in CDCl$_3$: 0.62 to 0.67 ppm (m, 2H), 1.22 ppm (t, J=7.0 Hz, 9H), 1.73 to 1.79 ppm (m, 2H), 2.68 to 2.71 ppm (m, 2H), 2.82 ppm (dd, J=4.9 Hz, 4.0 Hz, 2H), 3.23 to 3.28 ppm (m, 2H), 3.81 ppm (q, J=7.0 Hz, 6H), 3.86 to 3.91 ppm (m, 2H), 4.00 ppm (dd, J=14.0 Hz, 4.9 Hz, 2H), 4.17 ppm (ddd, J=14.0 Hz, 5.5 Hz, 2.2 Hz, 2H)

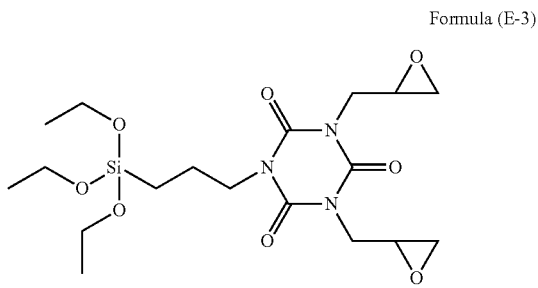 [SMILES: CCO[Si](CCCn1c(=O)n(CC2CO2)c(=O)n(CC2CO2)c1=O)(OCC)OCC]

Formula (E-3)

Raw Material Synthesis Example 3

Into a 300 mL three-neck flask, 10.00 g of dimethylmonoallyl isocyanurate, 24.18 g of (3-mercaptopropyl)triethoxysilane, 0.21 g of azobisisobutylonitrile, and 100 mL of methyl ethyl ketone were charged and the reaction was effected at 95° C. for 6 hours. Then, methyl ethyl ketone was removed by an evaporator. Then, an extraction operation of the reaction mixture with 100 mL of dichloromethane, 50 mL×3 of distilled water was performed and the organic phase was dehydrated over magnesium sulfate, followed by removing dichloromethane from the organic phase by an evaporator to obtain a crude product. The obtained crude product was purified by distillation to obtain a compound of Formula (E-4), which is an objective product.

The NMR measurement was performed under the same measurement conditions as above.

$^1$H-NMR (400 MHz): 0.71 to 0.75 ppm (t, 2H), 1.20 to 1.25 ppm (t, 9H), 1.65 to 1.73 ppm (quint, 2H), 1.90 to 1.98 ppm (quint, 2H), 2.53 to 2.57 ppm (m, 4H), 3.35 ppm (s, 6H), 3.79 to 3.85 ppm (quartet, 6H), 3.98 to 4.02 ppm (t, 2H)

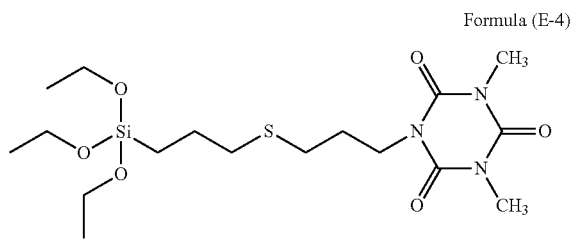 [SMILES: CCO[Si](CCCSCCCn1c(=O)n(C)c(=O)n(C)c1=O)(OCC)OCC]

Formula (E-4)

Raw Material Synthesis Example 4

Into a 300 mL three-neck flask, 10.0 g of dimethylmonoallyl isocyanurate, 12.49 g of triethoxysilane, 0.03 g of chloroplatinic (VI) acid hydrate, and 100 mL of methyl ethyl ketone were charged and the reaction was effected at 100° C. for 6 hours. Then, methyl ethyl ketone and triethoxysilane which is contained excessively were removed by an evaporator. Then, an extraction operation of the reaction mixture with 100 mL of dichloromethane, 50 mL×3 of distilled water was performed and the organic phase was dehydrated over magnesium sulfate, followed by removing dichloromethane from the organic phase by an evaporator to obtain a crude product. The obtained crude product was purified by distillation to obtain a compound of Formula (E-5), which is an objective product.

The NMR measurement was performed under the same measurement conditions as above.

$^1$H-NMR (400 MHz): 0.59 to 0.65 ppm (t, 2H), 1.14 to 1.23 ppm (t, 9H), 1.68 to 1.76 ppm (quint, 2H), 3.30 to 3.32 ppm (s, 6H), 3.69 to 3.86 ppm (m, 8H)

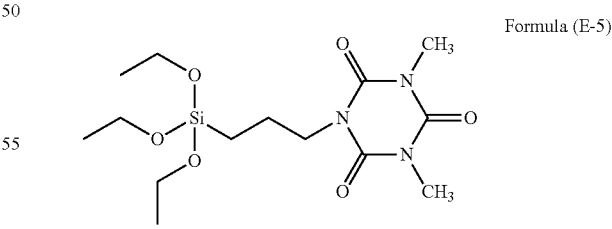

Formula (E-5)

Synthesis Example 1

49.74 g (70 mol %) of tetraethoxysilane, 9.12 g (15 mol %) of methyltriethoxysilane, 21.16 g (15 mol %) of 3-(triethoxysilylpropyl)diallylisocyanurate, and 106.35 g of acetone were charged into a 300-mL flask and while stirring the mixture solution with a magnetic stirrer, 22.74 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-1) measured by GPC was Mw 1,900 in terms of polystyrene.

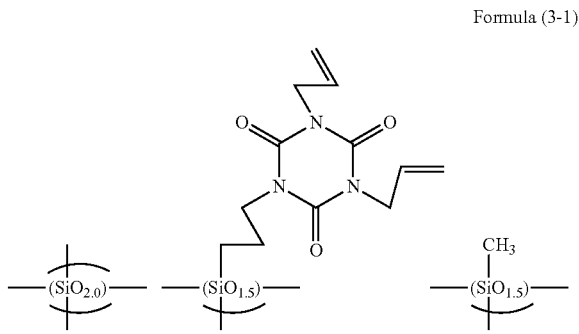

Formula (3-1)

Synthesis Example 2

51.46 g (70 mol %) of tetraethoxysilane, 9.44 g (15 mol %) of methyltriethoxysilane, 19.13 g (15 mol %) of 3-(triethoxysilylpropyl)dimethylisocyanurate, and 105.88 g of acetone were charged into a 300-mL flask and while stirring the mixture solution with a magnetic stirrer, 23.53 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-2) measured by GPC was Mw 1,900 in terms of polystyrene.

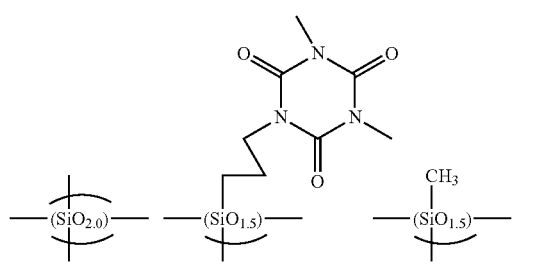

Formula (3-2)

Synthesis Example 3

54.77 g (70 mol %) of tetraethoxysilane, 10.04 g (15 mol %) of methyltriethoxysilane, 7.77 g (5 mol %) of 3-(triethoxysilylpropyl)diallylisocyanurate, 7.45 g (10 mol %) of phenyltrimethoxysilane, and 104.98 g of acetone were charged into a 300-mL flask and while stirring the mixture solution with a magnetic stirrer, 25.04 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction straolution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-3) measured by GPC was Mw 1,500 in terms of polystyrene.

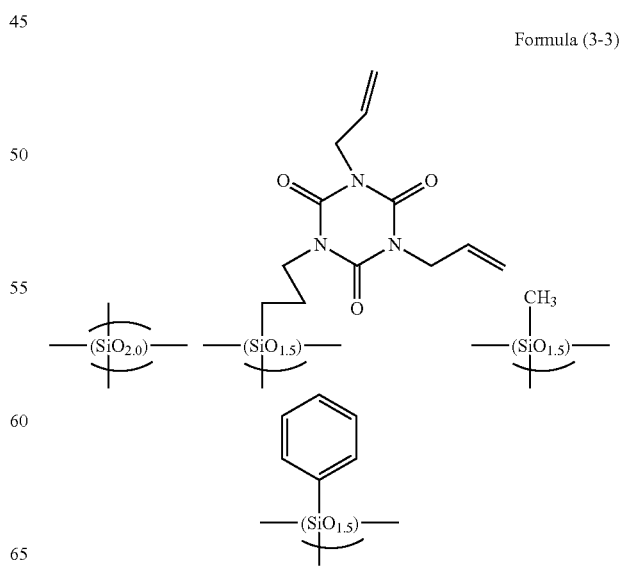

Formula (3-3)

Synthesis Example 4

55.45 g (70 mol %) of tetraethoxysilane, 10.17 g (15 mol %) of methyltriethoxysilane, 6.87 g (5 mol %) of 3-(triethoxysilylpropyl)dimethylisocyanurate, 7.54 g (10 mol %) of phenyltrimethoxysilane, and 104.79 g of acetone were charged into a 300-mL flask and while stirring the mixture solution with a magnetic stirrer, 25.35 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monomethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-4) measured by GPC was Mw 1,900 in terms of polystyrene.

Formula (3-4)

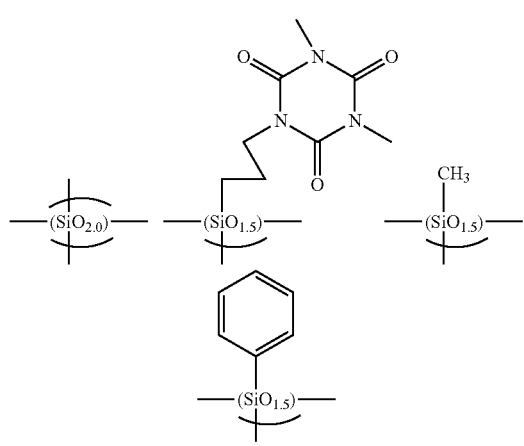

Synthesis Example 5

55.82 g (70 mol %) of tetraethoxysilane, 10.24 g (15 mol %) of methyltriethoxysilane, 6.38 g (5 mol %) of 3-(triethoxysilylpropyl)isocyanurate, 7.59 g (10 mol %) of phenyltrimethoxysilane, and 104.69 g of acetone were charged into a 300-mL flask and while stirring the mixture solution with a magnetic stirrer, 25.52 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-5) measured by GPC was Mw 1,600 in terms of polystyrene.

Formula (3-5)

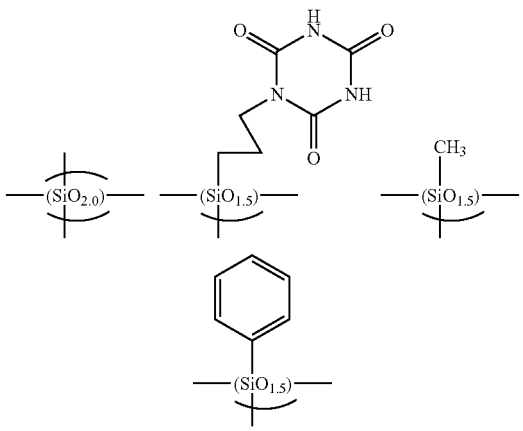

Synthesis Example 6

54.36 g (70 mol %) of tetraethoxysilane, 9.97 g (15 mol %) of methyltriethoxysilane, 8.30 g (5 mol %) of 3-(triethoxysilylpropyl)diglycidylisocyanurate, 7.39 g (10 mol %) of phenyltrimethoxysilane, and 105.09 g of acetone were charged into a 300-mL flask and while stirring the mixture solution with a magnetic stirrer, 24.85 g of a 0.01 mol/L nitric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and nitric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-6) measured by GPC was Mw 2,500 in terms of polystyrene.

Formula (3-6)

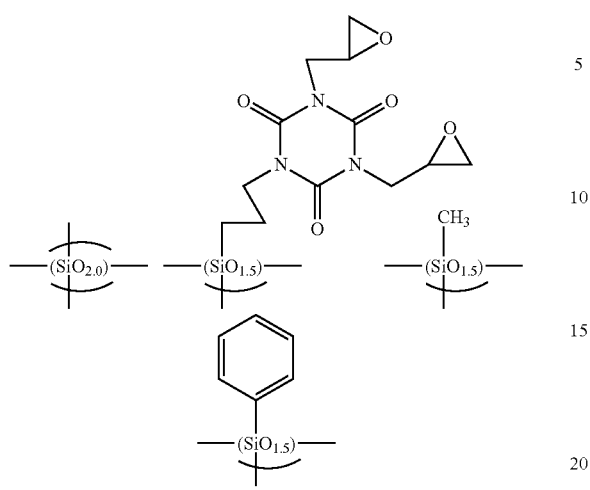

Synthesis Example 7

54.56 g (70 mol %) of tetraethoxysilane, 9.81 g (14.7 mol %) of methyltriethoxysilane, 7.74 g (5 mol %) of 3-(triethoxysilylpropyl)diallylisocyanurate, 7.42 g (10 mol %) of phenyltrimethoxysilane, 0.31 g (0.3 mol %) of N-(3-triethoxysilylpropyl)-4,5-dihydroimidazole, and 105.03 g of acetone were charged into a 300-mL flask and while stirring the mixture solution with a magnetic stirrer, 24.95 g of a 0.10-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-7) measured by GPC was Mw 1,500 in terms of polystyrene.

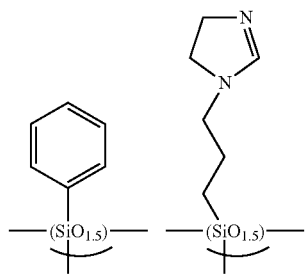

Synthesis Example 8

55.23 g (70 mol %) of tetraethoxysilane, 9.93 g (14.7 mol %) of methyltriethoxysilane, 6.85 g (5 mol %) of 3-(triethoxysilylpropyl)dimethylisocyanurate, 7.51 g (10 mol %) of phenyltrimethoxysilane, 0.31 g (0.3 mol %) of N-(3-triethoxysilylpropyl)-4,5-dihydroimidazole, and 104.85 g of acetone were charged into a 300-mL flask and while stirring the mixture solution with a magnetic stirrer, 25.25 g of a 0.10-mon hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-8) measured by GPC was Mw 1,900 in terms of polystyrene.

Formula (3-7)

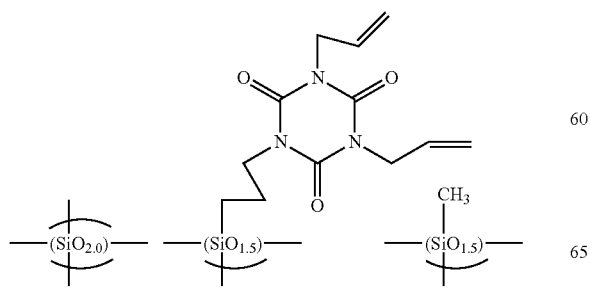

Formula (3-8)

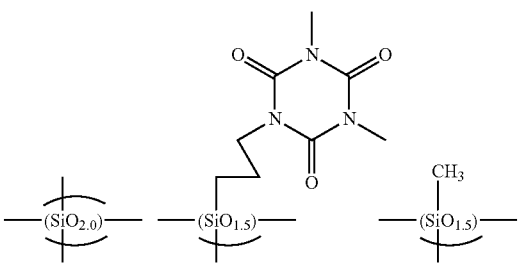

-continued

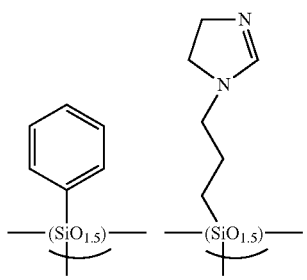

Synthesis Example 9

57.42 g (75 mol %) of tetraethoxysilane, 9.63 g (14.7 mol %) of methyltriethoxysilane, 7.60 g (5 mol %) of 3-(triethoxysilylpropyl)diallylisocyanurate, 4.75 g (5 mol %) of 4-(methoxymethoxy)trimethoxysilylbenzene, 0.30 g (0.3 mol %) of N-(3-triethoxysilylpropyl)-4,5-dihydroimidazole, and 105.10 g of acetone were charged into a 300-mL flask and while stirring the mixture solution with a magnetic stirrer, 24.83 g of a 0.10-mol/L hydrochloric acid was dropped into the mixture solution. After the dropping, the flask was placed into an oil bath controlled to 85° C. and under warming-reflux, the reaction was effected for 240 minutes. Then, to the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-9) measured by GPC was Mw 1,750 in terms of polystyrene.

-continued

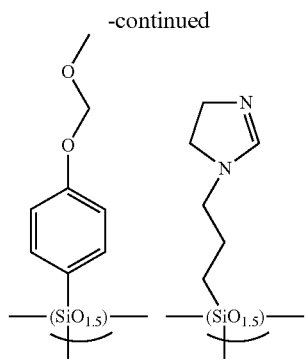

Synthesis Example 10

48.42 g (70 mol %) of tetraethoxysilane, 11.84 g (20 mol %) of methyltriethoxysilane, 6.87 g (5 mol %) of 3-(triethoxysilylpropyl)diallylisocyanurate, 4.02 g (5 mol %) of 4-methoxybenzyltrimethoxysilane, and 106.72 g of acetone were charged into a 300-mL flask and while stirring the mixture solution with a magnetic stirrer, 22.14 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, methanol and ethanol, which were reaction by-products, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-15) measured by GPC was Mw 1,700 in terms of polystyrene.

Formula (3-9)

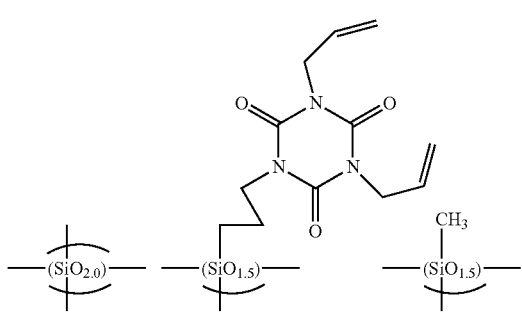

Formula (3-15)

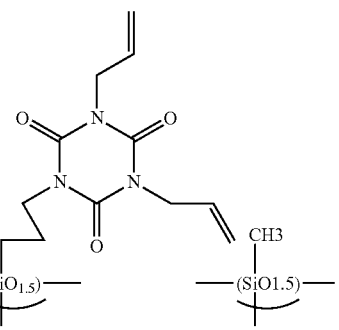

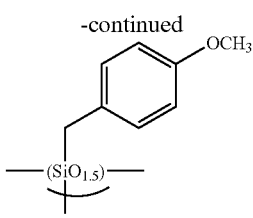

Synthesis Example 11

48.36 g (70 mol %) of tetraethoxysilane, 11.65 g (19.7 mol %) of methyltriethoxysilane, 6.86 g (5 mol %) of 3-(triethoxysilylpropyl)diallylisocyanurate, 4.02 g (5 mol %) of 4-methoxybenzyltrimethoxysilane, 0.27 g (0.3 mol %) of N-(3-triethoxysilylpropyl)-4,5-dihydroimidazole, and 106.73 g of acetone were charged into a 300-mL flask and while stirring the mixture solution with a magnetic stirrer, 22.11 g of a 0.10-mol/L hydrochloric acid was dropped into the mixture solution. After the dropping, the flask was placed into an oil bath controlled to 85° C. and under warming-reflux, the reaction was effected for 240 minutes. Then, to the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-16) measured by GPC was Mw 1,800 in terms of polystyrene.

Formula (3-16)

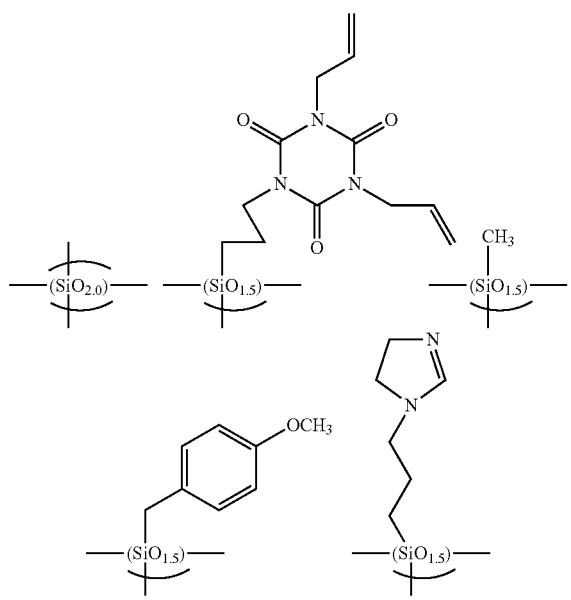

Synthesis Example 12

49.07 g (70 mol %) of tetraethoxysilane, 15.00 g (25 mol %) of methyltriethoxysilane, 6.96 g (5 mol %) of 3-(triethoxysilylpropyl)diallylisocyanurate, and 106.54 g of acetone were charged into a 300-mL flask and while stirring the mixture solution with a magnetic stirrer, 22.43 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-17) measured by GPC was Mw 1,800 in terms of polystyrene.

Formula (3-17)

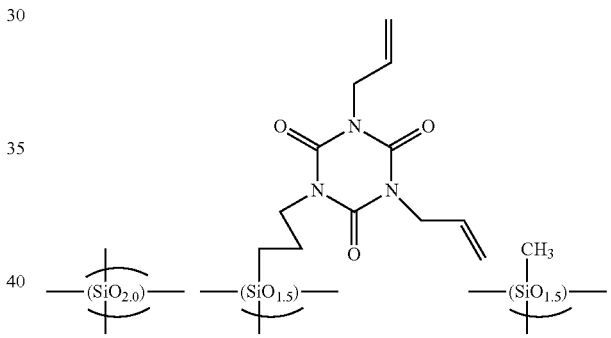

Synthesis Example 13

49.01 g (70 mol %) of tetraethoxysilane, 14.80 g (24.7 mol %) of methyltriethoxysilane, 6.95 g (5 mol %) of 3-(triethoxysilylpropyl)diallylisocyanurate, 0.28 g (0.3 mol %) of N-(3-triethoxysilylpropyl)-4,5-dihydroimidazole, and 106.56 g of acetone were charged into a 300-mL flask and while stirring the mixture solution with a magnetic stirrer, 22.41 g of a 0.10-mon hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/ propylene glycol monoethyl ether became 20/80. The weight average molecular weight of the obtained polymer of Formula (3-18) measured by GPC was Mw 1,800 in terms of polystyrene.

Formula (3-18)

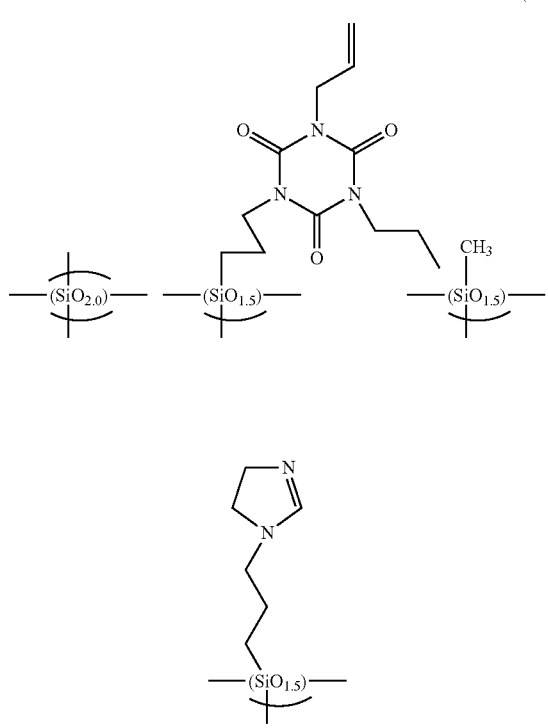

Formula (3-19)

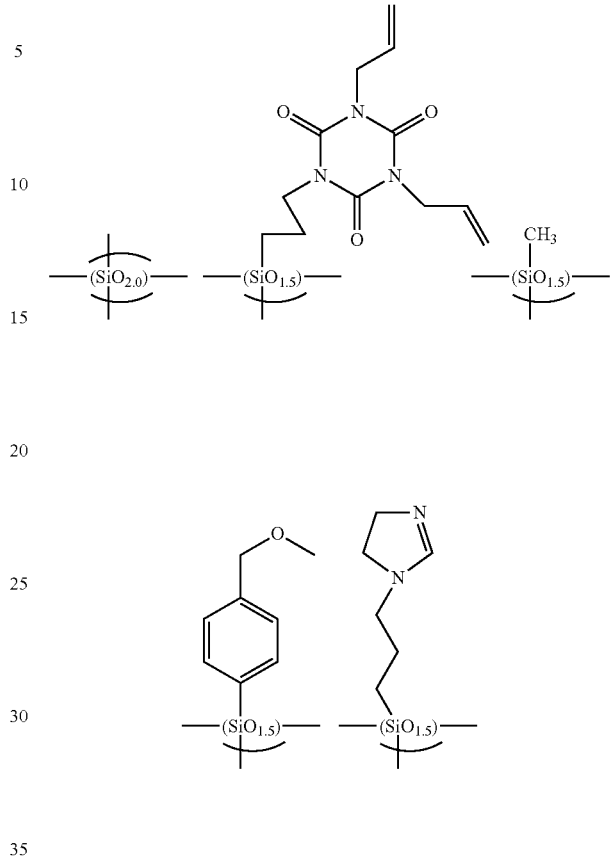

Synthesis Example 14

48.36 g (70 mol %) of tetraethoxysilane, 11.65 g (19.7 mol %) of methyltriethoxysilane, 6.86 g (5 mol %) of 3-(triethoxysilylpropyl)diallylisocyanurate, 4.02 g (5 mol %) of (4-ethoxyphenyl)trimethoxysilane, 0.27 g (0.3 mol %) of N-(3-triethoxysilylpropyl)-4,5-dihydroimidazole, and 106.73 g of acetone were charged into a 300-mL flask and while stirring the mixture solution with a magnetic stirrer, 22.11 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-19) measured by GPC was Mw 1,700 in terms of polystyrene.

Synthesis Example 15

48.50 g (70 mol %) of tetraethoxysilane, 11.68 g (19.7 mol %) of methyltriethoxysilane, 6.88 g (5 mol %) of 3-(triethoxysilylpropyl)diallylisocyanurate, 3.80 g (5 mol %) of (4-methoxyphenyl)trimethoxysilane, 0.27 g (0.3 mol %) of N-(3-triethoxysilylpropyl)-4,5-dihydroimidazole, and 106.70 g of acetone were charged into a 300-mL flask and while stirring the mixture solution with a magnetic stirrer, 22.17 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-20) measured by GPC was Mw 1,800 in terms of polystyrene.

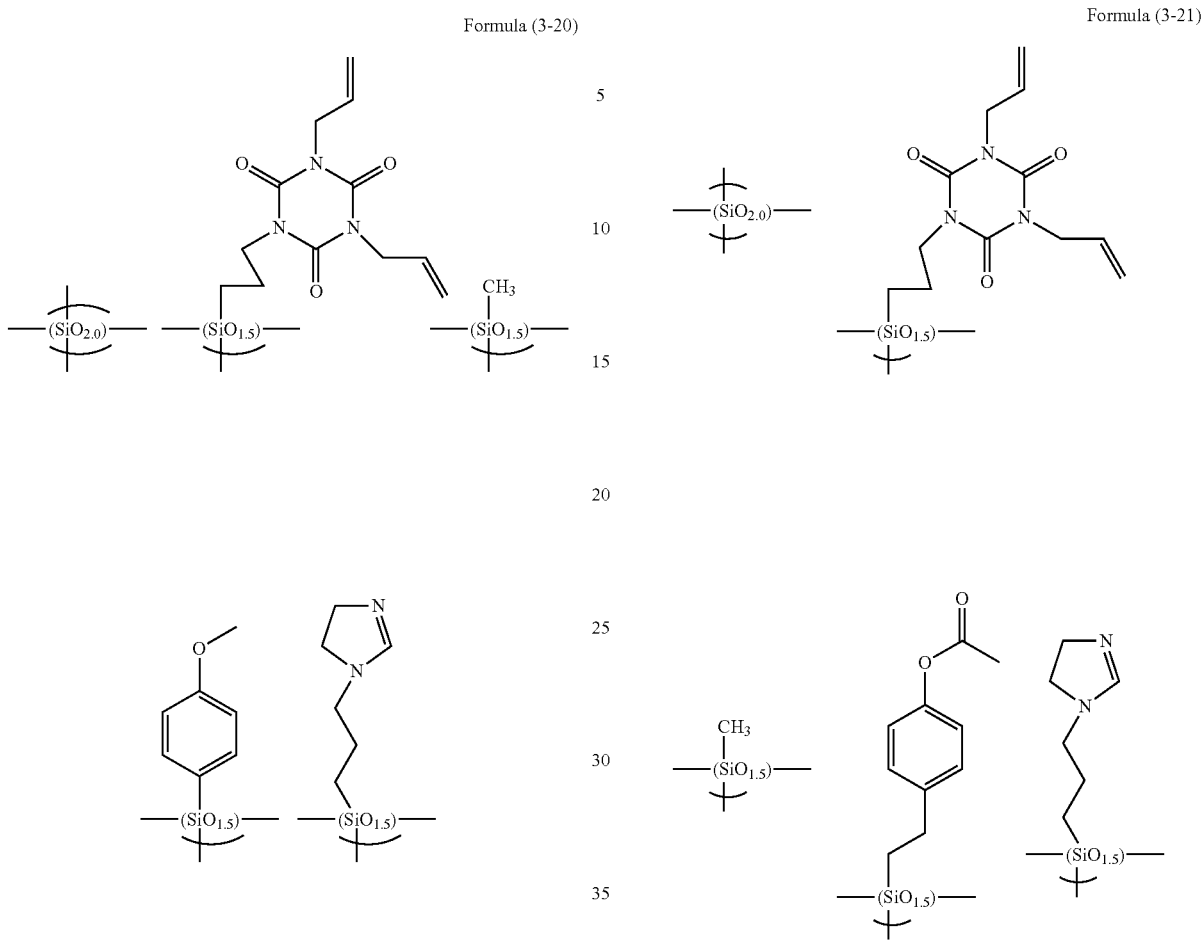

Formula (3-20)

Formula (3-21)

Synthesis Example 16

47.53 g (70 mol %) of tetraethoxysilane, 11.45 g (19.7 mol %) of methyltriethoxysilane, 6.74 g (5 mol %) of 3-(triethoxysilylpropyl)diallylisocyanurate, 5.32 g (5 mol %) of ((4-acetoxyphenyl)ethyl)triethoxysilane, 0.27 g (0.3 mol %) of N-(3-triethoxysilylpropyl)-4,5-dihydroimidazole, and 106.96 g of acetone were charged into a 300-mL flask and while stirring the mixture solution with a magnetic stirrer, 21.73 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-21) measured by GPC was Mw 1,800 in terms of polystyrene.

Synthesis Example 17

48.06 g (70 mol %) of tetraethoxysilane, 11.58 g (19.7 mol %) of methyltriethoxysilane, 6.81 g (5 mol %) of 3-(triethoxysilylpropyl)diallylisocyanurate, 4.49 g (5 mol %) of (4-(1-methoxyethoxy)phenyl)trimethoxysilane, 0.27 g (0.3 mol %) of N-(3-triethoxysilylpropyl)-4,5-dihydroimidazole, and 106.82 g of acetone were charged into a 300-mL flask and while stirring the mixture solution with a magnetic stirrer, 21.97 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-22) measured by GPC was Mw 1,800 in terms of polystyrene.

Formula (3-22)

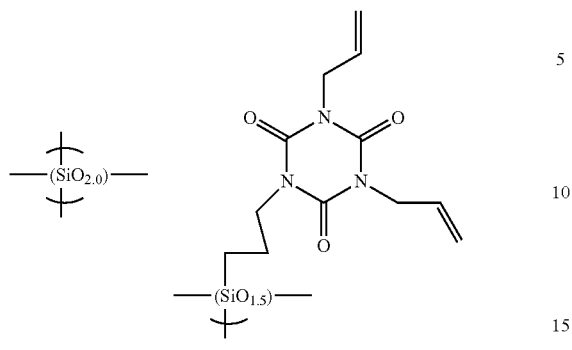

Formula (3-23)

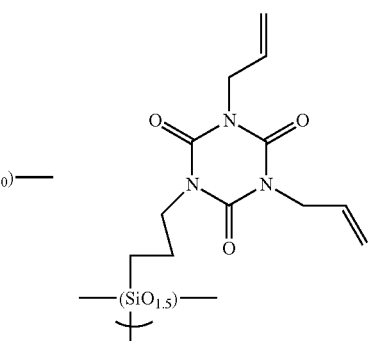

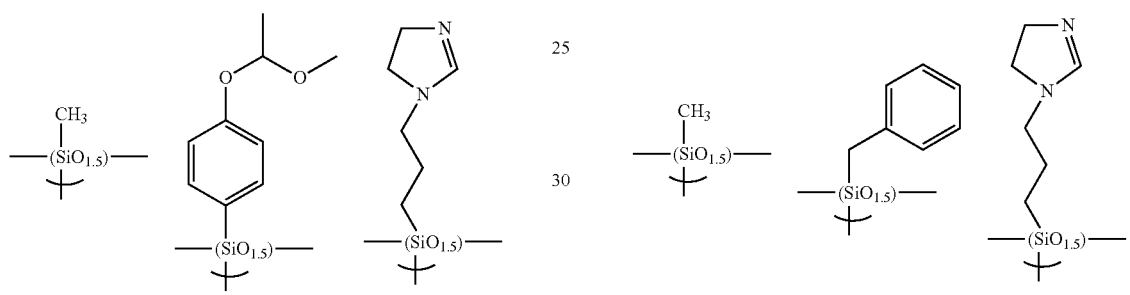

Synthesis Example 18

48.24 g (70 mol %) of tetraethoxysilane, 11.62 g (19.7 mol %) of methyltriethoxysilane, 6.84 g (5 mol %) of 3-(triethoxysilylpropyl)diallylisocyanurate, 4.21 g (5 mol %) of benzyltriethoxysilane, 0.27 g (0.3 mol %) of N-(3-triethoxysilylpropyl)-4,5-dihydroimidazole, and 106.77 g of acetone were charged into a 300-mL flask and while stirring the mixture solution with a magnetic stirrer, 22.05 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-23) measured by GPC was Mw 1,700 in terms of polystyrene.

Synthesis Example 19

48.66 g (70 mol %) of tetraethoxysilane, 11.72 g (19.7 mol %) of methyltriethoxysilane, 6.90 g (5 mol %) of 3-(triethoxysilylpropyl)diallylisocyanurate, 3.54 g (5 mol %) of (4-methylphenyl)trimethoxysilane, 0.27 g (0.3 mol %) of N-(3-triethoxysilylpropyl)-4,5-dihydroimidazole, and 106.65 g of acetone were charged into a 300-mL flask and while stirring the mixture solution with a magnetic stirrer, 22.25 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-24) measured by GPC was Mw 1,700 in terms of polystyrene.

Formula (3-24)

Formula (3-25)

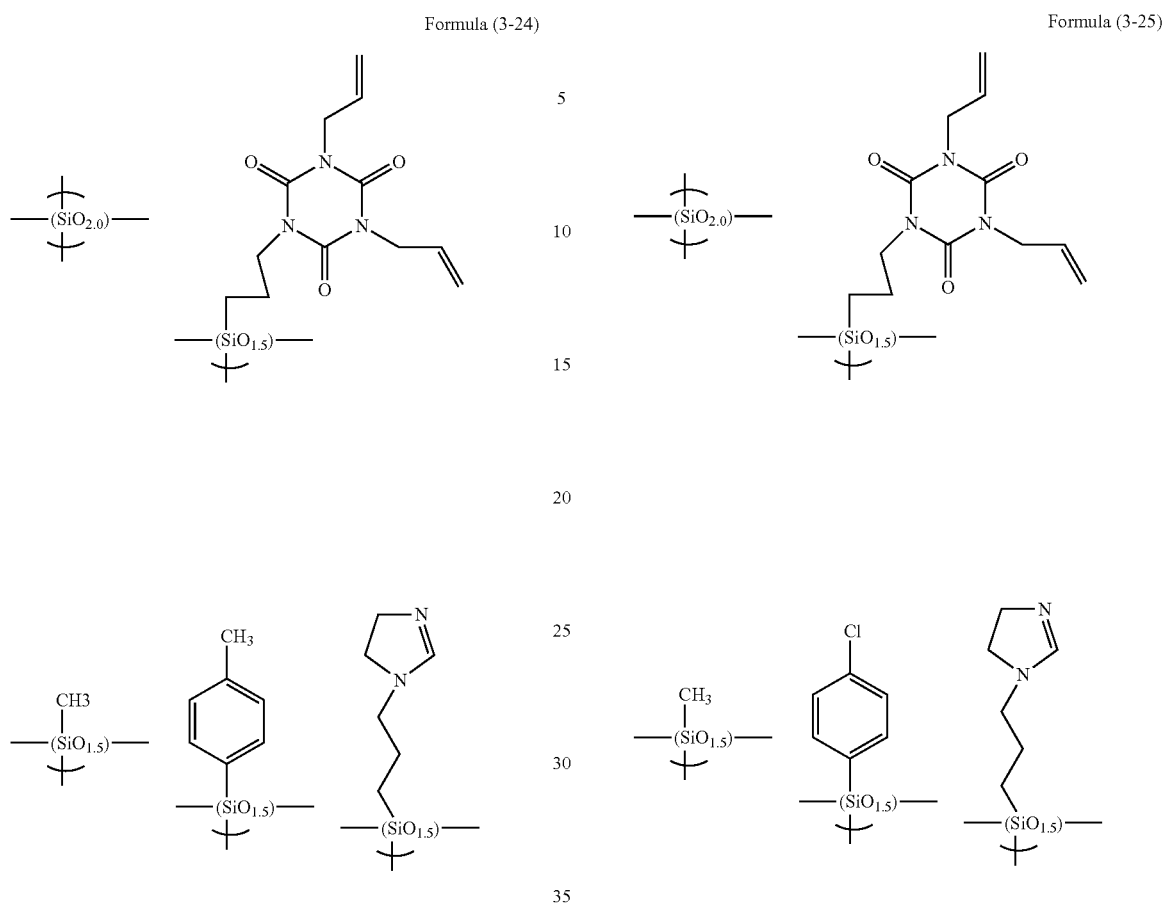

Synthesis Example 20

48.04 g (70 mol %) of tetraethoxysilane, 11.57 g (19.7 mol %) of methyltriethoxysilane, 6.81 g (5 mol %) of 3-(triethoxysilylpropyl)diallylisocyanurate, 4.53 g (5 mol %) of (4-chlorophenyl)triethoxysilane, 0.27 g (0.3 mol %) of N-(3-triethoxysilylpropyl)-4,5-dihydroimidazole, and 106.82 g of acetone were charged into a 300-mL flask and while stirring the mixture solution with a magnetic stirrer, 21.96 g of a 0.10-mol/L hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-25) measured by GPC was Mw 1,700 in terms of polystyrene.

Synthesis Example 21

48.01 g (70 mol %) of tetraethoxysilane, 11.56 g (19.7 mol %) of methyltriethoxysilane, 6.81 g (5 mol %) of 3-(triethoxysilylpropyl)diallylisocyanurate, 4.56 g (5 mol %) of (4-bromophenyl)trimethoxysilane, 0.27 g (0.3 mol %) of N-(3-triethoxysilylpropyl)-4,5-dihydroimidazole, and 106.83 g of acetone were charged into a 300-mL flask and while stirring the mixture solution with a magnetic stirrer, 21.96 g of a 0.10-mon hydrochloric acid was dropped into the mixture solution. After the dropping, the flask was placed into an oil bath controlled to 85° C. and under warming-reflux, the reaction was effected for 240 minutes. To the reaction solution, 142 g of propylene glycol monoethyl ether was added. From the resultant reaction mixture, ethanol and methanol, which were reaction by-products, water, and hydrochloric acid were distilled off under reduced pressure and the resultant reaction mixture was concentrated to obtain a hydrolysis-condensation product (polymer) propylene glycol monoethyl ether solution. To the obtained solution, propylene glycol monoethyl ether and propylene glycol monomethyl ether acetate were added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-26) measured by GPC was Mw 1,700 in terms of polystyrene.

Formula (3-26)

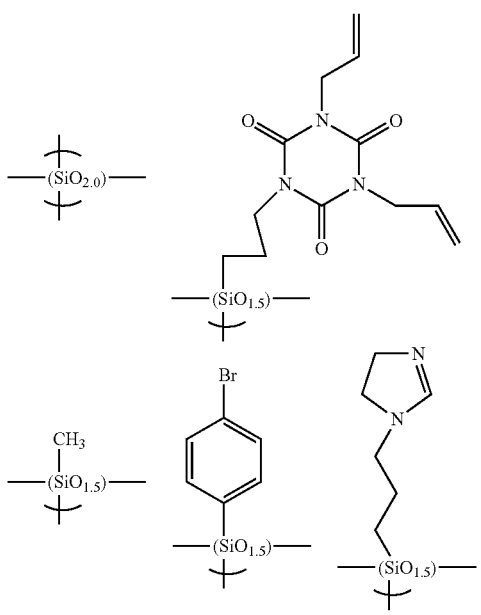

Comparative Synthesis Example 1

50.95 g (70 mol %) of tetraethoxysilane, 9.34 g (15 mol %) of methyltriethoxysilane, 10.39 g (15 mol %) of phenyltrimethoxysilane, and 106.02 g of acetone were charged into a 300-mL flask and while stirring the mixture solution with a magnetic stirrer, 23.29 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-10) measured by GPC was Mw 1,400 in terms of polystyrene.

Formula (3-10)

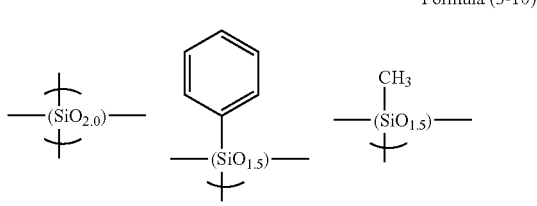

Comparative Synthesis Example 2

Reference Example 55.23 g (70 mol %) of tetraethoxysilane, 10.13 g (15 mol %) of methyltriethoxysilane, 14.67 g (15 mol %) of 4-(methoxymethoxy)trimethoxysilylbenzene, and 104.85 g of acetone were charged into a 300-mL flask and while stirring the mixture solution with a magnetic stirrer, 25.25 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-11) measured by GPC was Mw 1,450 in terms of polystyrene.

Formula (3-11)

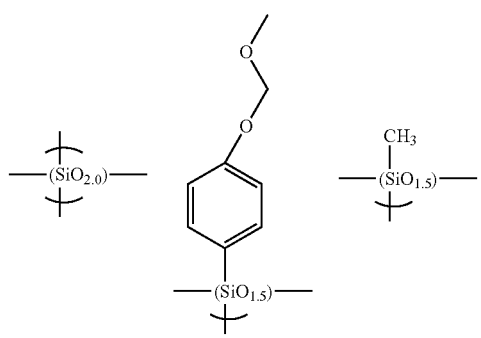

Comparative Synthesis Example 3

Reference Example 55.46 g (70 mol %) of tetraethoxysilane, 10.17 g (15 mol %) of methyltriethoxysilane, 14.40 g (15 mol %) of 2,2-diethoxy-1,5-(o-phenylene)-1-oxa-2-silapentane, and 104.79 g of acetone were charged into a 300-mL flask and while stirring the mixture solution with a magnetic stirrer, 25.36 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-12) measured by GPC was Mw 1,600 in terms of polystyrene.

Formula (3-12)

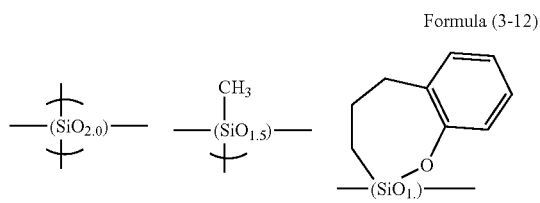

Comparative Synthesis Example 4

44.04 g (70 mol %) of tetraethoxysilane, 8.08 g (15 mol %) of methyltriethoxysilane, 27.90 g (15 mol %) of tris(3-trimethoxysilylpropyl) isocyanurate, and 107.92 g of acetone were charged into a 300-mL flask and while stirring the mixture solution with a magnetic stirrer, 20.14 g of a 0.01-mol/L hydrochloric acid was dropped into the mixture solution. After the dropping, the flask was placed into an oil bath controlled to 85° C. and under warming-reflux, the reaction was effected for 240 minutes. However, partial gelation was caused and the reaction solution became clouded. The obtained polymer is considered to correspond to a polymer of Formula (3-13).

Formula (3-13)

Comparative Synthesis Example 5

53.22 g (70 mol %) of tetraethoxysilane, 9.76 g (15 mol %) of methyltriethoxysilane, 9.81 g (5 mol %) of bis(3-trimethoxysilylpropyl) isocyanurate, 7.24 g (10 mol %) of phenyltrimethoxysilane, and 105.40 g of acetone were charged into a 300-mL flask and while stirring the mixture solution with a magnetic stirrer, 24.33 g of a 0.01-mol/L hydrochloric acid was dropped into the mixture solution. After the dropping, the flask was placed into an oil bath controlled to 85° C. and under warming-reflux, the reaction was effected for 240 minutes. Then, the reaction solution was cooled down to room temperature and to the reaction solution, 142 g of propylene glycol monomethyl ether acetate was added. From the resultant reaction mixture, ethanol, which was a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monomethyl ether was added to adjust the resultant solution to have a solid residue concentration at 140° C. of 15% by weight while a solvent ratio of propylene glycol monomethyl ether acetate/propylene glycol monoethyl ether became 20/80. The weight average molecular weight of the obtained polymer of Formula (3-14) measured by GPC was Mw 11,000 in terms of polystyrene.

Formula (3-14)

(Preparation of Resist Underlayer Film)

By blending each of the silicon-containing polymers obtained in Synthesis Examples 1 to 21 and Comparative Synthesis Examples 1 to 3 and 5, an acid, a curing catalyst, an additive, a solvent, and water in ratios shown in Table 1 and by filtering the resultant blend with a 0.1 μm fluorinated resin filter, each of the solutions of the resist underlayer film forming compositions of Examples 1 to 25, Comparative Examples 1 and 2, and Reference Examples 1 and 2 was prepared. In Table 1, the blending ratio of the polymer indicates not the blending amount of the polymer solution, but the blending amount of the polymer it self.

In Table 1: maleic acid is abbreviated as MA; benzyltriethylammonium chloride is abbreviated as BTAC; N-(3-triethoxysilylpropyl)-4,5-dihydroimidazole is abbreviated as IMTEOS; triphenylsulfoniumtrifluoromethane sulfonate is abbreviated as TPS105; monotriphenylsulfonium maleate is abbreviated as TPSMA; bisphenol S is abbreviated as BPS; propylene glycol monomethyl ether acetate is abbreviated as PGMEA; propylene glycol monoethyl ether is abbreviated as PGEE; and propylene glycol monomethyl ether is abbreviated as PGME. As the water, ultrapure water was used. Each blending amount is expressed in parts by mass.

TABLE 1

| | Polymer | Acid | Curing catalyst | Additive | Solvent | | | Water |
|---|---|---|---|---|---|---|---|---|
| Example 1 (parts by mass) | Synthesis Example 1 | MA 0.06 | BTAC 0.012 | | PGMEA 7 | PGEE 80 | | Water 13 |
| Example 2 (parts by mass) | Synthesis Example 2 | MA 0.06 | BTAC 0.012 | | PGMEA 7 | PGEE 80 | | Water 13 |
| Example 3 (parts by mass) | Synthesis Example 3 | MA 0.06 | BTAC 0.012 | | PGMEA 7 | PGEE 80 | | Water 13 |
| Example 4 (parts by mass) | Synthesis Example 3 | MA 0.06 | TPSMA 0.012 | | PGMEA 7 | PGEE 80 | | Water 13 |
| Example 5 (parts by mass) | Synthesis Example 3 | MA 0.06 | IMTEOS 0.012 | | PGMEA 7 | PGEE 80 | | Water 13 |
| Example 6 (parts by mass) | Synthesis Example 3 | MA 0.06 | IMTEOS 0.012 | TPS105 0.02 | PGMEA 7 | PGEE 80 | | Water 13 |
| Example 7 (parts by mass) | Synthesis Example 3 | MA 0.06 | BTAC 0.012 | BPS 0.02 | PGMEA 7 | PGEE 80 | | Water 13 |
| Example 8 (parts by mass) | Synthesis Example 4 | MA 0.06 | IMTEOS 0.012 | | PGMEA 7 | PGEE 80 | | Water 13 |
| Example 9 (parts by mass) | Synthesis Example 5 | MA 0.06 | IMTEOS 0.012 | | PGMEA 7 | PGEE 80 | | Water 13 |
| Example 10 (parts by mass) | Synthesis Example 6 | MA 0.06 | IMTEOS 0.012 | | PGMEA 7 | PGEE 80 | | Water 13 |
| Example 11 (parts by mass) | Synthesis Example 7 | MA 0.06 | | | PGMEA 7 | PGEE 80 | | Water 13 |
| Example 12 (parts by mass) | Synthesis Example 8 | MA 0.06 | | | PGMEA 7 | PGEE 80 | | Water 13 |
| Example 13 (parts by mass) | Synthesis Example 9 | MA 0.06 | | | PGMEA 7 | PGEE 80 | | Water 13 |
| Example 14 (parts by mass) | Synthesis Example 10 | MA 0.06 | IMTEOS 0.012 | | PGME 10 | PGMEA 7 | PGEE 76 | Water 7 |
| Example 15 (parts by mass) | Synthesis Example 11 | MA 0.06 | | | PGME 10 | PGMEA 7 | PGEE 76 | Water 7 |
| Example 16 (parts by mass) | Synthesis Example 12 | MA 0.06 | IMTEOS 0.012 | BPS 0.1 | PGME 10 | PGMEA 7 | PGEE 76 | Water 7 |
| Example 17 (parts by mass) | Synthesis Example 13 | MA 0.06 | | BPS 0.1 | PGME 10 | PGMEA 7 | PGEE 76 | Water 7 |
| Example 18 (parts by mass) | Synthesis Example 14 | MA 0.06 | | | PGME 10 | PGMEA 7 | PGEE 76 | Water 7 |
| Example 19 (parts by mass) | Synthesis Example 15 | MA 0.06 | | | PGME 10 | PGMEA 7 | PGEE 76 | Water 7 |
| Example 20 (parts by mass) | Synthesis Example 16 | MA 0.06 | | | PGME 10 | PGMEA 7 | PGEE 76 | Water 7 |
| Example 21 (parts by mass) | Synthesis Example 17 | MA 0.06 | | | PGME 10 | PGMEA 7 | PGEE 76 | Water 7 |
| Example 22 (parts by mass) | Synthesis Example 18 | MA 0.06 | | | PGME 10 | PGMEA 7 | PGEE 76 | Water 7 |
| Example 23 (parts by mass) | Synthesis Example 19 | MA 0.06 | | | PGME 10 | PGMEA 7 | PGEE 76 | Water 7 |
| Example 24 (parts by mass) | Synthesis Example 20 | MA 0.06 | | | PGME 10 | PGMEA 7 | PGEE 76 | Water 7 |
| Example 25 (parts by mass) | Synthesis Example 21 | MA 0.06 | | | PGME 10 | PGMEA 7 | PGEE 76 | Water 7 |

TABLE 1-continued

| | Polymer | Acid | Curing catalyst | Additive | | Solvent | | Water |
|---|---|---|---|---|---|---|---|---|
| Comparative Example 1 (parts by mass) | Comparative Synthesis Example 1 2 | MA 0.06 | BTAC 0.012 | | PGMEA 7 | PGEE 80 | | Water 13 |
| Comparative Example 2 (parts by mass) | Comparative Synthesis Example 5 2 | MA 0.06 | BTAC 0.012 | | PGMEA 7 | PGEE 80 | | Water 13 |
| Reference Example 1 (parts by mass) | Comparative Synthesis Example 2 2 | MA 0.06 | BTAC 0.012 | | PGMEA 7 | PGEE 80 | | Water 13 |
| Reference Example 2 (parts by mass) | Comparative Synthesis Example 3 2 | MA 0.06 | BTAC 0.012 | | PGMEA 7 | PGEE 80 | | Water 13 |

(Solvent Resistance Test)

Each of the silicon-containing resist underlayer film forming compositions prepared in Examples 1 to 25, Comparative Examples 1 and 2, and Reference Examples 1 and 2 was applied on a silicon wafer by a spin coating method and the composition was baked on a hot plate of 240° C. for 1 minute to form a silicon-containing resist underlayer film. Then, the resist underlayer film was immersed in propylene glycol monomethyl ether acetate used as a solvent for an over coating resist composition for 1 minute. When the change in the film thickness of the resist underlayer film between before and after the immersion was 1 nm or less, it was determined as "advantageous" and was indicated with "○", and when the change in the film thickness was 1 nm or more, it was determined as "disadvantageous" and was indicated with "x".

(Measurement of Optical Constants)

Each of the silicon-containing resist underlayer film forming compositions prepared in Examples 1 to 25, Comparative Examples 1 and 2, and Reference Examples 1 and 2 was applied onto a silicon wafer using a spinner. The composition was heated on a hot plate at 240° C. for 1 minute to form a silicon-containing resist underlayer film (film thickness: 0.05 μm). Then, the refractive index (n value) and the optical absorptivity (k value; also called as the attenuation coefficient) at a wavelength of 193 nm of the resist underlayer film were measured using a spectro-ellipsometer (VUV-VASE VU-302; manufactured by J.A. Woollam Co., Inc.).

(Preparation of Organic Underlayer Film)

Into a 200-mL flask, 16.5 g of acenaphthylene, 1.5 g of 4-hydroxystyrene, and 60 g of 1,2-dichloroethane as a solvent were charged. Thereto, 1 g of trifluoro boron as a polymerization initiator was added and the resultant reaction mixture was heated to 60° C. and was then subjected to the reaction for 24 hours. To this solution, 1 L of methanol and 500 g of water were added and the resultant reaction mixture was subjected to a re-precipitation purification, followed by filtering and drying the resultant white solid to obtain 11 g of a white polymer.

The obtained polymer below:

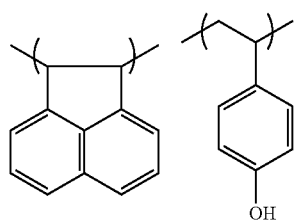

was measured by $^{13}$C-NMR, $^{1}$H-NMR, and GPC and was found to be acenaphthylene:4-hydroxystyrene=86:14.

The average molecular weight (Mw) of the obtained polymer was 6,000, and the molecular weight distribution (Mw/Mn) was 1.5.

To 10 g of the obtained polymer, 1.0 g of tetramethoxymethyl glycoluril (trade name: POWDER LINK 1174; manufactured by Mitsui Cytec Ltd.), 0.01 g of p-toluenesulfonic acid as a crosslinking catalyst, and 0.03 g of MEGAFAC (registered trade mark) R-30 (trade name; manufactured by DIC Corporation) as a surfactant were added and the resultant mixture was dissolved in 101.57 g of propylene glycol monomethyl ether acetate and 25.39 g of propylene glycol monomethyl ether. Then, the resultant solution was filtered using a polyethylene microfilter having a pore diameter of 0.10 μm and was further filtered using a polyethylene microfilter having a pore diameter of 0.05 μm to prepare a solution of an organic underlayer film forming composition to be used for a lithography process by a multilayer film.

(Measurement of Dry Etching Rate)

Etchers and etching gases used in the measurement of dry etching rates were as follows.

ES401 (manufactured by Nippon Scientific Co., Ltd.): $CF_4$

RIE-10NR (manufactured by Samco, Inc.): $O_2$

Each of the solutions of the silicon-containing resist underlayer film forming compositions prepared in Examples 1 to 25, Comparative Examples 1 and 2, and Reference Examples 1 and 2 was applied onto a silicon wafer using a spinner. The composition solution was heated on a hot plate at 240° C. for 1 minute to form each of the silicon-containing resist underlayer films (film thickness: 0.08 μm (for measurement of etching rate with $CF_4$ gas), film thickness: 0.05 μm (for measurement of etching rate with $O_2$ gas)). Then, using $CF_4$ gas or $O_2$ gas as the etching gas, the etching rate was measured. In the same manner, an organic underlayer film forming composition was applied onto a silicon wafer using a spinner to form a coating film thereof. By using $O_2$ gas as the etching gas, there was measured the dry etching rate of the organic underlayer film, which was in turn compared with the dry etching rate of each of the silicon-containing resist underlayer films of Examples 1 to 25, Comparative Examples 1 and 2, and Reference Examples 1 and 2.

Table 1 shows the refractive index n of the underlayer film at a wavelength of 193 nm; the optical absorptivity k of the underlayer film at a wavelength of 193 nm; the solvent resistance against propylene glycol monomethyl ether acetate (PGMEA); the etching rate (nm/min) with a fluorine-based gas ($CF_4$ gas); and the resistance against an oxygen-based gas ($O_2$ gas) calculated from the etching rate ratio of the resist underlayer film of the present specification to the organic underlayer film.

TABLE 2

|  | Refractive index | Optical absorptivity | Solvent resistance | Etching rate with fluorine-based gas (nm/min) | Oxygen-based gas resistance |
|---|---|---|---|---|---|
| Example 1 | 1.80 | 0.20 | ∘ | 21.5 | 0.05 |
| Example 2 | 1.79 | 0.18 | ∘ | 22.0 | 0.05 |
| Example 3 | 1.77 | 0.30 | ∘ | 19.0 | 0.03 |
| Example 4 | 1.76 | 0.31 | ∘ | 18.9 | 0.03 |
| Example 5 | 1.75 | 0.31 | ∘ | 19.1 | 0.03 |
| Example 6 | 1.74 | 0.32 | ∘ | 18.9 | 0.03 |
| Example 7 | 1.74 | 0.31 | ∘ | 19.0 | 0.03 |
| Example 8 | 1.75 | 0.29 | ∘ | 18.9 | 0.03 |
| Example 9 | 1.75 | 0.28 | ∘ | 19.0 | 0.03 |
| Example 10 | 1.76 | 0.28 | ∘ | 19.2 | 0.03 |
| Example 11 | 1.76 | 0.30 | ∘ | 18.8 | 0.03 |
| Example 12 | 1.76 | 0.30 | ∘ | 19.0 | 0.03 |
| Example 13 | 1.62 | 0.22 | ∘ | 19.1 | 0.03 |
| Example 14 | 1.63 | 0.19 | ∘ | 19.3 | 0.03 |
| Example 15 | 1.63 | 0.19 | ∘ | 19.3 | 0.03 |
| Example 16 | 1.63 | 0.12 | ∘ | 19.0 | 0.02 |
| Example 17 | 1.63 | 0.12 | ∘ | 19.0 | 0.02 |
| Example 18 | 1.61 | 0.20 | ∘ | 19.3 | 0.03 |
| Example 19 | 1.63 | 0.22 | ∘ | 19.3 | 0.03 |
| Example 20 | 1.67 | 0.20 | ∘ | 19.5 | 0.03 |
| Example 21 | 1.62 | 0.21 | ∘ | 19.5 | 0.03 |
| Example 22 | 1.65 | 0.21 | ∘ | 19.0 | 0.03 |
| Example 23 | 1.60 | 0.20 | ∘ | 19.0 | 0.03 |
| Example 24 | 1.66 | 0.22 | ∘ | 19.5 | 0.03 |
| Example 25 | 1.65 | 0.18 | ∘ | 19.5 | 0.03 |
| Comparative Example 1 | 1.74 | 0.37 | ∘ | 17.8 | 0.03 |
| Comparative Example 2 | 1.75 | 0.28 | ∘ | 19.5 | 0.03 |
| Reference Example 1 | 1.52 | 0.37 | ∘ | 18.9 | 0.03 |
| Reference Example 2 | 1.55 | 0.36 | ∘ | 17.2 | 0.03 |

(Resist Patterning Evaluation)

The organic underlayer film (underlayer) forming composition prepared as described above was applied onto a silicon wafer and the composition was heated on a hot plate at 240° C. for 1 minute to obtain an organic underlayer film (layer A) having a film thickness of 200 nm. Onto the organic underlayer film, each of the silicon-containing resist underlayer film (intermediate layer) forming compositions obtained in Examples 1 to 25 and Comparative Examples 1 and 2 was applied and the composition was heated on a hot plate at 240° C. for 1 minute to obtain a silicon-containing resist underlayer film (layer B). The silicon-containing resist underlayer films (intermediate layer) formed from the compositions of Examples 1 to 12 and Comparative Examples 1 and 2 had a film thickness of 20 nm and the silicon-containing resist underlayer films (intermediate layer) formed from the compositions of Examples 13 to 25 had a film thickness of 40 nm.

Onto each resist underlayer film, a commercially available photoresist solution (trade name: PAR 855; manufactured by Sumitomo Chemical Co., Ltd.) was applied by a spinner and the solution was heated on a hot plate at 100° C. for 1 minute to form a photoresist film (upper layer) having a film thickness of 150 nm. The patterning of the resist was performed using an immersion exposing machine (trade name: TWIN-SCAN XT 1900Gi scanner; manufactured by ASML Holding N.V. (wavelength: 193 nm, NA, σ: 1.20, 0.94/0.74 (C-quad), immersion liquid: water). The target was a photoresist after the development having a line width and a width between lines of 0.05 μm each, which is a so-called line and space (dense line), and the exposure was performed through a mask set to form 15 lines.

Then, the resist pattern was baked on a hot plate at 105° C. for 60 seconds, was cooled down, and was developed with a tetramethylammonium hydroxide aqueous solution (developer) having a concentration of 2.38% by mass in a 60-second single paddle process.

(Preservation Stability Evaluation)

The film thickness measurement and the lithography evaluation of the coating film of the resist underlayer film forming composition on a silicon wafer immediately after the production of the coating film were performed. Thereafter, the resist underlayer film forming composition was preserved at 35° C. for 2 months and the film thickness measurement and the lithography evaluation were performed again.

With respect to the resist pattern skirt shape after the lithography was performed, a shape having a straight line was evaluated as "advantageous" and a shape having an undercut (tapering of the bottom portion), a footing (spreading of the bottom portion), or a pattern peeling was evaluated as "disadvantageous". Even in the case where a slight footing was partially observed, when there is practically no problem, such a shape was evaluated as "advantageous (with proviso that footing partially existed)".

The case where there was no change in the coating film thickness after the preservation at 35° C. for 2 months, was evaluated as "∘" and when there was a change, the changed amount was indicated.

TABLE 3

|  | Lithography evaluation | Change in coating film thickness after preservation at 35° C. for 2 months | Lithography evaluation after preservation at 35° C. for 2 months |
|---|---|---|---|
| Example 1 | Advantageous | ∘ | Advantageous |
| Example 2 | Advantageous | ∘ | Advantageous |
| Example 3 | Advantageous | ∘ | Advantageous |
| Example 4 | Advantageous | ∘ | Advantageous |
| Example 5 | Advantageous | ∘ | Advantageous |
| Example 6 | Advantageous | ∘ | Advantageous |
| Example 7 | Advantageous | ∘ | Advantageous |
| Example 8 | Advantageous | ∘ | Advantageous |
| Example 9 | Advantageous | ∘ | Advantageous |
| Example 10 | Advantageous (partially footing) | ∘ | Advantageous |
| Example 12 | Advantageous | ∘ | Advantageous |
| Example 13 | Advantageous | ∘ | Advantageous |
| Example 14 | Advantageous | ∘ | Advantageous |
| Example 15 | Advantageous | ∘ | Advantageous |
| Example 16 | Advantageous | ∘ | Advantageous |
| Example 17 | Advantageous | ∘ | Advantageous |
| Example 18 | Advantageous | ∘ | Advantageous |
| Example 19 | Advantageous | ∘ | Advantageous |
| Example 20 | Advantageous | ∘ | Advantageous |
| Example 21 | Advantageous | ∘ | Advantageous |
| Example 22 | Advantageous | ∘ | Advantageous |
| Example 23 | Advantageous | ∘ | Advantageous |

TABLE 3-continued

| | Lithography evaluation | Change in coating film thickness after preservation at 35° C. for 2 months | Lithography evaluation after preservation at 35° C. for 2 months |
|---|---|---|---|
| Example 24 | Advantageous | ○ | Advantageous |
| Example 25 | Advantageous | ○ | Advantageous |
| Comparative Example 1 | Undercut (partially peeling) | — | — |
| Comparative Example 2 | Advantageous | Increase by 10% | Partially peeling |

(Evaluation of Uneven Distribution in Surface)

There was investigated the distribution of a siloxane component derived from the hydrolyzable organosilane of Formula (1) in the resist underlayer film of the present specification containing as the main component, the polysiloxane produced by the hydrolysis and the condensation of the silane composition containing the hydrolyzable organosilane of Formula (1) in the resist underlayer film.

In order to investigate the distribution in the film, there was performed the component analysis in the depth direction by a scanning X-ray photoelectron spectroscopic analysis. The resist underlayer film forming composition of Example 5 was applied onto a silicon wafer by a spin coating method and the composition was baked on a hot plate of 240° C. for 1 minute to form a silicon-containing resist underlayer film of 50 nm. By using an XPS apparatus (PHI Quantera SXM; manufactured by ULVAC-PHI, Inc.), a C1s peak and an N1s peak of carbon of the carbonyl in isocyanurate were measured.

As a result, in the outermost surface, peaks of carbon and nitrogen of the carbonyl were confirmed and it was confirmed that an isocyanurate group is unevenly distributed in the surface. It is considered that by being unevenly distributed selectively in the surface, the isocyanurate group effectively modifies the interface of the resist underlayer film with the resist.

INDUSTRIAL APPLICABILITY

There can be provided a resist underlayer film forming composition for lithography for forming a resist underlayer film capable of being used as a hardmask. In addition, the resist underlayer film forming composition for lithography is also a resist underlayer film forming composition for lithography for forming a resist underlayer film capable of being used as an anti-reflective coating.

The invention claimed is:

1. A resist underlayer film forming composition for lithography, comprising a silane compound, wherein the silane compound is a hydrolyzable organosilane, a hydrolysis product thereof, or a hydrolysis-condensation product thereof, wherein the composition comprises as the hydrolyzable organosilane both (1) a hydrolyzable organosilane of Formula (1), and (2) a hydrolyzable organosilane of Formula (6), and wherein the composition comprises at least the hydrolysis-condensation product of the hydrolyzable organosilane of Formula (1) and the hydrolyzable silane of Formula (6) as a polymer:

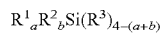  Formula (1)

where $R^1$ is Formula (2):

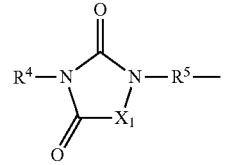  Formula (2)

where in Formula (2), $R^4$ is a hydrogen atom, a $C_{1-10}$ alkyl group, an alkenyl group, an epoxy group, a sulfonyl group, or an organic group containing these groups and containing no Si atoms; $R^5$ is a $C_{1-10}$ alkylene group, a hydroxyalkylene group, a sulfide bond, an ether bond, an ester bond, or a combination thereof; and $X_1$ is Formula (3), Formula (4), or Formula (5):

  Formula (3)

  Formula (4)

  Formula (5)

where in Formula (3), Formula (4), and Formula (5), $R^6$ to $R^{10}$ are independently a hydrogen atom, a $C_{1-10}$ alkyl group, an alkenyl group, an epoxy group, a sulfonyl group, or an organic group containing these groups, and $R^1$ is bonded to a silicon atom through a Si—C bond;

where $R^2$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, or a cyano group, or a combination thereof, and is bonded to a silicon atom through a Si—C bond;

where $R^3$ is an alkoxy group, an acyloxy group, or a halogen group; and where a is an integer of 1 and b is an integer of 0 or 1, and where a+b is an integer of 1 or 2;

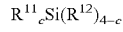  Formula (6)

where $R^{11}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, an amino group, a sulfonyl group, a sulfide bond, an ether bond, an ester bond, a sulfonamide group, or a cyano group, or a combination thereof, and is bonded to a silicon atom through a Si—C bond;

where $R^{12}$ is an alkoxy group, an acyloxy group, or a halogen group; and where c is an integer of 0 to 3.

2. The composition according to claim 1, wherein the composition further comprises a hydrolyzable organosilane of Formula (7):

   Formula (7)

where $R^{13}$ is a cyclic amine or an organic group containing the same, and is bonded to a silicon atom through a Si—N bond or a Si—C bond;

where $R^{14}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond;

where $R^{15}$ is an alkoxy group, an acyloxy group, or a halogen group; and where d is an integer of 1 or 2 and e is an integer of 0 or 1, and where d+e is an integer of 1 or 2, or a hydrolysis product thereof, or a hydrolysis-condensation product thereof.

3. The composition according to claim 1, wherein the composition further comprises a hydrolyzable organosilane of Formula (8):

   Formula (8)

where $R^{16}$ is an alkoxyphenyl group, an acyloxyphenyl group, or an organic group containing these groups, and is bonded to a silicon atom through a Si—C bond;

where $R^{17}$ is an alkyl group, an aryl group, an aralkyl group, a halogenated alkyl group, a halogenated aryl group, a halogenated aralkyl group, an alkenyl group, or an organic group having an epoxy group, an acryloyl group, a methacryloyl group, a mercapto group, or a cyano group, or a combination thereof, and is bonded to a silicon atom through a Si—C bond;

where $R^{18}$ is an alkoxy group, an acyloxy group, or a halogen group; where $R^{16}$ and $R^{17}$ together optionally form a ring; and where f is an integer of 1 or 2 and g is an integer of 0 or 1, where f+g is an integer of 1 or 2, or a hydrolysis product thereof, or a hydrolysis-condensation product thereof.

4. The composition according to claim 1, further comprising an acid.

5. The composition according to claim 1, further comprising a salt.

6. The composition according to claim 1, further comprising water.

7. The composition according to claim 1, further comprising bisphenol S or a derivative thereof.

8. The composition according to claim 1, wherein the hydrolyzable organosilane of Formula (1) is a hydrolyzable organosilane containing diallyl isocyanurate and the hydrolyzable silane of Formula (6) is a tetraalkoxysilane.

9. The composition according to claim 1, wherein the hydrolyzable organosilane of Formula (1) is a hydrolyzable organosilane containing diallyl isocyanurate and the hydrolyzable organosilane of Formula (6) is a tetraalkoxysilane and an unsubstituted or substituted phenyltrialkoxysilane.

10. The composition according to claim 3, wherein the hydrolyzable organosilane of Formula (1) is a silane compound containing diallyl isocyanurate, the hydrolyzable silane of Formula (6) is a tetraalkoxysilane, and the hydrolyzable organosilane of Formula (8) is a silane compound containing an alkoxyphenyl group.

11. The composition according to claim 3, wherein the hydrolyzable organosilane of Formula (1) is a silane compound containing diallyl isocyanurate, the hydrolyzable silane of Formula (6) is a tetraalkoxysilane and an unsubstituted or substituted phenyltrialkoxysilane, and the hydrolyzable organosilane of Formula (8) is a hydrolyzable organosilane containing an alkoxyphenyl group.

12. A resist underlayer film obtained by applying the resist underlayer film forming composition as claimed in claim 1 on a semiconductor substrate and baking the resultant coating film.

13. A production method of a semiconductor device, comprising:
    applying the resist underlayer film forming composition as claimed in claim 1 on a semiconductor substrate and baking the resultant coating film to form a resist underlayer film;
    applying a resist film forming composition on the underlayer film to form a resist film;
    exposing the resist film to light;
    developing the resist film after the exposure to obtain a patterned resist film;
    etching the resist underlayer film according to the patterned resist film to pattern the resist underlayer film; and
    processing the semiconductor substrate according to the patterned resist film and the patterned resist underlayer film.

14. A production method of a semiconductor device, comprising:
    forming an organic underlayer film on a semiconductor substrate;
    applying the resist underlayer film forming composition as claimed in claim 1 on the organic underlayer film and baking the resultant coating film to form a resist underlayer film;
    applying a resist film forming composition on the resist underlayer film to form a resist film;
    exposing the resist film to light;
    developing the resist film after the exposure to obtain a patterned resist film;
    etching the resist underlayer film according to the patterned resist film to pattern the resist underlayer film;
    etching the organic underlayer film according to the patered resist film and the patterned resist underlayer film; and
    processing the semiconductor substrate according to the patterned organic underlayer film.

15. The composition according to claim 1, wherein the silane comprises 20% by mass or more of the composition on a solids basis.

16. The composition according to claim 1, wherein the silane comprises 50% to 100% by mass of the composition on a solids basis.

* * * * *